(12) United States Patent
Hammer

(10) Patent No.: US 12,636,458 B2
(45) Date of Patent: May 26, 2026

(54) HEADGEAR FOR A PATIENT INTERFACE

(71) Applicant: Fisher & Paykel Healthcare Limited, Auckland (NZ)

(72) Inventor: Jeroen Hammer, Auckland (NZ)

(73) Assignee: Fisher & Paykel Healthcare Limited, Auckland (NZ)

(*) Notice: Subject to any disclaimer, the term of this patent is extended or adjusted under 35 U.S.C. 154(b) by 728 days.

(21) Appl. No.: 17/999,263

(22) PCT Filed: May 19, 2021

(86) PCT No.: PCT/IB2021/054290
§ 371 (c)(1),
(2) Date: Nov. 18, 2022

(87) PCT Pub. No.: WO2021/234583
PCT Pub. Date: Nov. 25, 2021

(65) Prior Publication Data
US 2023/0181859 A1     Jun. 15, 2023

Related U.S. Application Data

(60) Provisional application No. 63/027,243, filed on May 19, 2020.

(51) Int. Cl.
*A61M 16/06*          (2006.01)

(52) U.S. Cl.
CPC .... *A61M 16/0688* (2014.02); *A61M 16/0627* (2014.02); *A61M 2016/0661* (2013.01); *A61M 2205/582* (2013.01)

(58) Field of Classification Search
CPC .......... A61M 16/0616; A61M 16/0627; A61M 2016/0661; A61M 16/0688; A61M 16/0622; A41D 13/1169
See application file for complete search history.

(56) References Cited

U.S. PATENT DOCUMENTS

| | | | |
|---|---|---|---|
| 4,410,575 A | 10/1983 | Obayashi |
| 4,418,745 A | 12/1983 | Roehr |
| 4,831,664 A | 5/1989 | Suda |
| 5,699,791 A | 12/1997 | Sukiennik |
| 5,701,893 A | 12/1997 | Kern |

(Continued)

FOREIGN PATENT DOCUMENTS

| | | |
|---|---|---|
| AU | 532211 B2 | 9/1983 |
| AU | 2015218417 A1 | 9/2015 |

(Continued)

*Primary Examiner* — Tajash D Patel
(74) *Attorney, Agent, or Firm* — VIA LLP

(57) ABSTRACT

A headgear for a patient interface, such as a respiratory interface, includes a plurality of panels which are lapped against each other. The panels define lapped parts of the headgear where panels overlap and/or underlap each other, and non-lapped parts of the headgear where a panel or panels are not lapped by another panel. The panels at the lapped regions are bonded to each other by an adhesive, such as a hot-melt adhesive. By combining panels having different properties, interfaces between panels having different lapping configurations, and by controlling the properties such as extensibility and stiffness of the adhesive when set a headgear may be provided location-specific features and properties.

20 Claims, 33 Drawing Sheets

(56)        References Cited

U.S. PATENT DOCUMENTS

| | | | |
|---|---|---|---|
| 5,717,991 | A | 2/1998 | Nozaki |
| 5,724,677 | A | 3/1998 | Bryant |
| 5,885,679 | A | 3/1999 | Yasue |
| 6,036,811 | A | 3/2000 | Mcgraw |
| 6,055,982 | A | 5/2000 | Brunson |
| 6,070,579 | A | 6/2000 | Bryant |
| 6,119,694 | A | 9/2000 | Correa |
| 6,123,077 | A | 9/2000 | Bostock |
| 6,161,540 | A | 12/2000 | Fecteau |
| 6,394,090 | B1 | 5/2002 | Chen |
| 6,797,352 | B2 | 9/2004 | Fowler |
| 6,910,288 | B2 | 6/2005 | Dua |
| 7,171,967 | B2 | 2/2007 | Brunell |
| 7,188,620 | B2 | 3/2007 | Amarasinghe |
| 7,191,720 | B2 | 3/2007 | Thomas |
| 7,240,371 | B2 | 7/2007 | Liu |
| 7,562,658 | B2 | 7/2009 | Madaus |
| 7,695,579 | B2 | 4/2010 | Kramer |
| 7,854,022 | B2 | 12/2010 | Warren |
| 7,971,590 | B2 | 7/2011 | Frater |
| 8,172,970 | B2 | 5/2012 | Sussmann |
| 8,196,583 | B2 | 6/2012 | Radney |
| 8,312,883 | B2 | 11/2012 | Gunaratnam |
| 8,402,676 | B2 | 3/2013 | Hasso |
| 8,561,613 | B2 | 10/2013 | Brambilla |
| 8,678,002 | B2 | 3/2014 | Stewart |
| 8,765,257 | B2 | 7/2014 | Weedlun |
| 8,950,404 | B2 | 2/2015 | Formica |
| 8,997,742 | B2 | 4/2015 | Moore |
| 9,480,809 | B2 | 11/2016 | Guney |
| 9,770,611 | B2 | 9/2017 | Facer |
| 9,974,915 | B2 | 5/2018 | Haskard |
| 10,104,925 | B2 | 10/2018 | Farmer |
| 10,265,492 | B2 | 4/2019 | Amarasinghe |
| 10,279,138 | B2 | 5/2019 | Ovzinsky |
| 10,569,044 | B2 | 2/2020 | Dunn |
| 10,987,478 | B2 | 4/2021 | Kwok |
| 11,020,558 | B2 | 6/2021 | Kwok |
| 2002/0148258 | A1 | 10/2002 | Cole |
| 2006/0201513 | A1 | 9/2006 | Chu |
| 2007/0235033 | A1 | 10/2007 | Reier |
| 2008/0271740 | A1 | 11/2008 | Gloag |
| 2009/0088037 | A1 | 4/2009 | Covelli |
| 2009/0155543 | A1 | 6/2009 | Fowler |
| 2009/0178680 | A1 | 7/2009 | Chang |
| 2009/0183739 | A1 | 7/2009 | Wondka |
| 2009/0277451 | A1 | 11/2009 | Weinberg |
| 2009/0283096 | A1 | 11/2009 | Cerbini |
| 2009/0320849 | A1 | 12/2009 | Biedermann |
| 2010/0000544 | A1 | 1/2010 | Blaszczykiewicz |
| 2011/0023883 | A1 | 2/2011 | Hieber |
| 2011/0131700 | A1 | 6/2011 | Tsui |
| 2013/0220327 | A1 | 8/2013 | Barlow |
| 2015/0289573 | A1 | 10/2015 | Haas |
| 2016/0038708 | A1 | 2/2016 | Amarasinghe |
| 2017/0065784 | A1* | 3/2017 | Mashal ............. A61M 16/0616 |
| 2017/0143928 | A1 | 5/2017 | Berthon-Jones |
| 2017/0182276 | A1 | 6/2017 | Hammer |
| 2017/0274167 | A1 | 9/2017 | Huddart |
| 2017/0281894 | A1 | 10/2017 | Walls |
| 2017/0312144 | A1 | 11/2017 | Moritani |
| 2018/0214655 | A1 | 8/2018 | Kooij |
| 2018/0250486 | A1 | 9/2018 | Amarasinghe |
| 2018/0263830 | A1 | 9/2018 | Uchida |
| 2019/0001095 | A1 | 1/2019 | Rose |
| 2019/0009045 | A1* | 1/2019 | Bernard ................... A61F 5/08 |
| 2020/0338294 | A1* | 10/2020 | McLauren ........... A62B 18/025 |
| 2021/0008317 | A1 | 1/2021 | Davidson |
| 2021/0038850 | A1 | 2/2021 | Gibson |
| 2021/0093822 | A1 | 4/2021 | Gilbert |
| 2021/0187232 | A1 | 6/2021 | Gibson |
| 2023/0073105 | A1* | 3/2023 | Tani ................... H04L 27/0002 |

FOREIGN PATENT DOCUMENTS

| | | | | |
|---|---|---|---|---|
| AU | 2014201197 | B2 | 12/2015 | |
| CA | 2597035 | C | 11/2013 | |
| CN | 2638769 | Y | 9/2004 | |
| CN | 2638771 | Y | 9/2004 | |
| CN | 1207070 | C | 6/2005 | |
| CN | 2862746 | Y | 1/2007 | |
| CN | 200951271 | Y | 9/2007 | |
| CN | 201052347 | Y | 4/2008 | |
| CN | 201057791 | Y | 5/2008 | |
| CN | 100575584 | C | 12/2009 | |
| DE | 1560055 | A1 | 5/1970 | |
| DE | 10258917 | B4 | 9/2007 | |
| EP | 0137094 | B1 | 7/1987 | |
| EP | 0281275 | B1 | 11/1994 | |
| EP | 2060294 | A1 | 5/2009 | |
| EP | 2165738 | B1 | 8/2011 | |
| EP | 3079745 | B1 | 12/2019 | |
| FR | 2541565 | A1 | 8/1984 | |
| FR | 2908050 | A1 | 5/2008 | |
| GB | 607072 | A | 8/1948 | |
| GB | 866890 | A | 5/1961 | |
| GB | 2532394 | A * | 5/2016 | ........ A61M 16/0616 |
| JP | 2000217940 | A | 8/2000 | |
| JP | 2001234416 | A | 8/2001 | |
| JP | 2002165895 | A | 6/2002 | |
| JP | 3625548 | B2 | 3/2005 | |
| JP | 3689821 | B2 | 8/2005 | |
| JP | 3704056 | B2 | 10/2005 | |
| JP | 3766815 | B2 | 4/2006 | |
| JP | 3125945 | U | 10/2006 | |
| JP | 2007000276 | A | 1/2007 | |
| JP | 2007159796 | A | 6/2007 | |
| JP | 4065882 | B2 | 3/2008 | |
| JP | 2008055035 | A | 3/2008 | |
| JP | 2008093285 | A | 4/2008 | |
| JP | 4270908 | B2 | 6/2009 | |
| JP | 4288619 | B2 | 7/2009 | |
| JP | 2009215201 | A | 9/2009 | |
| JP | 4717538 | B2 | 7/2011 | |
| JP | 4976916 | B2 | 7/2012 | |
| JP | 201751675 | A | 3/2017 | |
| KR | 100946200 | B1 | 3/2010 | |
| KR | 101030399 | B1 | 4/2011 | |
| NZ | 585295 | A | 12/2011 | |
| WO | 1990003744 | A1 | 4/1990 | |
| WO | 9108829 | A1 | 6/1991 | |
| WO | 9419976 | A1 | 9/1994 | |
| WO | 9854991 | A1 | 12/1998 | |
| WO | 2003057975 | A1 | 7/2003 | |
| WO | 2005122806 | A2 | 12/2005 | |
| WO | 2006019472 | A1 | 2/2006 | |
| WO | 2007010968 | A1 | 1/2007 | |
| WO | 2008030831 | A2 | 3/2008 | |
| WO | 2008134705 | A3 | 12/2008 | |
| WO | 2009092328 | A1 | 7/2009 | |
| WO | 2010131189 | A1 | 11/2010 | |
| WO | 2012073095 | A1 | 6/2012 | |
| WO | WO-2013026092 | A1 * | 2/2013 | ............. B29C 66/43 |
| WO | 2013064930 | A1 | 5/2013 | |
| WO | 2014025267 | A1 | 2/2014 | |
| WO | 2014175753 | A1 | 10/2014 | |
| WO | 2015057087 | A2 | 4/2015 | |
| WO | 2016059543 | A1 | 4/2016 | |
| WO | 2016060699 | A1 | 4/2016 | |
| WO | 2017158476 | A2 | 9/2017 | |
| WO | 2017168172 | A1 | 10/2017 | |
| WO | 2018007966 | A1 | 1/2018 | |
| WO | WO-2019235939 | A1 * | 12/2019 | ........ A61M 16/0683 |
| WO | 2020000033 | A1 | 1/2020 | |
| WO | WO-2020009589 | A1 * | 1/2020 | ........... A61M 16/06 |
| WO | 2020257878 | A1 | 12/2020 | |
| WO | WO-2020261138 | A1 * | 12/2020 | ........... A61M 16/16 |
| WO | WO-2022040760 | A1 * | 3/2022 | ............. A62B 23/02 |
| WO | WO-2023023770 | A1 * | 3/2023 | ........ A61M 16/0875 |

* cited by examiner

411

412

411

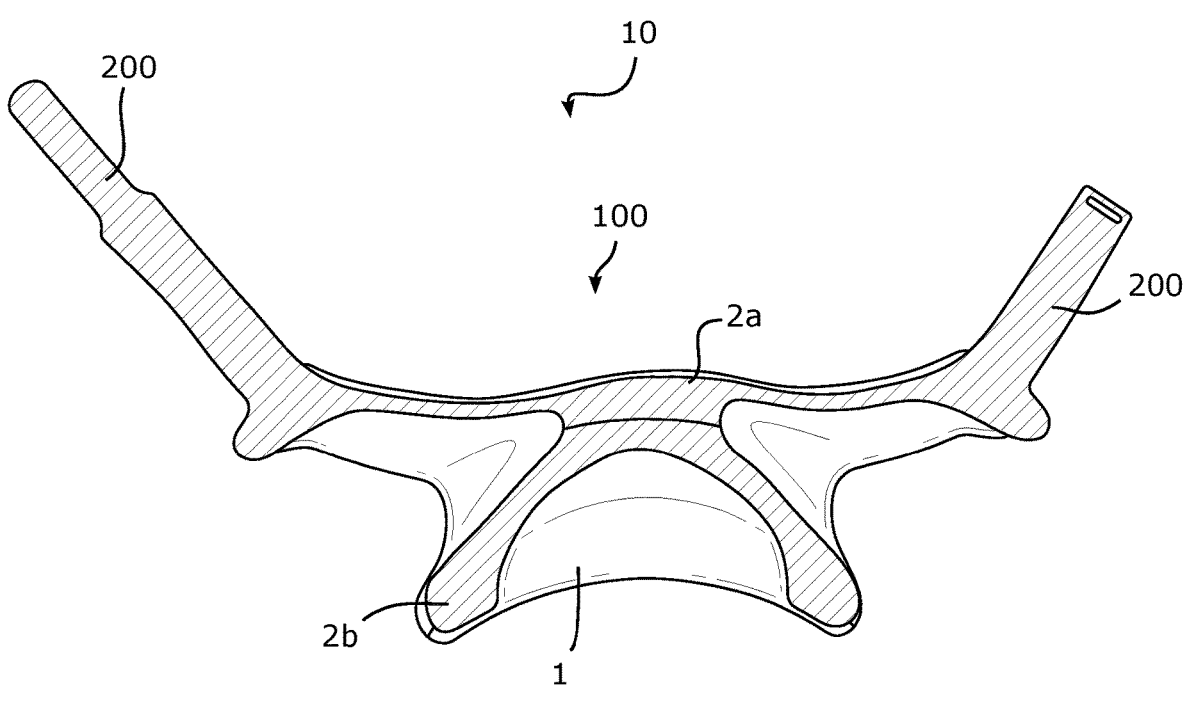
FIGURE 39B
FIGURE 39C
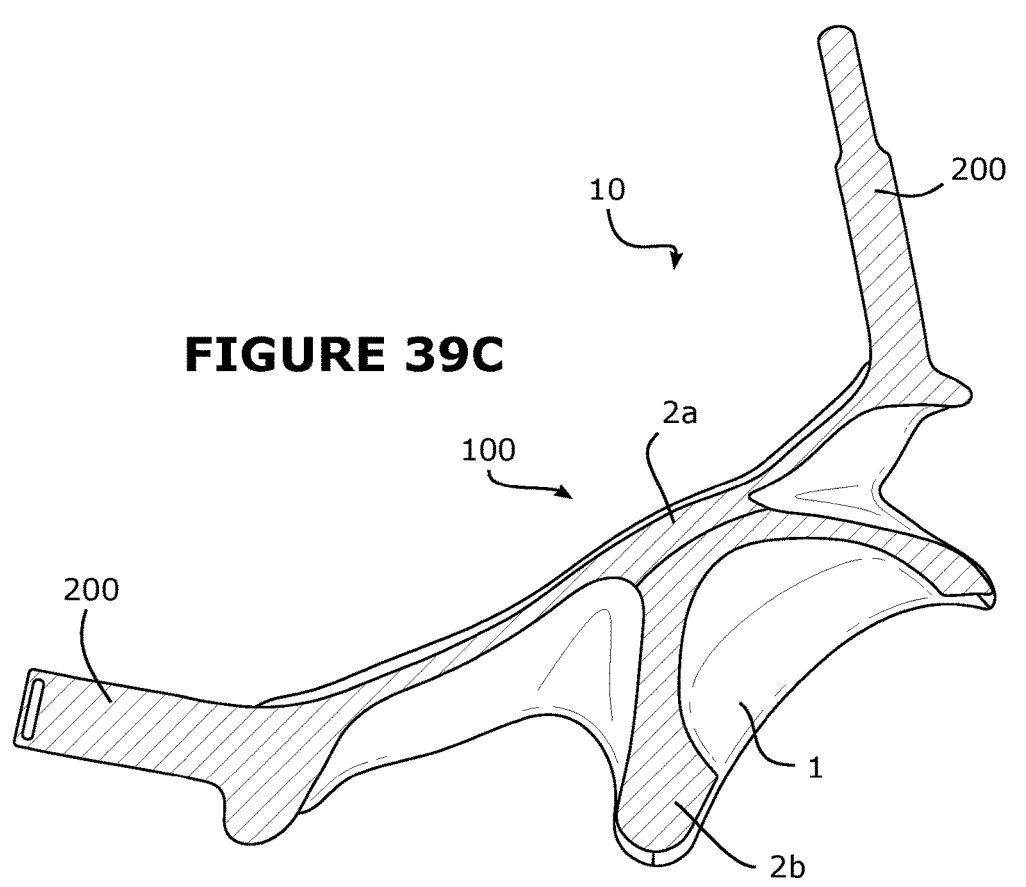

HEADGEAR FOR A PATIENT INTERFACE

FIELD OF THE INVENTION

The present invention relates to headgear for a patent interface.

BACKGROUND TO THE INVENTION

Respiratory interfaces or masks are used to provide respiratory gas or gases, such as air in CPAP therapy, including in for example VPAP and BiPAP systems, or NIV, or high flow rate therapy, for example.

A respiratory interface may comprise a nasal, oral, or full face, i.e., both nasal and oral, interface. In turn an interface may be an indirect interface which covers the nose, mouth, or both, or an indirect interface such as an interface comprising nasal nozzles or pillows or similar which enter into the nares of the wearer.

Headgear for a respiratory interface may comprise at least two side straps which in use extend from a rear part of the headgear along the left and right sides of the patient's head to connect to the interface. Other configurations may include two sets of an upper and a lower side strap of each side.

Headgear may also comprise a top strap such as a crown strap or a forehead strap, and respiratory headgear may be in various other forms. For example, headgear may comprise only a crown or forehead strap or an occipital loop, and a single strap on either side of the patient's head or face to the mask. Typically, the length of one or more of the headgear straps may be adjustable so that a patient can don the interface and headgear when the headgear strap or straps are loose and then tighten the straps when the interface and headgear are in position, to hold the mask and headgear securely in position thereafter until removal or doffing.

SUMMARY OF THE INVENTION

Patients may use various types of respiratory interfaces or masks for the provision of different respiratory therapies. To enable the respiratory therapy to be provided to the patient the interface must be retained in some way relative to either or both of the patient's mouth and nose. This is particularly the case where the respiratory therapy involves the provision of pressurised gases; the interface must be retained against the patient's face to provide at least some degree of a seal and prevent undesirable leakage of the respiratory therapy gases from the periphery of the interface. A headgear may be utilised to provide this function of retaining the interface on the patient's face.

Respiratory interfaces or masks may be used in a variety of settings, including in hospital environments and in patients' homes. Various respiratory therapies may be provided either or both when a patient is awake or while they sleep.

While a primary function of the headgear may be to retain the interface to the patient's face to counteract any pressure-generated forces and/or to create a seal with the patient's face, how the headgear transfers forces to the patient's head may significantly influence the patient's comfort and potentially also their compliance with the respiratory therapy. Load-carrying portions of the headgear may be liable to cause irritation or discomfort. This may particularly be the case where an interface and headgear are to be worn for an extended period of time, such as when sleeping.

Where an interface and headgear are used when sleeping at least some parts of the headgear may be positioned between the patient's head and the bed. This may present further opportunities for discomfort for the patient, as a localised thickness of the headgear may cause increased pressures to be experienced by their head when the headgear is laid on.

Different patients also may have significantly different anatomies. For example, they may have different circumferences of their heads, different face and skull shapes, and different tissue depths and sensitivities in different regions. This may be exemplified at the back of a patient's head, where some patients may have predominantly muscular necks or necks which taper significantly from their skulls, while other patients have more fat tissue or necks which do not taper as significantly from their skulls. These differences may result in different fits or comfort levels for a given headgear between different patients.

While a headgear may be adjusted in some ways to fit different patients, for example by shortening or lengthening one or more of the straps, such adjustments may not adequately compensate for the differences in anatomy between patients. Such adjustments may additionally or alternatively not provide for sufficient support or at least the sensation of support of the headgear on the patient's head. Ideally a headgear may be adjusted to comfortably suit the patient's anatomy, but also securely and snugly fit to the patient's head in the adjusted state.

A headgear itself may have particular and localised requirements for its structure and function. For example, to retain any given respiratory interface with some force, some regions of a headgear may experience greater loads than others. There may also be location specific needs for stiffness, flexibility, softness, any number of other properties.

Various aspects of the present disclosure provide a headgear comprising a plurality of panels, where at least part of each panel is lapped against at least part of another panel they are bonded together by an adhesive, and combinations of different panels having different properties and interfaces between panels having different lapping configurations provide for a headgear with the potential for location-specific features and properties.

The individual panels may according to at least some configurations be single plies or single layers of one material or a unitary composite of materials, as opposed to multiple layers of the same or different materials.

The use of an adhesive over other joining or bonding methods such as stitching or ultrasonic welding may provide for bonds between the panels of relatively decreased bulk or thickness or hardness (as compared to such other joining or bonding methods).

The use of adhesive over other joining or bonding methods may furthermore provide for tailoring of the structural and material properties at the bond. For example, an adhesive can be selected to have a substantially matching properties of the bonded panels (in particular stiffness, stretch and/or recoverability properties) such that the 'feel' of the bonded region of the panels is similar to that of the panels themselves. Advantageously, this will result in the patient of the headgear having increased comfort because they do not feel the joins between the panels when the headgear is on their head.

In other examples, an adhesive may be selected to provide different properties to the panels (such as stiffness, hardness and/or strength). In such examples, the adhesive may advantageously condition a selected portion of the panels to improve performance and/or resist undesirable deformation of the headgear in use.

Lapped regions may be fully or only partially bonded together, in particular by an adhesive. For example, a lapped region may include both bonded regions where the adjacent panel surfaces have been bonded together by an adhesive, and non-bonded regions where the adjacent panel surfaces are not bonded together with an adhesive.

Where lapped panels are bonded by an adhesive which substantially matches the properties of the lapped panels, there may be minimal or no difference in the properties, including particularly stretch properties, of the headgear at the bonded lapped region when compared to a non-bonded lapped region.

Otherwise, where the properties of the panels differ (for example where the lapped panels are extensible in perpendicular directions) or where the properties of the adhesive do not substantially match that of the lapped panels there may be a difference in the properties, particularly stretch properties, of the headgear at the bonded lapped region compared to a non-bonded lapped region.

In addition to providing a desired performance of the headgear, adhesive may be utilised to provide different properties to the panels to change the 'feel' or appearance of the headgear. This may be employed to provide cues to the patient or other user as to orientation or use of the headgear.

The panels of headgear according to the disclosure may be entirely bonded together using one or more adhesives.

However, it will be appreciated that various embodiments may utilise one or more additional methods of bonding various panels or panel parts or other components together to form the headgear to some degree. For example, various panels or panel parts may include stitched joins, particularly at locations where such stitching may not undesirably impact on the bulk of the headgear or particularly thickness of the joins and comfort of the patient when wearing the headgear.

Conventional headgear is commonly constructed from one or more joined sections of a laminate comprising external fabric layers which sandwich an internal foam layer, such as a natural or synthetic rubber foam. An example of such a laminate material which is used in the construction of headgear is Breathe-o-Prene®. Where a headgear is made from a joined sections of an existing laminate material such as Breathe-o-Prene® the headgear will have a thickness of at least the three or more layers of the laminate. At joins between sections of the laminate the headgear will have the thickness of both joined sections. Even if efforts are made to reduce the thickness of the layers of each laminate, overlapping laminate sections can easily create undesirably thick regions and thus potential sources of discomfort for a wearer of the headgear. For example, where the laminates have three layers each, the resulting join will have a thickness of the total combined six layers.

According to the present disclosure a headgear may be formed by a plurality of single-ply panels where at least part of each single-ply panel is lapped against at least part of another single-ply panel, and the lapped panels are each bonded together. This may provide a headgear having a number of lapped regions where two or more panels lap each other, and a number of non-lapped regions where panels are not lapped by another panel. At the non-lapped regions the headgear will comprise only a single-ply panel.

At one or more of the lapped regions the panels may be joined to each other to secure the panels together and define the headgear.

The panels may be cut to their respective desired shapes, then lapped with each other and joined together. Such a configuration may differ from conventional methods such as in the case of a laminate material such as Breathe-o-Prene® where a headgear is built up by cutting already laminated panel sections, which are then joined together to form the headgear or parts of the headgear.

While the panels of the headgear may be cut to shape before they are lapped together and joined, in some forms at least some parts of the headgear may additionally or alternatively be cut once they are lapped together and potentially once one or more lapped parts are joined together.

Because the headgear of the disclosure may be formed from individual panels comprising single plies of one material or one composite of materials, rather than from joined laminates of multiple layers of different materials, the headgear may have reduced thickness. At non-lapped regions the headgear comprises only the thickness of one single-ply panel, rather than at least three plies as in the case of the use of a three-layer laminate material such as Breathe-o-Prene®. This may allow for a relative reduction in thickness.

Similarly at lapped regions the headgear of the present disclosure may also have a reduced thickness, as a lapped region may have a thickness of only two panels compared to six panels in the case of a joint of two three-layer laminate materials such as Breathe-o-Prene®.

The potential reduction in the number of panels and thickness at both lapped regions and non-lapped regions of the headgear of the present disclosure when compared to a conventional headgear made from joined laminate or multiply materials may provide either location-specific or overall reductions in the thickness of the headgear. Reduced thicknesses, whether in particular locations or across the whole headgear, may provide a visual and/or physical perceptions to a patient of reduced bulk. Reduced thicknesses may also provide increased comfort for a patient wearing the headgear.

Any such reduction in the number of panels present at different points of the headgear and its thickness may provide corresponding decreases in the overall weight of the headgear.

Joining panels together by way of an adhesive may also provide for either or both of reductions in thickness and weight, as the use of an adhesive may obviate the need for providing complex hems with stitching or welding.

According to another aspect, the present disclosure provides a headgear comprising a plurality of panels, where at least part of each panel is lapped against at least part of another panel they are bonded together to provide a thin and seamless or substantially seamless headgear.

According to another aspect, the present disclosure provides a headgear comprising a plurality of panels, where at least part of each panel is lapped against at least part of another panel they are bonded together to provide a lightweight headgear.

According to another aspect, the present disclosure provides a headgear comprising a plurality of panels, where at least part of each panel is lapped against at least part of another panel they are bonded together, wherein the panels are configured such that the headgear retains at least some of its in-use shape when in an at-rest state.

According to another aspect, the present disclosure provides a headgear consisting only of a plurality of panels that are bonded together using one or more adhesives.

According to another aspect, the present disclosure provides a headgear consisting only of a plurality of panels that are bonded together using only a single adhesive.

According to another aspect, the present disclosure provides a headgear for a patient interface, the headgear comprising a plurality of panels, each panel having two opposed major faces, wherein the headgear has at least one lapped region in which at least two of the plurality of panels respectively overlap and underlap each other, and at least one non-lapped region in which one or more of the plurality of panels is not lapped by another of the plurality of panels, and wherein at the or each at least one lapped region the panels are bonded to each other by an adhesive.

The headgear comprises a plurality of lapped regions and a plurality of non-lapped regions.

Each of the plurality of panels are provided at least partially within one or more of the plurality of lapped regions.

At least some of the plurality of panels are also provided at least partially within one or more of the plurality of non-lapped regions.

Each of the plurality of panels are also provided at least partially within one or more of the plurality of non-lapped regions.

A lapped region comprises a substantially continuous region of two or more lapping panels.

A non-lapped region comprises a substantially continuous region of one non-lapped panel.

In at least one of the plurality of lapped regions one or more of:

a first panel and a second panel lap each other, a first panel is lapped on respective sides between a second panel and a third panel, and more than three panels, comprising at least a first panel, a second panel, a third panel, and a fourth panel, are consecutively lapped against each other.

Each panel of the plurality of panels at the lapped region is bonded to the one or both adjacent panels by an adhesive.

At least one of the plurality of panels comprises a different material to that of another panel of the plurality of panels.

At least one of the panels at a lapped region comprises a different material to that of another panel at a lapped region.

The first panel comprises a different material to that of the second panel.

The second and third panels comprise the same material, which is a different material to that of the first panel.

Different materials comprise one or more of a different texture, softness, stiffness or flexibility, stretch properties, density, thickness, colour, frictional coefficient in relation to a reference material, breathability, or degree of transparency or sheer.

Different materials comprise one or more of a directionally different: texture, softness, stiffness or flexibility, stretch property including extensibility and/or recoverability or in particular elasticity, or frictional coefficient in relation to a reference material.

The two opposed major faces of at least one panel of the plurality of panels comprises one or more of a different texture, frictional coefficient, or colour of the opposed major faces of the panel.

Exposed portions of major faces of the plurality of panels define an internal surface and an external surface of the headgear relative to the head of a patient in use, and wherein at least some of the plurality of panels each define part of the internal surface and/or the external surface of the headgear.

The at least some of the plurality of panels comprise one or more of a different texture, softness, colour, or frictional coefficient in relation to a reference material.

The at least some of the panels defining part of the internal surface of the headgear comprise a greater surface softness than that of at least some of the panels defining part of the external surface of the headgear.

Only some of the plurality of panels define the internal surface and only some of the plurality of panels define the external surface.

Excluding the or each at least one non-lapped region, an exposed portion of a panel either defines part of one or the other of the internal surface and external surface.

The plurality of panels comprise a panel of first stretch material and a panel of second stretch material, where the stretchability of the first stretch material and the second stretch material are different.

The first stretch material is more stretchable than the second stretch material.

The plurality of panels comprise at least one elasticated fabric panel and at least one non-elasticated fabric panel.

The plurality of panels comprise:

a rear portion for location at the rear of the head of a patient, a crown strap, and at least two side straps for attachment to the patient interface.

The rear portion transfers loads between the at least two side straps, and the rear portion comprises at least one panel of a first material which laps a portion of a side strap panel of each of the at least two side straps.

The rear portion comprises a plurality of panels of the first material, and each of the at least two side straps are lapped on respective sides by panels of the first material.

An extent of the rear portion to be located lowest on the rear of the head of a user comprises a lower panel of a second material.

The second material is non-unravelable material.

The lower panel is lapped to or between one or more of the plurality of panels of the first material.

The lower panel of the second material is more stretchable than the plurality of panels of the first material.

The lower panel of the first material is a stretch panel and the plurality of panels of the first material are non-stretch panels.

The lower panel of the second material is elasticised, and the plurality of panels of the first material are non-elasticised.

The lower panel of the second material has a greater elasticity than the plurality of panels of the first material.

The second material is an elastic material, and first material is a substantially inelastic material.

A portion of the lower panel is in a non-lapped region of the headgear, and the portion of the lower panel is substantially crescent-shaped.

At least a portion of the lower panel within a non-lapped region of the headgear is substantially crescent-shaped, having a concave edge and a convex edge, and wherein the concave edge forms at least a portion of a lower peripheral edge of the rear portion.

The rear portion comprises an upper edge panel, the upper edge panel forming at least a portion of an upper peripheral edge of the rear portion, the upper edge panel comprising a material that is thinner and/or softer than that of a panel to which it is lapped.

The upper edge panel is lapped to another panel at the rear portion so as to define an internal surface, relative to the head of a patient in use, of the headgear at an upper region of the rear portion.

The upper edge panel is provided within both a lapped region and a non-lapped region, and wherein the non-lapped region forms at least part of an upper peripheral edge of the rear portion.

The upper edge panel at the non-lapped region is configured, in use and towards the upper peripheral edge of the rear portion, to roll away from the head of the patient.

The upper edge panel at the non-lapped region extends away from an adjacent lapped region a distance of about 5 times to about 20 times the thickness of the upper edge panel.

The crown strap defines an internal surface oriented towards the head of the patient in use and an external surface oriented away from the head of the patient in use, and wherein the internal surface has a greater softness than that of the external surface.

The crown strap depends from the rear portion.

The crown strap depends from the rear portion and at least one side strap of each lateral side of the rear portion and/or crown strap.

The crown strap has a width greater than that of the at least two side straps.

The crown strap is of a different colour to that of the at least two side straps.

The crown strap comprises a pair of crown strap portions which are adjustably fixable to each other to provide a variable-length crown strap, each crown strap portion comprising an internal crown strap portion panel and an external crown strap portion panel adhesively bonded to each other.

The internal crown strap portion panels have a greater softness than that of the external crown strap portion panels.

The internal and external crown strap portion panels respectively overlap and underlap the panel or panels of the rear portion and/or side straps to which they are lapped.

The crown strap is relatively stiffer and/or denser than the rear portion.

The crown strap comprises one or more panels of a material having a greater stiffness and/or greater density than that of one or more panels comprising the rear portion.

The at least two side straps comprise two lateral sets of an upper and a lower side strap, each set of side straps for connection to corresponding sides of the patient interface.

The two upper side straps comprise a unitary panel which extends across the rear portion of the headgear.

The unitary panel is provided within a lapped region across at least part of the rear portion of the headgear and within a pair of distal non-lapped regions.

An upper and lower side strap comprise a unitary panel, the unitary panel configured to extend around a rear of the ear of a patient.

A lapped region of the upper side straps is respectively overlapped and underlapped by panels of the crown strap.

The lower side straps are overlapped and underlapped by a plurality of panels of the rear portion.

An ear loop for passing behind the ear of a patient defines a lateral peripheral edge of the rear portion between each lateral set of upper and lower side straps.

The edge profile of each ear loop comprises a pair of straight-line portions.

The pair of straight-line portions form a V-shape, the tip of each V directed towards the other and into the rear portion of the headgear.

The two upper side straps comprise two respective panels, each provided within a lapping region at the rear portion of the headgear and within distal non-lapping regions.

Each of the two respective panels of the two upper side straps are overlapped and underlapped by panels of the rear portion of the headgear.

Terminal portions of either or both of the upper and lower side straps include gripping tabs comprising a first and second tab panels, the tab panels respectively overlapping and underlapping the terminal portion at a first tab region and lapping each other at a more distal second tab region.

The first and second tab panels are of a material that is one or more of thinner, softer, of a different colour, or has a lower coefficient of friction with respect to a reference material than that of the material of the respective straps of the sets of upper and lower side straps.

The first and second tab panels are of a plastics material that is one or more of thinner, harder, stiffer, of a different colour, or has a lower coefficient of friction with respect to a reference material than that of the material of the respective straps of the sets of upper and lower side straps.

The headgear at the second more distal tab region is of greater stiffness than the headgear at the first tab region.

The second more distal tab region is thinner than one or more of the upper and lower side straps at a non-lapped region.

The gripping tabs further comprise at one external surface a first half of a hook and loop fastener.

The side straps are configured such that the strap surface which corresponds to the first half of the hook and loop fastener, when the strap is folded back on itself, comprises a second half of the hook and loop fastener.

The at least two side straps comprise a left and right side straps, each side strap for connection to a corresponding side of the patient interface.

Each side strap of the set of side straps is configured to fold back onto and attach to itself to define a connection loop by which the patient interface may be retained.

Each side strap of the set of side straps comprises a series of visual features along at least one surface of the side strap, the visual features for indicating adjustment points to the patient when folding a side strap back onto itself.

The visual features are regularly spaced along the surface of each side strap.

Each side strap of the set of side straps comprises a series of tactile features along at least one surface of the side strap, the tactile features for providing a tactile feedback to a patient of different adjustment conditions of the respective strap.

The series of tactile features provide for indexing of the adjustment of each respective side strap.

An interaction of the tactile features with the patent interface provide the tactile feedback to the patient.

Each side strap comprises a strap panel, the strap panel lapped on at least one major face with a tactile feedback panel, wherein the tactile feedback panel is one or more of thinner, harder, and stiffer than the strap panel which it laps and wherein the tactile feedback panel and the strap panel are bonded by an adhesive.

The tactile feedback panel comprises the tactile features, the tactile features provided by a series of voids through the tactile feedback panel.

The series of voids present the tactile feedback panel as having a series of ridges relative to the strap panel to which it is lapped.

The tactile feedback panel is harder and/or stiffer than the strap panel, and the series of ridges are for mechanically engaging with a buckle of the patent interface.

Each respective lateral extent of the crown strap and rear portion non-lappingly interface with each other and an end of a respective one of the side straps.

Each respective lateral extent of the crown strap and rear portion and end of the respective side strap interface with each other in an edge-to-edge configuration.

Each respective lateral extent of the crown strap and rear portion and end of the respective side strap are lapped on at least one set of major faces by a joint panel.

At least one major face of one or more of the crown strap, rear portion, and side straps is lapped along at least a portion towards their peripheries with a stiffening panel.

The stiffening panel comprises a stretch material which is less stretchable than the respective one or more of the crown strap, rear portion, and side straps.

The stiffening panel comprises a non-stretch material.

The stiffening panel comprises a substantially inextensible material.

The stiffening panel comprises a non-elasticated material.

At least a portion of at least one major face of one or more of the crown strap, rear portion, and side straps, is treated with a conditioner.

The conditioner is provided at least towards an edge of the at least a portion of the at least one major face of one or more of the crown strap, rear portion, and side straps.

The crown strap comprises a single unitary strap.

The rear portion comprises a single unitary strap.

The crown strap and rear portion comprise a closed loop.

The set of side straps depend from intersections of the crown strap and rear portion.

The intersections of the crown strap and the rear portion are, in use, located above the ear of a patient.

One or more of the set of side straps, the rear portion, and the crown strap comprise at least in part a first stretch panel which is overlapped and underlapped by a pair of second stretch panels, where the first stretch panel is more stretchable than the second stretch panels.

One or more of the set of side straps, the rear portion, and the crown strap comprise at least in part a relatively elastic panel which is overlapped and underlapped by respective relatively inelastic panels.

An entirety of one or both of the crown strap and rear portion comprise a first stretch panel which is overlapped and underlapped by a pair of second stretch panels, where the first stretch panel is more stretchable than the second stretch panels.

An entirety of one or both of the crown strap and rear portion comprise a relatively elastic panel which is overlapped and underlapped by respective relatively inelastic panels.

The rear portion and crown strap form a closed loop, and the rear portion and crown strap together comprise a relatively greater stretch panel and a relatively lesser stretch panel.

The rear portion and crown strap form a closed loop, and the rear portion and crown strap together comprise an elasticated panel and at least one non-elasticated panel.

The rear portion and crown strap comprise two relatively lesser stretch panels, the two relatively lesser stretch panels each at a respective first end are lapped with a relatively greater stretch panel and at the other ends are lapped with each other.

The rear portion and crown strap comprise two non-elasticated panels, the two non-elasticated panels each at a respective first end lapped with an elasticated panel and at the other ends lapped with each other.

The rear portion and crown portion comprise a single relatively lesser stretch panel, the single relatively lesser stretch panel lapped at two lateral ends to one or more relatively greater stretch panels.

The rear portion and crown portion comprise a single non-elasticated panel, the single non-elasticated panel lapped at two lateral ends to the panel of a substantially elasticated material.

The side straps depend from the closed loop of the crown strap and rear portion, and the closed loop at the side straps comprises a locally increased panel or combined panel width.

Terminal portions of either or both of the upper and lower side straps include gripping tabs comprising a first and second tab panels, the tab panels respectively overlapping and underlapping the terminal portion at a first tab region and lapping each other at a more distal second tab region.

The first and second tab panels are of a material that is one or more of thinner, softer, of a different colour, or has a lower coefficient of friction than that of the material of the respective straps of the sets of upper and lower side straps.

The headgear at the second more distal tab region is of greater stiffness than the headgear at the first tab region.

The gripping tabs further comprise at one external surface a first half of a hook and loop fastener.

The side straps are configured such that the strap surface which corresponds to the first half of the hook and loop fastener, when the strap is folded back on itself, comprises a second half of the hook and loop fastener.

At one or more lapped regions the headgear is at least partially one or both of overlapped and underlapped by an adhesive.

The adhesive comprises a hot-melt adhesive.

The adhesive is provided in a sheet or film-like form.

The adhesive is adhered to or adheres adjacent panels upon the application of heat, or heat and pressure, to the adhesive.

One or more of the plurality of panels comprise an unravelable material.

At least part of an edge of the headgear is treated by a conditioner.

An edge portion which is treated by the conditioner comprises increased fray resistance relative to a non-adhesive lapped edge portion of the same material.

At least part of an edge of the headgear is rolled back onto itself.

An adhesive is provided between the rolled-back portion and the portion onto which it is rolled back.

At least part of an edge of the headgear comprises an edge softening panel, a portion of which is lapped to a more interior panel, and wherein the edge panel comprises a material that is thinner and/or softer than that of the more interior panel to which it is lapped.

The edge panel is lapped to the more interior panel such that the edge panel defines an internal surface, relative to the head of a patient in use, of the headgear.

The edge panel is configured, in use and towards its outer end, to roll away from the head of the patient.

The edge panel at the non-lapped region extends away from an adjacent lapped region a distance of about 5 times to about 20 times the thickness of the more interior panel to which it is lapped.

The headgear has a weight of less than about 30 g.

The headgear has a weight of less than about 20 g.

The headgear has a weight of less than about 10 g.

The headgear has a weight of about 15 g to about 30 g.

The headgear has a weight of about 17.5 to about 27.5 g.

The headgear has a weight of about 25 g.

One or more of the plurality of panels comprise planar panels.

One or more of the plurality of panels comprise tubular panels.

According to another aspect, the present disclosure provides a headgear for a patient interface, the headgear comprising a first panel and a second panel which are lapped with each other and joined together, wherein the first panel comprises at least one darted portion which causes the headgear to assume a 3D shape.

One or more of the at least one darted portions of the first panel are covered at one major face of the first panel by the second panel.

One or more of the at least one darted portions are secured closed by a joining of the first panel and second panel together.

One or more of the at least one darted portions is provided at or towards a rear portion of the headgear and forms the headgear into a concave shape at a patient-facing side thereof.

According to another aspect, the present disclosure provides a headgear for a patient interface, the headgear comprising a plurality of panels which are lapped with each other, wherein two edges of a panel or respective panels are mated together so as to cause the headgear to define a 3D shape.

The panel or panels having the two edges are lapped by another panel at the edges.

The another panel retains the edges together by a joining of the panel or panels and the another panel at their lapped parts.

The two edges are located at or towards a rear portion of the headgear and when mated together form the headgear into a concave shape at a patient-facing side thereof.

More than two edges of a panel or respective panels are mated together.

More than two pairs of edges of a panel or panels are respectively mated together.

According to another aspect, the present disclosure provides a headgear for a patient interface, the headgear comprising a plurality panels which are lapped with each other and bonded together such that the headgear defines a 3D shape.

The headgear defines a concave shape at a patient-facing side of a rear portion of the headgear.

The panels are joined by bonding.

The bonding is by an adhesive.

The panels are joined by welding.

While the headgear is generally referred to in the context of a patient, it will be understood that the term patient may as appropriate be substituted for an assistant to the patient or a medical professional or otherwise anyone else who may use or interact with the headgear, whether for their own use or in association with aiding someone else's use of the headgear.

As used herein the term "and/or" means "and" or "or", or both.

As used herein "(s)" following a noun means the plural and/or singular forms of the noun.

For the purposes of this specification, the term "plastic" shall be construed to mean a general term for a wide range of synthetic or semisynthetic polymerization products, and generally consisting of a hydrocarbon-based polymer.

For the purpose of this specification, where method steps are described in sequence, the sequence does not necessarily mean that the steps are to be chronologically ordered in that sequence, unless there is no other logical manner of interpreting the sequence.

The term "comprising" as used in the specification and claims means "consisting at least in part of." When interpreting each statement in this specification that includes the term "comprising," features other than that or those prefaced by the term may also be present. Related terms "comprise" and "comprises" are to be interpreted in the same manner.

Other aspects of the invention may become apparent from the following description which is given by way of example only and with reference to the accompanying drawings.

BRIEF DESCRIPTION OF THE DRAWINGS

The patent or application file contains at least one drawing executed in colour. Copies of this patent or patent application publication with colour drawing(s) will be provided by the Office upon request and payment of the necessary fee.

Preferred embodiments of the invention will be described by way of example only and with reference to the drawings, in which:

FIG. 39B shows the panels of FIG. 39A when lapped together.

FIG. 39C shows another view of the lapped panels of FIG. 39B.

DETAILED DESCRIPTION OF PREFERRED EMBODIMENTS

Figure 1A:
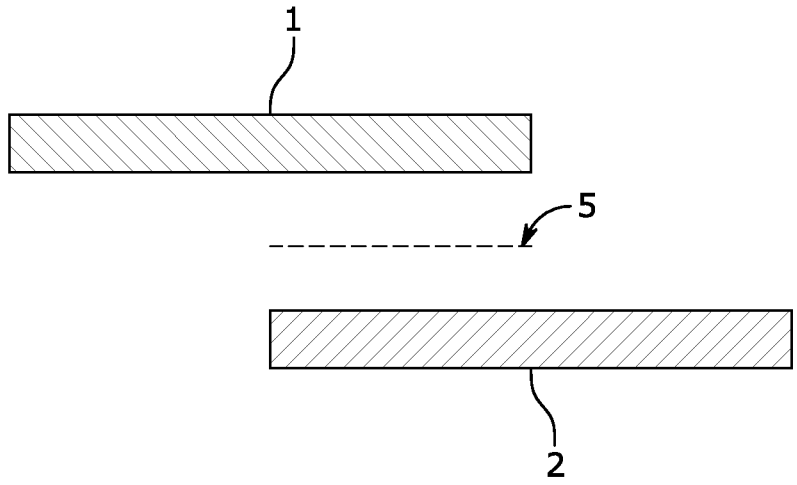
FIGS. 1A and 1B are cross-sectional views of, respectively, a pre-lamination and a laminated configuration of two panels.

Described herein are various embodiments of a headgear for a respiratory interface. Such a headgear may include a plurality of panels, configured to present the headgear with at least one lapped region in which at least two of the plurality of panels overlap and underlap each other, and at least one non-lapped region in which one or more of the panels are not lapped by another of the panels. Each of the panels at the one or more lapped regions are bonded to each other by an adhesive.

In a simplest form, the headgear may comprise only two panels at least one of which is partially lapped to the other, to form a lapped region where they respectively overlap and underlap, and one or two non-lapped regions where one or both panels exist without being lapped.

In various other forms, the headgear may comprise additional panels in either fully or partially lapping relationships with one or more of the other panels. By such a configuration of variously lapped panels a laminated headgear may be built up.

At least a portion of the headgear may be formed by such a configuration of lapped panels.

In some embodiments, at least a main part, or even an entirety or a substantial entirety of the headgear may be formed by a plurality of panels in various lapped configurations.

According to some embodiments a headgear may consist only of a plurality of panels, to provide a headgear with at least one lapped region and at least one non-lapped region.

According to some embodiments a headgear may consist only of a plurality of panels that are bonded together using adhesive.

In other words, the headgear may consist of a plurality of panels that have been joined without the use of stitching or welding.

Because adhesive forms a very thin layer, the bulk of the headgear is reduced relative to headgear in which panels are stitched or welded together. Also, the material properties of the adhesive can be selected so that lapped region is relatively soft and flexible compared to a stitched or welded join.

The panels of the plurality of panels may be selected from any suitable panel-like material. This may include textiles being networks of natural and/or artificial fibres, and more particularly fabrics as may be made by weaving, knitting, spreading, crocheting, bonding, or other available methods.

It may also include any other non-conventionally textile materials which may be provided in a panel-like form, such as a plastic or composite.

The panels may be of a sheet-like form or may comprise tubular panels.

In at least some embodiments, some or all of the plurality of panels may be of flexible materials, and particularly materials which may drape under their own weight. Such materials may be particularly suited to forming parts of a headgear which is to conform to the shape of a patient's head.

Each panel of the plurality of panels that comprise the headgear defines two opposed major faces. In at least some embodiments it may be these major faces which are to be lapped against each other and bonded together within the one or more lapped regions of the headgear.

The plurality of panels may be panels of the same material.

In various preferred forms at least some of the panels may be of different materials. Such different materials may have at least some different material properties. Such properties may include the texture of the panel at one or both of its major faces, or at one or more of the edges bounding the two major faces. Another property may be the softness or hardness of one or both of the major faces or one or more of the edges bounding the two major faces. Another material property may include the stiffness or flexibility of the panel, or its stretch properties. Stretch properties may include extensibility, recoverability, and elasticity. Further properties which one or more of the panels may have include different densities, surface hardnesses, Young's moduli, thicknesses, colours at one or both of the major faces or bounding edges, coefficients of friction at one or both of the major faces relative to a reference material. The different material properties may also include different degrees of breathability, different degrees of hydrophobic or hydroscopic qualities, different permeability, or different transparencies or sheers.

In addition to having any of such different material properties between panels, an individual panel itself may have one or more of such characteristics which are directionally different within the panel itself. For example, a panel may have a directionally different texture or softness. It may also have directionally different stiffness or flexibility, stretch properties, or frictional coefficients in relation to a reference material.

In addition to different material properties, different panels of the plurality of panels may have different physical configurations, including both thickness and lateral dimensions.

Another example of a panel characteristic of a textile panel may be whether it comprises a cut or uncut pile. Whether the pile is cut or uncut may provide different surface characteristics. For example, an uncut pile may present loops of material at a panel surface. Such a material with an uncut pile may generally be known as an unbroken loop (UBL) material.

The presence of such loops may be desirable to act as the loop portion of a hook and loop fastener system. By this configuration a hook and loop fastener system may be provided without having to attach any additional loop-providing component to the panel. This may go at least some way to providing a headgear which is of reduced thickness.

The panels may further be selected of materials having any other material properties or panel configurations such as may provide for the desired functionality of a headgear which is to comprise the panels.

The stretch properties of a panel refer first to its in-plane extensibility or stretchability. This extensibility may be omnidirectional, such that the panel may have the same in-plane extensibility in all directions. The stretch properties of a panel may differ directionally, so the panel has either different extensibilities or is extensible and inextensible in different in-plane directions.

A stretch panel may be one that has at least some degree of in-plane extensibility or stretchability. A non-stretch panel may be relatively inextensible in-plane in at least one direction.

A non-stretch panel may be one that has a lesser degree of extensibility than a stretch panel.

The panels may have differing stretch properties from each other. For example, a first panel may have a first stretchability, while a second panel has a second different stretchability. Where the panels are lapped against each other but not bonded together they may define another third stretchability. Finally, where the panels are lapped and bonded they may define another fourth stretchability.

A panel which is extensible or stretchable may or may not be recoverable. In at least some preferred configurations the stretch properties of a stretch panel may include recoverability, so that a panel may be stretched then when the stretching load is removed it may return to or towards its original unstretched shape.

Recoverability may for example be achieved by elasticating a panel. An elasticated panel includes at least one elastomeric, rubber, or rubberised component. For example, an elasticated panel may include at least some fibres of such an elastic material. Conversely, a non-elasticated panel is a panel which does not include any such an elastomeric, rubber, or rubberised component. An elasticated panel has greater elasticity, due to the at least one elasticated component, than a non-elasticated panel of the same material but without the at least one elasticated component.

In addition to different physical characteristics provided by the properties of different individual panels, composite characteristics may be provided by the bonding together of two or more lapped panels at the one or more lapped regions of the headgear. The properties of the two or more lapped panels, and in some configurations the properties of the adhesive which bonds them together, may provide for different properties of that lapped region of the headgear.

For example, the respective panel thicknesses will form a lapped region of a greater total thickness.

In another example, one panel at a lapped region is extensible in one direction, and another panel at the lapped region is extensible in another direction which is different or potentially perpendicular to the direction of the former panel. Particularly where the panels are extensible only in directions which are perpendicular or substantially perpendicular to each other, a functionality may be provided where the panels at the non-lapped regions may stretch in their respective directions, but at the lapped region may be substantially inextensible.

In another example, one panel at a lapped region is elasticised in one direction, and another panel at the lapped region is elasticised in another direction which is different or potentially perpendicular to the direction of the former panel. Particularly where the elasticised directions are perpendicular or substantially perpendicular, each panel at a non-lapped region may be able to be stretched along the elasticised direction, while at the lapped region the lapped panels may provide for a substantially non-elasticated overall characteristic.

Panels to be utilised in the headgear may be unravelable, meaning that their constituent fibres may be unravelled.

Panels to be utilised in the headgear may not be able to be unravelled, what may be known as a free-cut material. Such a material may be cut and may not or may at least be resistant to unravelling of the constituent fibres along the cut edge. Advantageously, such materials can be cut to shape with the cut edge of the panel forming an edge of the headgear without the need for further processing.

It will be appreciated that numerous other such combinations of panels having one or more different material properties may be configured so as to have desired properties both at non-lapped regions and lapped regions.

In addition to the use of panels having one or more different material properties, the characteristics of the headgear may be at least in part determined by different configurations of respectively lapped panels at the one or more lapped regions of the headgear.

Further details of various lapped and non-lapped regions and their associated panel configurations will now be described with relation to FIGS. 1A to 14B which illustrate various example forms and configurations of lapped and non-lapped regions.

Figure 1B:
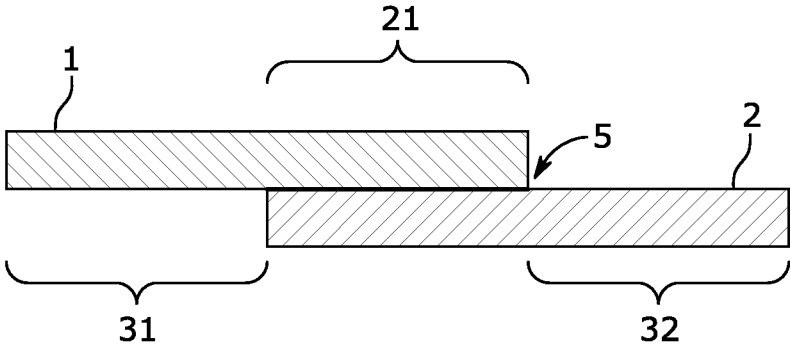

FIGS. 1A and 1B are sectional views of one such lapped region in respectively a pre-lamination exploded configuration showing the constituent components before they are bonded, and a post-lamination configuration where the panels have been bonded together.

As seen in FIG. 1A there is a first panel 1 and a second panel 2. The first panel 1 and second panel 2 may be of the same or different materials. An adhesive 5 (such as will be described in further detail subsequently) is illustrated to be provided between the first panel 1 and second panel 2 at the region where they are to respectively overlap and underlap each other.

While shown as provided across a substantial entirety of the overlapping and underlapping portion of the first panel 1 and second panel 2, the adhesive 5 may be provided at only a part or parts of the lapped region, either or both across and/or into the into the page of the sectional view of FIG. 1A.

FIG. 1B shows the panels and adhesive of FIG. 1A when bonded together to form a single laminate. The combined panels define a first non-lapped region 31 of the headgear at the portion where the first panel 1 is not lapped, a first lapped region 21 where the first panel 1 and second panel 2 lap each other, and a second non-lapped region 32 of the headgear at the portion where the second panel 2 is not lapped.

While illustrated in FIGS. 1A and 1B as being panels of the same material and configuration, it will be appreciated that the panels of the lapping configuration of FIGS. 1A and 1B, and any of the subsequently described configurations including of FIGS. 2A-14B, may include panels which are of different materials or configurations, such as is herein described.

It will be appreciated that any of the panels shown in illustrated sectional views of FIGS. 1A-14B may be of different lateral dimensions at the cross-section than are illustrated, and/or may be of different planar (either across or into/out of the page) dimensions at different parts of each respective panel. For example, one or both of the first panel 1 and second panel 2 of FIGS. 1A and 1B may be of greater dimensions across the page, such that one or both of the non-lapped regions 31 and 32 and/or the lapped region 21 may be of greater lateral size across the page than illustrated. The cross-sectional panel configurations shown may also extend in a direction into or out of the page in the same configuration as seen in the cross-sectional view, or one or more panels may vary in configuration in either direction.

In a first example the first panel 1 and second panel 2 of FIGS. 1A and 1B may extend in directions into and/or out of the page in substantially the same configuration, so as to provide a lapped region 21 extending in directions into and/or out of the page and corresponding non-lapped regions 31 and 32 similarly extending in directions into and/or out of the page.

In a second example the first panel 1 of FIGS. 1A and 1B may extend in a direction into the page, but terminate in a direction out of the page, while the second panel 2 extends in a direction both into and out of the page. Such a configuration would provide the part of the second panel 2 in the direction out of the page to comprise another non-lapped region.

In a third example the first panel 1 of FIGS. 1A and 1B may narrow in a lateral dimension along a length in a direction either into or out of the page, such that the non-lapped region 31 may narrow and eventually cease to exist.

It will be appreciated that the corresponding differences in the shown cross-sectional views or other parts of the panels not seen in the cross-sectional views may be made with one or more of the panels of any of FIGS. 1A-14B.

At least adjacent panels are to be joined to each other at a lapped region. As previously described, this may be by bonding through the use of an adhesive. Such an adhesive is illustrated by the adhesive 5 as seen in FIGS. 1A and 1B. This adhesive may be in the form of a solid, semi-solid, liquid, or gel adhesive which is applied to one or both of the panels.

The adhesive will be understood to encompass any one or more commonly available types or combinations of adhesives. The adhesive may for example be an acrylic adhesive, an anaerobic adhesive, or a cyanoacrylate adhesive.

The adhesive may for example be an ester or ether-based compound. More specifically it may comprise nylon-polyamide, be nylon-polyamide, ester-polyurethane, polyester, or polyolefin.

Particularly where the adhesive is provided as a solid or semi-solid, but potentially also where it is a liquid or a gel, the adhesive may need to be activated to initiate or accelerate the process of curing the adhesive to form the bond between the lapped panels. For example, in the case of a solid or semi-solid adhesive the adhesive may be activated by melting from its solid or semi-solid state. In other forms the adhesive may be activated by the combination of two components of the adhesive, such as in the case of a two-component acrylic adhesive.

While the process of forming a bond by an adhesive will herein be referred to as a curing of the adhesive, it will be understood that such curing may include the forming of bonds by one or more of a chemical reaction within the adhesive or combination of adhesives, by the presence of a particular environment (such as anaerobic environment) or contact with a particular type of material (such as an alkaline material), by drying, or by an application of one or more of pressure, heat, sound, or light, or any other commonly utilised method to transform the adhesive into a bonded state.

In an example, the adhesive may be in the form of a solid or semi-solid hot-melt adhesive. Heat may be applied to activate the adhesive by melting it, and the adhesive may cure such as by one of the above-referenced curing processes in order to form the bond between the respective lapped panels.

As illustrated in FIG. 1A the adhesive 5 may be provided as a separate layer and assembled between the respective panels, where it may then be activated to create the bond.

Particularly where the adhesive is a liquid or gel adhesive, adhesive may be applied to a region of one or both of the lapped panels during the assembly of the panels.

Where the adhesive 5 is in the form of a hot-melt adhesive, it may be provided as a tape. This tape or sheet of adhesive may be able to be cut to form desired plane shapes to provide the desired bonded regions of panels.

Such a tape or sheet hot-melt adhesive may additionally comprise a sticky or adhesive surface or surface coating, such that the adhesive 5 may provide at least some provisional hold of the panels to which it is assembled before the adhesive is activated.

As illustrated in FIG. 1B, the first panel 1 and second panel 2 have been bonded to each other by the adhesive 5. The adhesive 5 may exist as a layer of bond material between the two panels, as illustrated in FIG. 1B. In other configurations, the adhesive may additionally permeate partially or fully through the thickness of one or both of the panels. This may form a stronger bond, or act to modify the characteristics of the lapped region itself due to the properties of the permeated adhesive.

While illustrated in FIG. 1B as existing in the laminated panels as a discrete layer of adhesive, the adhesive 5 may melt or otherwise permeate into the lapped panels such that there is either a thinner discrete layer of adhesive between the panels subsequent to bonding, or even no discrete layer of adhesive.

In addition to the type of adhesive and location within the lapped region at which the adhesive is provided, different amounts of adhesive may be provided to form bonds of different characteristics. For example, a relatively greater amount of adhesive may be provided to create a bond having a greater desired strength.

Different amounts of adhesive may be applied to different parts of a single lapped region or between different layers of a lapped region where there are three or more layers. Different amounts of adhesive may further be provided to different lapped regions of the headgear.

The properties of the adhesive utilised for the bonding, or for various different bonds within the headgear, may also be changed to suit the characteristics desired of each particular bonded area. For example, an adhesive may be provided having different levels of flexibility or stiffness when set, so as to suit the desired characteristics of the lapped region or part thereof at which it is utilised.

The properties of an adhesive may be selected to alter the properties of the panels where the panels are adhesively bonded. For example, the adhesive may provide increased stiffness or strength.

The properties of an adhesive may be selected to have certain similar properties of the panels at the adhesively bonded region. Properties of the adhesive such as stiffness and stretch and recoverability, may be selected to be similar to or entirely correspond to the properties of the panels at the bonded region. By this configuration the headgear may be provided with substantially continuous properties such as stiffness or stretch and recoverability through the relevant bonded regions. Such a headgear which has one or more continuous physical properties across the headgear, or at least across regions of the headgear, may provide increased comfort for a patient.

Such tailoring of the properties of an adhesive either to alter or be similar to the properties of the panels may be utilised at only specific lapped regions of the or between particular panels within a lapped region, or it may be utilised across the whole of a headgear. As a result, where the properties of the adhesive are to be tailored at multiple different bonds, different adhesives maybe be used at each respective bond to achieve the desired alteration of or similarity with the properties of the bonded panels.

In other configurations panels at a lapped region may be bonded to each other by other non-adhesive bonds. For example, panels may be ultrasonically bonded to each other by an ultrasonic weld. Panels may also otherwise be melted to each other to provide a join.

Where there are more than two panels at a lapped region or part thereof various ones of the interfacing panels may be joined by different methods.

Returning now to FIGS. 2A-14B, additional configurations of panels to form various lapped regions and non-lapped regions of a headgear will now be described.

Figure 2A:
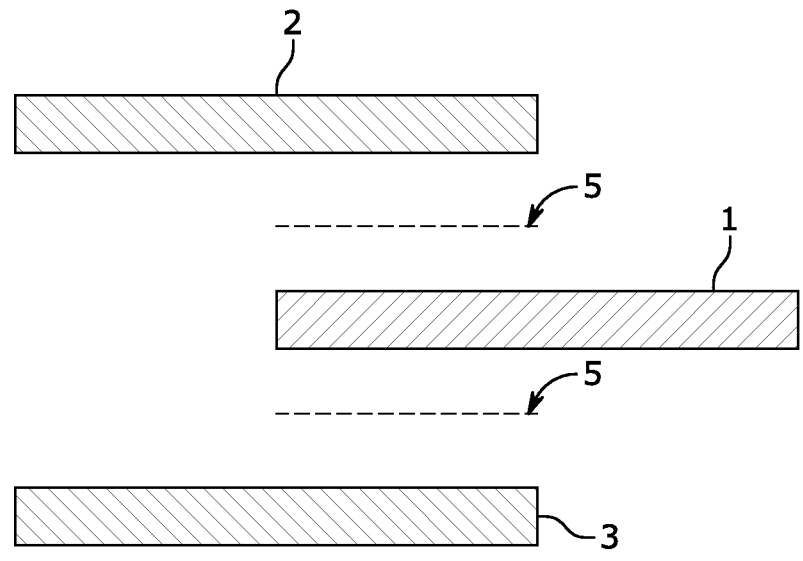
FIGS. 2A and 2B are cross-sectional views of a pre-lamination and laminated configuration of three panels.
Figure 2B:
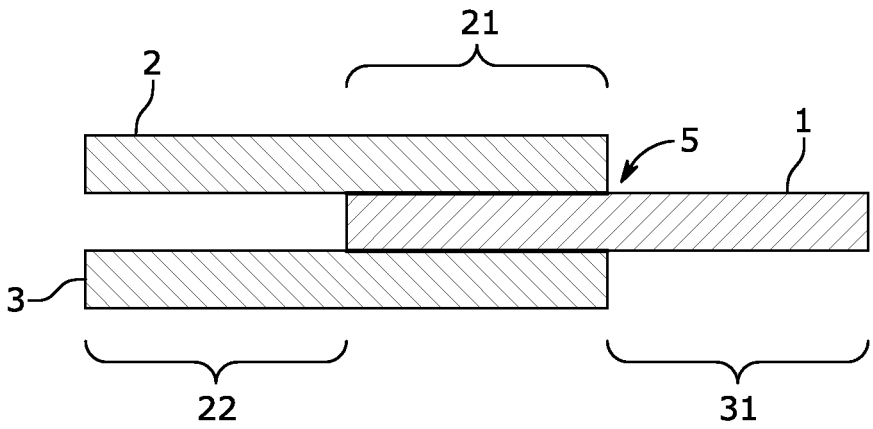

Referring first to FIGS. 2A and 2B, a configuration comprising three panels is shown. Seen in the pre-lamination exploded view of FIG. 2A, a first panel 1 is to be lapped on both major faces by a second panel 2 and a third panel 3. An adhesive 5 is to be provided at the overlapping and underlapping portions of the panels.

The laminated panels as seen in FIG. 2B form a first lapped region 21 where the first panel 1 is lapped on both sides by the second panel 2 and third panel 3. The second panel 2 and third panel 3 respectively lap opposed sides of the first panel.

The regions of overlap of the second panel with the first panel and the third panel with the first panel may be coextensive, with the second panel and third panel each lapping substantially identical areas of the opposed faces of the first panel. The regions of overlap may also be noncoextensive, with the second panel and third panel lapping the first panel over relatively lesser or greater areas, or in different regions of the opposed faces of the first panel.

The panels at the lapped region 22 are bonded together by the adhesive 5.

The laminated panels further form a second lapped region 22 at which the second panel 2 and third panel 3 may overlap and underlap each other. While illustrated in FIG. 2B as separated from each other, it will be appreciated that due to draping of the material and/or deformation under loading, the second panel 2 and third panel 3 may contact each other, at least at a region away from the terminus of the first panel 1.

As seen at the lapped region 22 of FIG. 2B, at some lapped regions an adhesive may not be provided between the lapped panels.

The panels of FIG. 2B further define a non-lapped region 31, at which the first panel 1 is not lapped on either side by another panel.

The configuration of FIGS. 2A and 2B may be characterised as a double lapped joint, as one panel is lapped on both sides. This is in contrast to the joint of FIGS. 1A and 1B, which may be characterised as a single lapped joint, as each panel is only lapped on one side.

In comparison to a single lapped joint, a double lapped joint such as shown in FIG. 2B may have the advantage of reducing the potential for inducing torsion in the joint under lateral loading of the respective panels. Such torsion may cause twisting or other deformation of the joint, so that at least part of the headgear does not lay flat. This may be undesirable in some circumstances, such as where the headgear is to lie flat against a patient's head, because any such torsion of the headgear may result in points of increased pressure against the patient's head, and thus discomfort.

Reduced or eliminated torsion at a bond may also increase the strength of the headgear at the bond. Torsion of the panels at the bond may cause them to be subjected generally to peel stresses and even to 180-degree (or "T") peel stresses when the panels are under tension. Bonded joints and particularly adhesively bonds may have limited strength under peel stresses, where the panels are pulled away from each other perpendicularly to the bonded surfaces. The reduction of torsion may mean that the panels are not twisted as much under loading, and consequently that they are not exposed to at least the same degree of peel stresses, but rather to predominantly or only shear stresses. Some bonds, particularly adhesive bonds, may be able to provide greater strength under shear stresses than peel stresses. This means that the strength of the headgear may be increased by reducing torsion at lapped panels.

In other configurations, for example where loads are not such as to cause significant torsion in the joint, a single lapped joint may be preferable to a double lapped joint as it may provide a joint of lesser thickness.

As illustrated in FIGS. 2A and 2B the first panel is of a different material than the second panel 2 and third panel 3, which are of the same material. For example, the first panel may be of a relatively stronger material than that of the second panel 2 and third panel 3. As another example, one of the first panel 1 and the second and third panels 2 and 3 may be of a relatively greater extensibility while the other or others are of a relatively lesser extensibility.

Figure 3A:
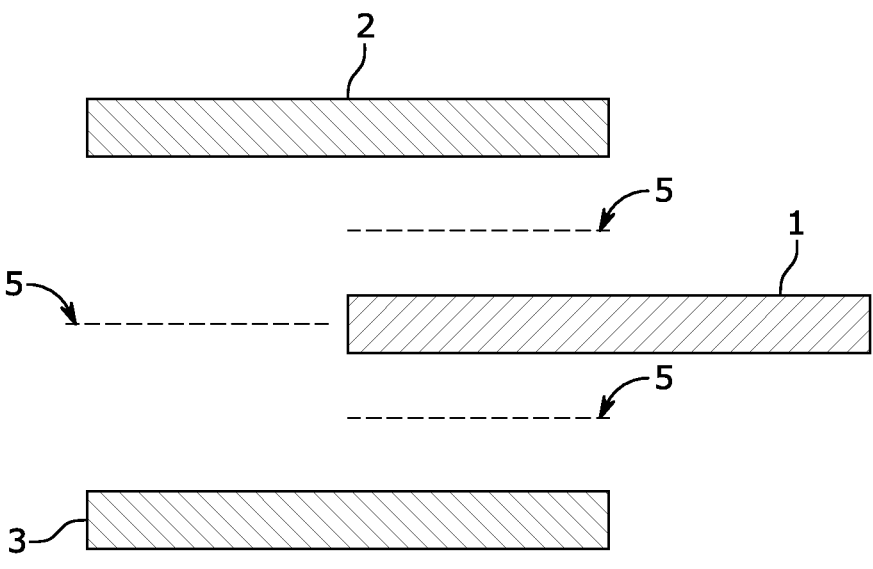
FIGS. 3A and 3B are cross-sectional views of another pre-lamination and laminated configuration of three panels.
Figure 3B:
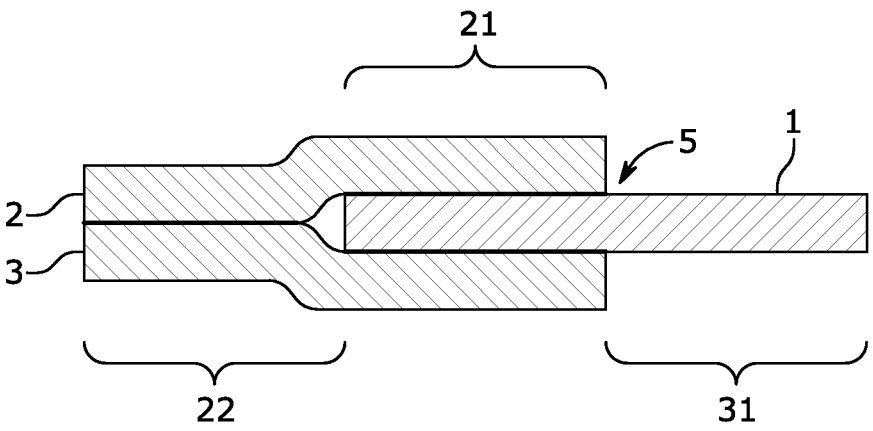

FIGS. 3A and 3B illustrate the panel lapping configuration of FIGS. 2A and 2B, but where an adhesive 5 is provided between the second panel 2 and third panel 3 at the second lapped region 22.

The second lapped region defines a bonded region unlike that of FIG. 2B. The first lapped region 21 defines a double lapped joint, while the second lapped region 22 defines a single lapped joint.

Figure 4A:
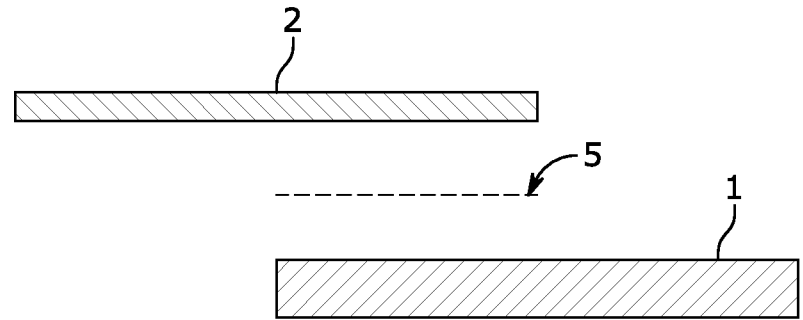
FIG. 4A is a pre-lamination cross-sectional view of a first panel of a given thickness is a second thinner panel.
Figure 4B:
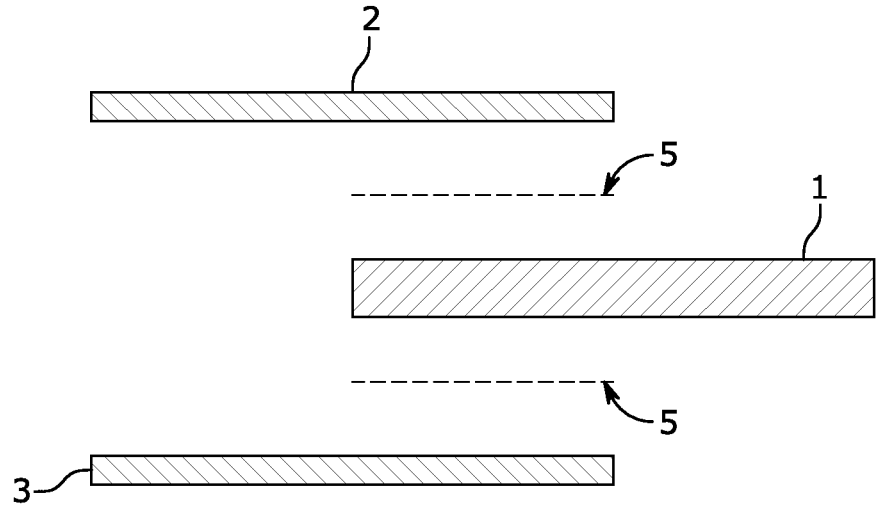
FIG. 4B is a pre-lamination cross-sectional view as in FIG. 4A, but where the first panel is lapped on the other side by another thinner panel.

FIGS. 4A and 4B illustrate two further configurations of a joint between panels. Each of FIGS. 4A and 4B show illustrative exploded views of the panels before they are laminated.

FIG. 4A shows a similar configuration to that of FIG. 1A, with a first panel 1 bonded to a second panel 2 by an adhesive 5. However, in FIG. 4A, the first panel 1 is of a greater thickness than the second panel 2.

FIG. 4B shows the configuration of FIG. 4A, but where the first panel is additionally lapped on its other main face by a third panel 3. The third panel 3 is similarly adhered to this first panel 1 by an adhesive 5. In the embodiment of FIG. 4B, the third panel is thinner than the first panel. The third panel is of a similar thickness as the second panel.

The configuration of FIG. 4B may provide for a joint such as has been described in FIGS. 2A and 2B, but which has a lesser overall thickness due to a relatively decreased thickness of the second panel 2 and third panel 3.

Where the second panel 2 and third panel 3 are of the same material or together have the same or similar strength as that of the first panel 1, a joint of the configuration of FIG. 4B may be useful for transferring a load from the first panel to the second and third panels, or in a reverse direction, such that the first panel is loaded in the same way as the second and third panels collectively.

The edges of the second panel 2 and the third panel 3 may be left without being adhered to each other, as has been described in relation to FIGS. 2A and 2B, or may be adhered to each other as was described in relation to FIGS. 3A and 3B.

Figure 5A:
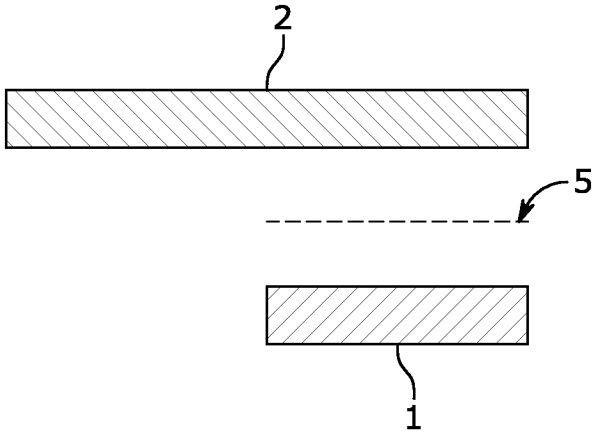
FIGS. 5A and 5B are pre-lamination and post-lamination cross-sectional views of another configuration of two panels.
Figure 5B:
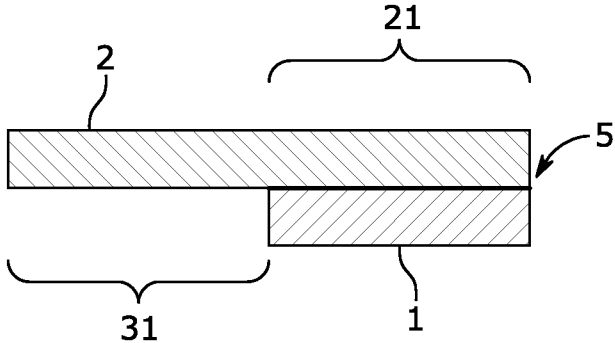

FIGS. 5A and 5B are respectively pre-lamination and post-lamination views of a further joint configuration. As seen in these figures, a first panel 1 is lapped on an entirety of one of its major faces by a second panel 2. As shown in FIG. 5A and FIG. 5B the first panel is located at an end of the second panel 2. In this illustrated embodiment at least one edge of the first and second panels are coextensive. However, in other embodiments, the first panel 1 may be located away from an edge, for example in the middle of second panel 2.

An adhesive 5 is shown between the lapping portions of the first panel 1 and the second panel 2. As seen in FIG. 5B when adhered together the panels provide a first non-lapped region 31 at one end of the second panel 2. It then defines a first lapped region 21, at which the second panel 2 overlaps the entirety of the first panel 1.

Figure 6A:
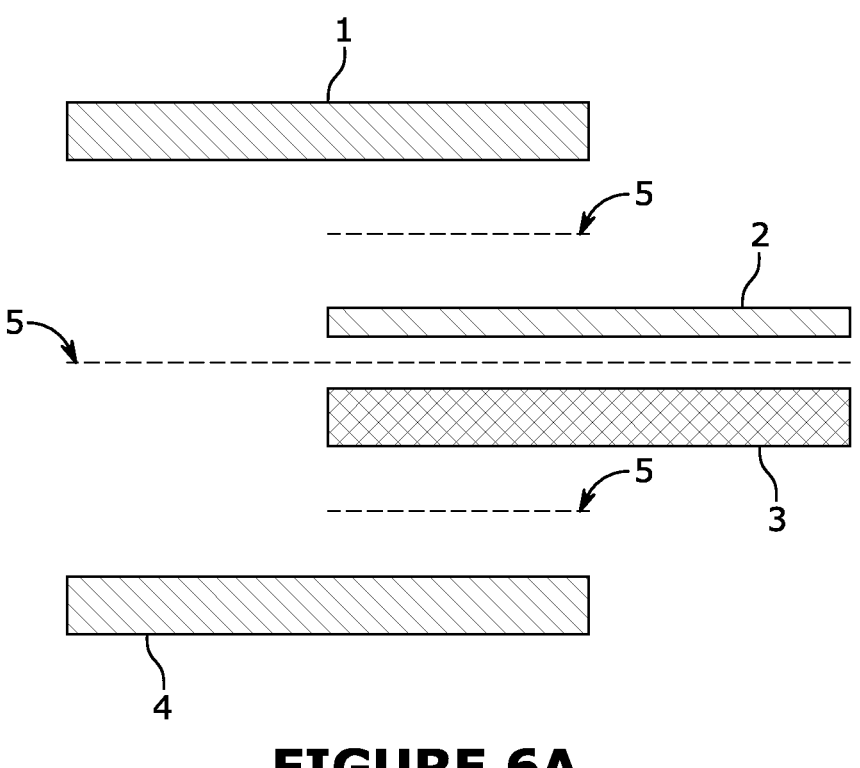
FIGS. 6A and 6B are pre-lamination and post-lamination cross-sectional views of a first and second panel, which are lapped against each other, and which are partially overlapped and underlapped by another pair of panels.
Figure 6B:
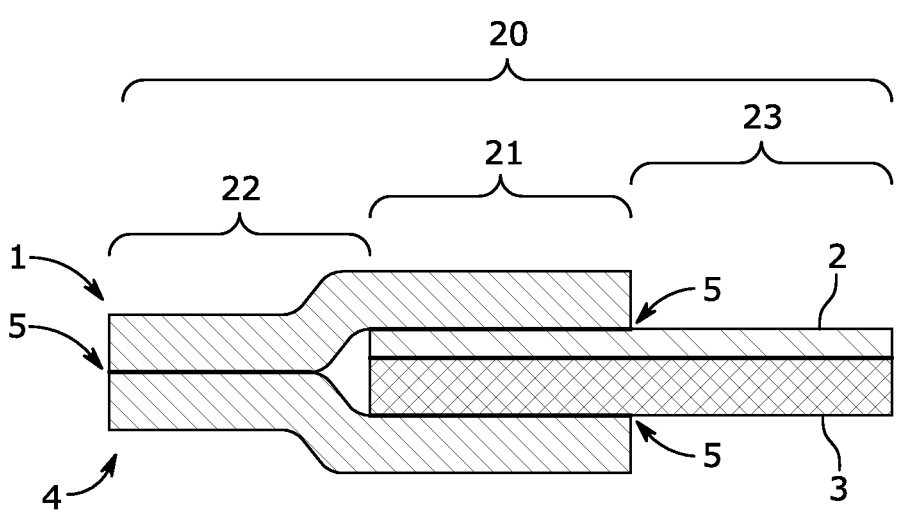

FIGS. 6A and 6B are section views of another more complex joint arrangement between multiple panels. As seen in FIG. 6A a first panel 1 and a fourth panel 4 define the outer panels of the headgear at a lapped region of the first, second, third and fourth panels. Between the first panel 1 and the fourth panel 4 is the second panel 2 and third panel 3.

A whole major face of one or both of the second panel 2 and third panel 3 may be lapped by the other of the second panel 2 and third panel 3. The second panel 2 and third panel 3 are provided with an adhesive 5 between them, and adhesive 5 is provided respectively between the first panel 1 and second panel 2 and third panel 3 and fourth panel 4 at the regions where they overlap. Finally, adhesive 5 is also provided between the ends of the first panel 1 and fourth panel 4.

FIG. 6B is a laminated section view of the assembly of FIG. 6A. The entire panel assembly of FIG. 6B defines one overall lapped region 20.

Within the overall lapped region 20, the assembly defines three distinct lapped regions. At the first lapped region 21 the panels are in a multiply lapped configuration, with more than two panels being lapped against each other. The second and third panels 2 and 3 are lapped to each other and are subsequently overlapped and underlapped respectively by the first panel 1 and fourth panel 4. At the second lapped region 22 the first panel 1 and fourth panel 4 are singly lapped against each other and bonded together by the adhesive 5. Similarly, at the third lapped region 23 the second panel 2 and third panel 3 are lapped against each other in a single lapping configuration and bonded together by the adhesive 5.

FIGS. 6A and 6B illustrate how compound and complex joint configurations may be obtained by combinations of panels to define various singly and multiply lapped regions.

For illustration purposes the second panel 2 and third panel 3 are of a different material, including being of different thicknesses, similarly the first panel one and fourth panel 4 are of another panel type having a different thickness. It will be appreciated that any such configuration of same or different panels within a joint at a lapped region may be provided in order to enable the desired joint characteristics and overall characteristics of the headgear.

Similarly, as previously described, the characteristics, type, and quantity of the adhesive 5 between different respective panels of the panel layout of FIGS. 6A and 6B may be customised. That is, the adhesive between the first panel and second panel could be a different adhesive than the adhesive which is between the second and third panels, and so forth.

Figure 7A:
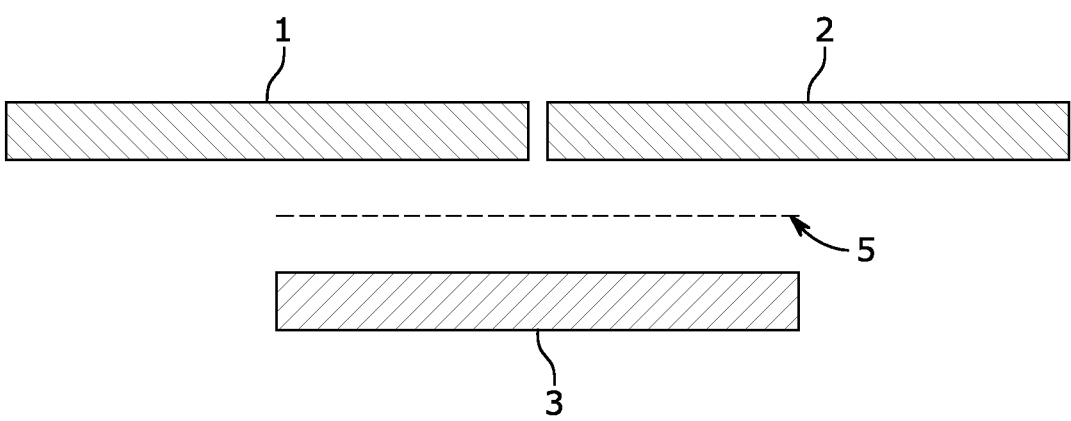
FIGS. 7A and 7B are pre-lamination and post-lamination cross-sectional views of a butt-join between two adjacent panels which are lapped on one side by another panel.

FIG. 7A is an exploded view of a panel layup to join a first panel 1 and second panel 2 in a butt join, where the major faces of the panels are substantially aligned, and they are joined in end-to-end condition. As seen in FIG. 7A the first panel 1 and second panel 2 are aligned end to end and are each underlapped or overlapped by a third panel 3. An adhesive 5 is provided between the lapping portions of the panels. Whilst shown in FIG. 7A as being fully lapped with the first panel 1 and second panel 2, the third panel 3 may in other variant configurations only partially be lapped with one or both of the panels. For example, the third panel may have a portion that extends along an axis that is orthogonal to a longitudinal axis of the first and/or second panels. That is, the third panel may extend lengthwise into or out of the page whilst the first and/or second panels extend lengthwise across the page as illustrated in FIGS. 7A and 7B.

Figure 7B:
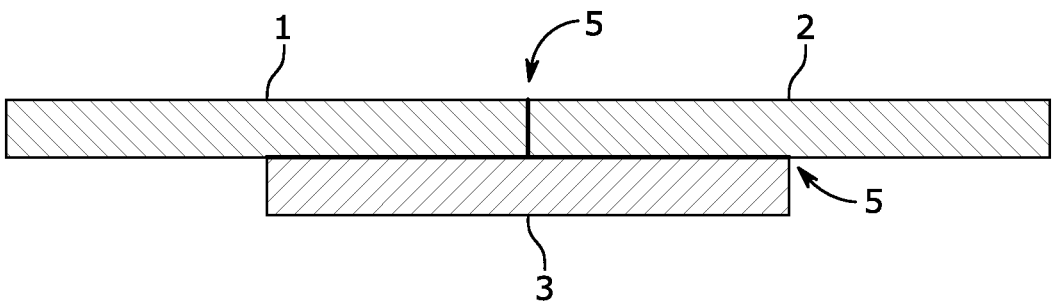

FIG. 7B shows a laminated configuration of the panels of FIG. 7A. As seen in FIG. 7B, the first panel and second panel 2 are in a substantially aligned planar condition.

In addition to adhesive being provided at the lapped major faces of the panels, an adhesive may be provided also between the ends of the first panel one and second panel 2 at the butt join.

Whilst shown in FIGS. 7A and 7B as being of at least the same thickness, the first panel 1 and second panel 2 may in variant configurations be of different thickness or other material properties.

Figure 8:
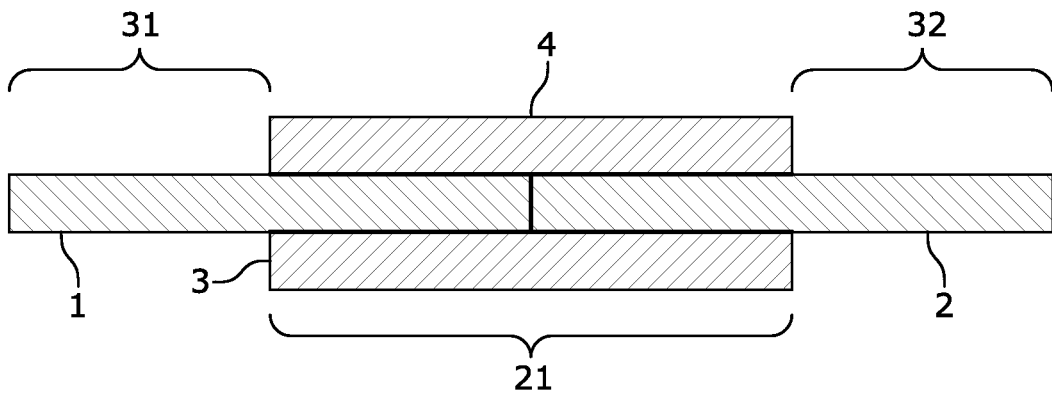
FIG. 8 is the post-lamination configuration of FIG. 7B, where the two adjacent panels are lapped on their other major faces by another panel at the butt join.

FIG. 8 shows the panel layup of FIG. 7B, but where the first panel 1 and second panel 2 are further overlapped by a fourth panel 4 corresponding to the third panel 3. Such a configuration may be desirable to provide an increased strength of the join between the first panel 1 and second panel 2. This configuration may also be desired to reduce or eliminate torsion of the joint when loads are applied to the first panel 1 and second panel 2.

As illustrated in FIG. 8, the panel layup of that figure defines a first non-lapped region 31 and second non-lapped region 32 at the distal ends at the first panel 1 and second panel 2, respectively. It also defines a first lapped region 21 at which the fourth panel 4 and third panel 3 sandwich the internal portions of the first panel 1 and second panel 2.

Figure 9A:
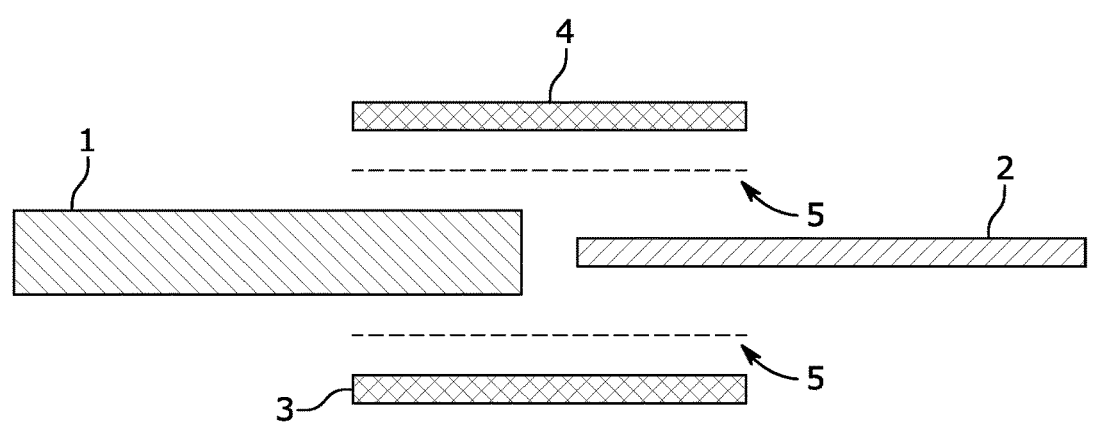
FIGS. 9A and 9B are pre-lamination and post-lamination views of a butt join between two adjacent panels as in FIG. 8, but where the two adjacent panels are of different thicknesses.

FIG. 9A illustrates a variant of the panel layup shown in FIG. 7A, where the first panel 1 and second panel 2 are of different thicknesses. In contrast to the layup shown and described in FIGS. 7A and 7B, the first lapped region 21 of FIG. 9B changes in thickness along its length.

Figure 9B:
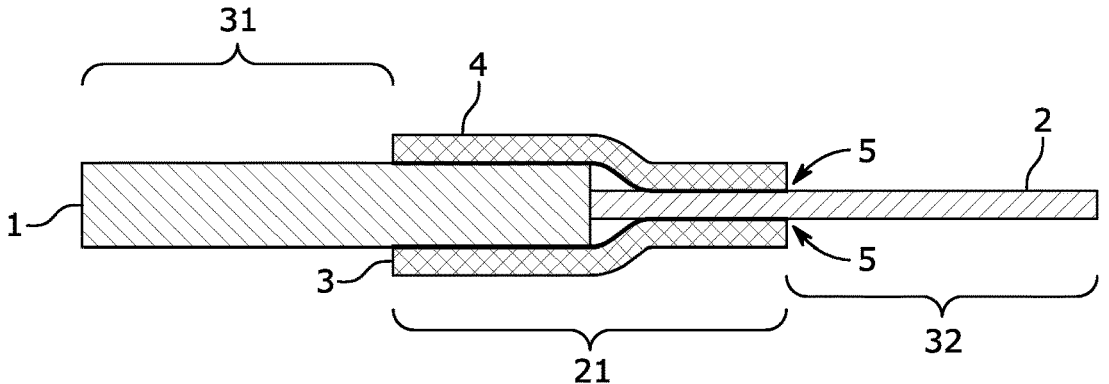

In addition to providing for a bond between the second panel 2 and first panel 1, the layup configuration of FIG. 9B may provide for a smooth transition between the thickness of the first panel 1 and the second panel 2. This may particularly be the case where the third panel 3 and fourth panel 4 are provided of a relatively thin material when compared to at least the thicker of the first and second panels.

Figure 10:
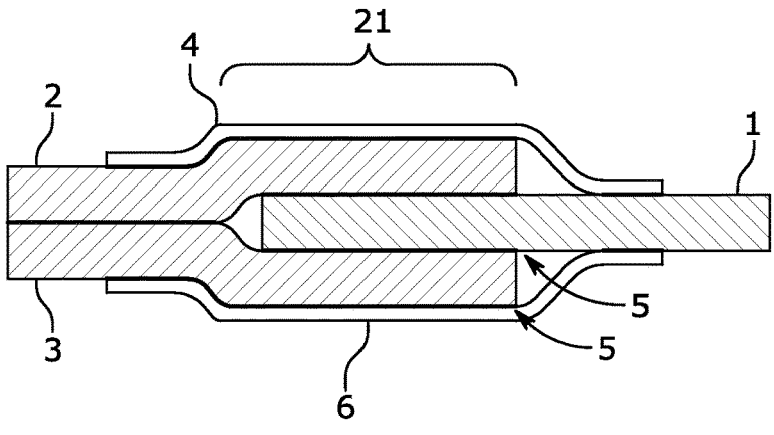
FIG. 10 is an example post-lamination cross-sectional view of a first panel which is overlapped and underlapped by another two panels which are, away from the first panel, lapped on each other, as in FIG. 3B, but where the first panel and other two panels are further overlapped and underlapped by a pair of panels which are thinner than that of the other panels.

FIG. 10 illustrates a panel layup of the configuration of FIG. 3B, but where these panels are further overlapped and underlapped at and to both sides of the first lapped region 21 by respectively a fourth panel 4 and fifth panel 6.

As noted in relation to FIG. 9B the fourth panel 4 and fifth panel 6, particularly where provided with a thinner material than the other panels or at least the second panel 2 and third panel 3, may provide a function of at least smoothing an edge transition in thickness between first, second and third panels 1, 2 and 3 at the lapped region 21.

According to various embodiments the surfaces or portions of the surfaces of one or more panels may be conditioned, and in particular the edges of panels may be conditioned. The conditioning may be by the addition of a conditioner to change the material properties of the panel at the treatment region. For example, conditioning may serve to increase the stiffness of the edge of a panel which is treated or change the surface texture or hardness. In another example where the panel is of an unravelable material, conditioning an edge of the panel may serve to prevent the material from unravelling.

The conditioning may condition only a surface of the panel or may be provided to penetrate into or fully through the panel and condition a substantial entirety of the thickness of the panel at the conditioned region.

The conditioning may utilise any range of known substances or materials to provide the conditioning, for example a solid, semi-solid, liquid, gel, or paste. The conditioning substance or material may cure to form the desired conditioned properties, as with an adhesive as previously described. Various conditioning substances which cure, particularly where they are provided as a solid or semi-solid, may be activated such as by melting or combination of two parts in order to initiate or accelerate the curing process.

In other forms the conditioning substance or material may be provided to the panel or panels without requiring curing. For example, the conditioning may be provided by a material which is applied to the panel in its final form, such as in a solid as a tape. Any such material which is applied in its final form may be joined to the panel or panels by bonding by an adhesive, or by stitching, welding, or other commonly utilised methods of joining.

In some configurations an adhesive such as the adhesive 5 used to bond the panels to each other may be utilised to provide the conditioning. The adhesive used to both bond panels and provide conditioning may have a non-tacky finish when cured.

Various examples of applications of conditioning of panels are shown in FIGS. 11A to 13B.

Figure 11A:
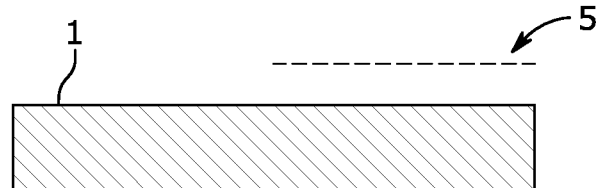
FIGS. 11A and 11B are pre-lamination and post-lamination cross-sectional views of one surface of edge of a panel which is treated with an adhesive.
Figure 11B:
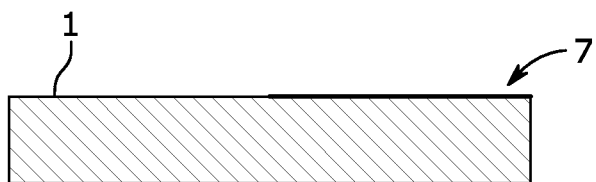

As shown in FIG. 11A, a first panel 1 may be treated with the conditioner 7. When applied to the panel and potentially as allowed to cure, dry, or harden, the conditioner 7 changes the material properties of the first panel 1 at the conditioned region. For example, where the conditioner 7 provides a relatively greater stiffness than that of the panel by itself, the panel 1 at the conditioned edge region may be caused to have a relatively increased stiffness with respect to the remainder of the first panel 1.

As a further example the conditioner 7 may provide for a modification of the surface characteristics of the panel, such as an increased hardness.

Figure 12A:
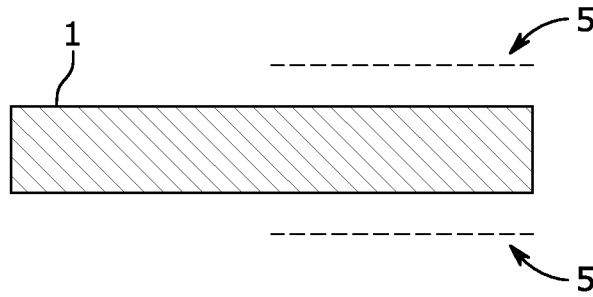
FIGS. 12A and 12B are the configuration of FIGS. 11A and 11B, but where both major faces along the edge of the panel are treated with an adhesive.
Figure 12B:
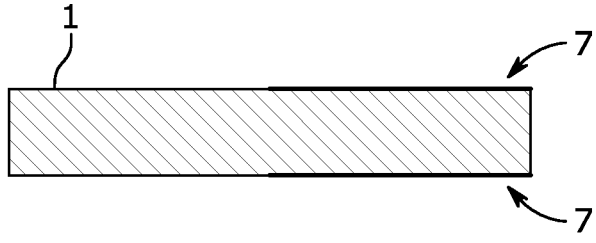

FIG. 12A illustrates the configuration of FIG. 11A, but where both major faces of the first panel 1 at the same edge have been provided with a surface treatment by a conditioner 7. FIG. 12B correspondingly illustrates the applied, bonded, cured, or otherwise treated configuration of FIG. 12A, where both major faces at the edge region have been provided with a conditioning.

Where the panel is made of an unravelable material (which could be a knit or woven fabric), the conditioning of one or both major surfaces, or of an edge surface of the panel, may act to inhibit unravelling of the fibres of the material at that end.

Figure 13A:
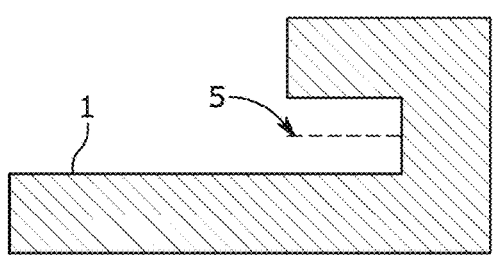
FIGS. 13A and 13B are pre-lamination and post-lamination cross-sectional views of a panel which is rolled back and adhered to itself.
Figure 13B:
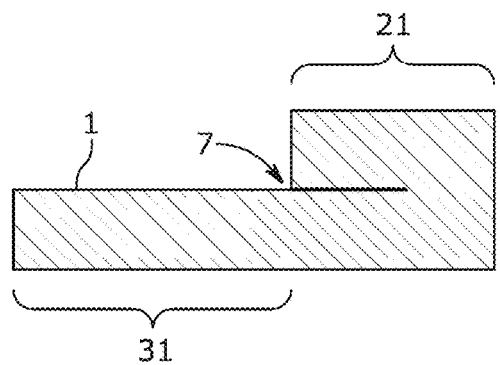

FIGS. 13A and 13B show a further configuration of treating of an edge of a panel 1. As seen in FIG. 13A, an edge of the first panel 1 is folded back onto itself and a conditioner in the form of an adhesive 5 is provided between the folded back portion and the remainder of first panel 1 which it overlaps. When laminated, as seen in FIG. 13B, the panel presents as a first non-lapped region 31 and the first lapped region 21.

The rolled back edge configuration of FIG. 13B may be desirable to provide an increased strength, stiffness, or thickness, at the edge of the panel. As described regarding the edge treatments of FIG. 11, the adhesive 5 may be customised to match or to provide different desired characteristics to supplement those of the first panel 1 itself. The rolled back edge configuration may additionally act to prevent the unravelling or fraying of fibres of the first panel 1.

The panel configuration of FIGS. 13A and 13B additionally illustrate an example of a panel configuration of a single panel which may define both non-lapped regions such as 31 and lapped regions such as 21.

Figure 14A:
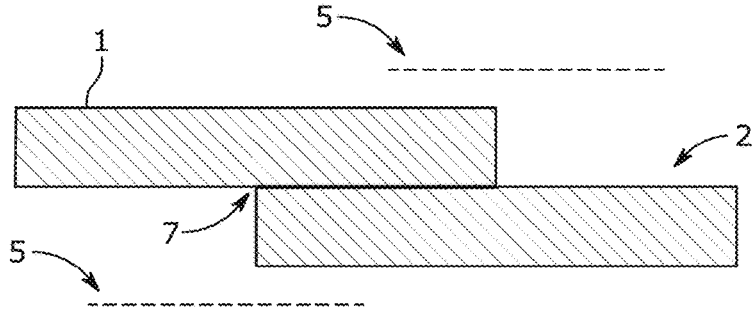
FIGS. 14A and 14B are pre-lamination and post-lamination cross-sectional views of two lapped panels, where the boundaries between the panels at each of their major faces is treated with an adhesive.
Figure 14B:
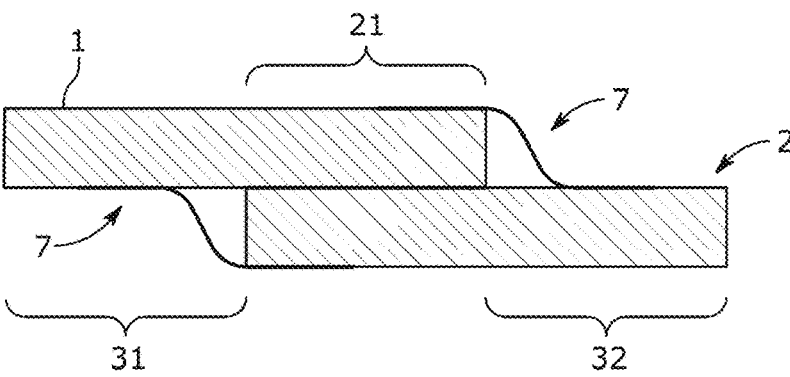

In addition to conditioning of edges of one or more panels, further applications of the use of a conditioner 7 as a surface finish are contemplated herein. FIG. 14A shows the panel layup of FIG. 1B, but where a conditioner 7 is provided to overlap and underlap the transitions between the first panel 1 and second panel 2. As seen in FIGS. 14A and 14B the conditioner 7 may be in the form of a tape, such as a plasticised tape for seam sealing.

In the laminated view of FIG. 14B the conditioner 7 is shown to provide surface joining between the major surfaces of the first panel 1 and second panel 2 on both respective sides.

While shown for purposes of illustration in FIG. 14B as resulting in a solid layer of conditioner 7 between the two panels, depending on the type and configuration of the conditioner 7 utilised the conditioner may not result in an appreciable increase in thickness of the panels, but rather simply condition the associated regions of each panel. For example, this could be to provide increased stiffness, hardness, or other such properties.

Figure 15:
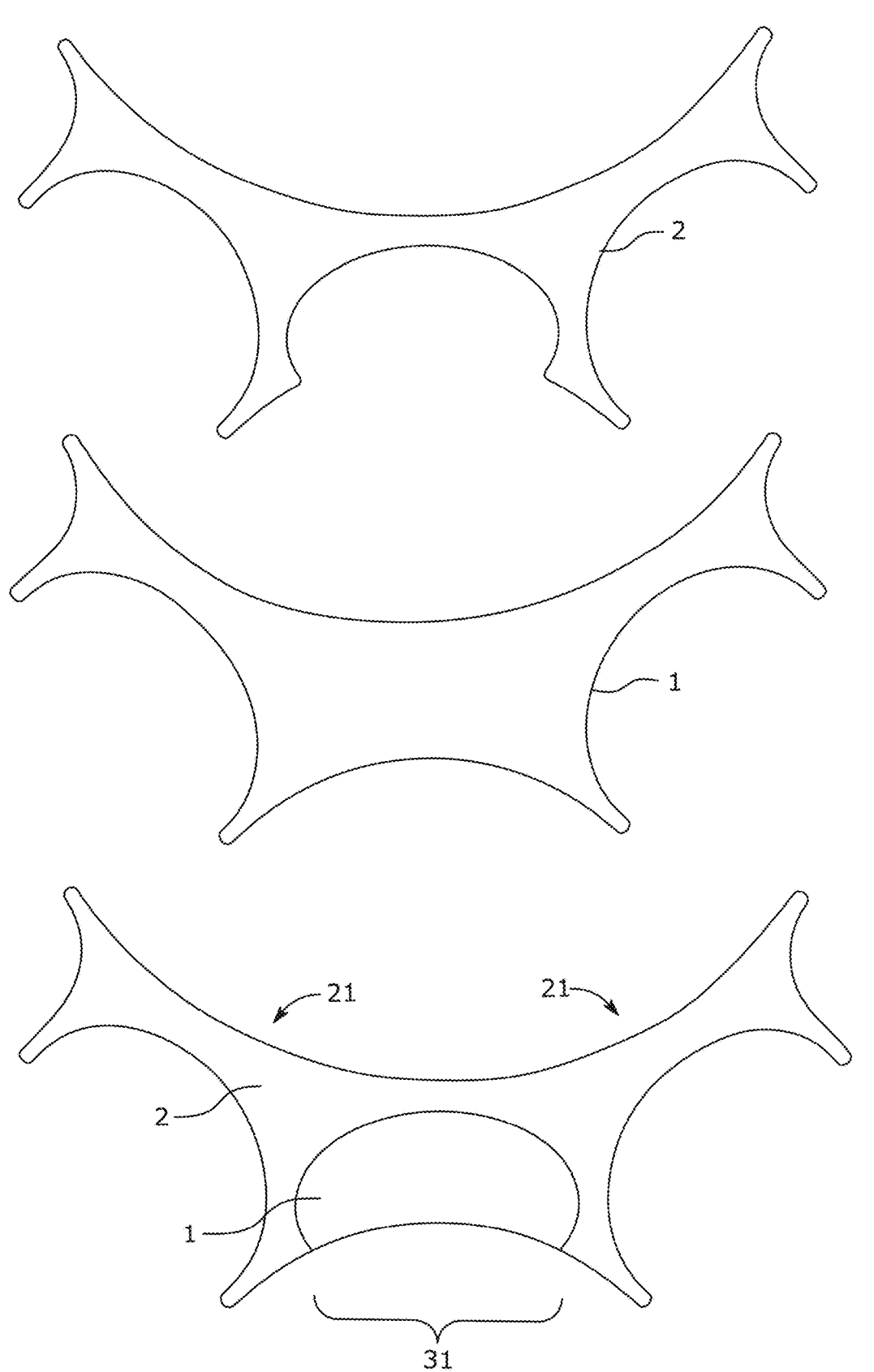
FIG. 15 shows two panels which combine to form a part of a headgear.

FIG. 15 illustrates at top two panels, a first panel 1 and a second panel 2, which are to be bonded to each other to define a part of a headgear. While fully overlapping each other at their distal regions, the second panel 2 comprises a semi-circular cut out at a central part.

When bonded together as shown in the lower portion of FIG. 15, the two panels combine to form a headgear portion defining a first lapped region 21 at the overlap of the first panel 1 and second panel 2, and a non-lapped region 31 at the part where the first panel 1 is not lapped by the second panel 2.

Such a configuration may provide the laminated panel layup with location-specific characteristics. For example, where the second panel 2 is a relatively lesser stretch or even non-stretch panel and the first panel 1 is a relatively greater stretch panel, the layup may have less extensibility or even be inextensible at the lapped region 21, while maintaining extensibility at the non-lapped region 31.

The bonding together of all or part of the lapped first panel 1 and second panel 2 at the lapped region may provide reduced stretch at the bonded region relative to that of either the first panel or second panel alone.

The bonding together of all or part of the lapped first panel 1 and second panel 2 at the lapped region may provide reduced stretch at the bonded region relative to that of the lapped first and second panels at a non-bonded region. As a further example, where the second panel 2 is a non-elasticated panel and the first panel 1 is an elasticated panel, the layup may have elastic stretch properties at the non-lapped region 31, but substantially inelastic properties at the lapped region 21.

While the foregoing has described various example layups of different panels, it will be appreciated that any number of variations or combinations of such layups may be provided in order to form a headgear.

While shown comprising various panels of particular illustrative thicknesses, it will be appreciated that the foregoing layups may be provided with panels of different thicknesses and combinations of thicknesses, among any other desired material properties.

With reference to the foregoing description of panel configurations and panel layups to provide a headgear having lapped and non-lapped regions various particular embodiments of a headgear utilising lapped panels will now be described.

Figure 16A:
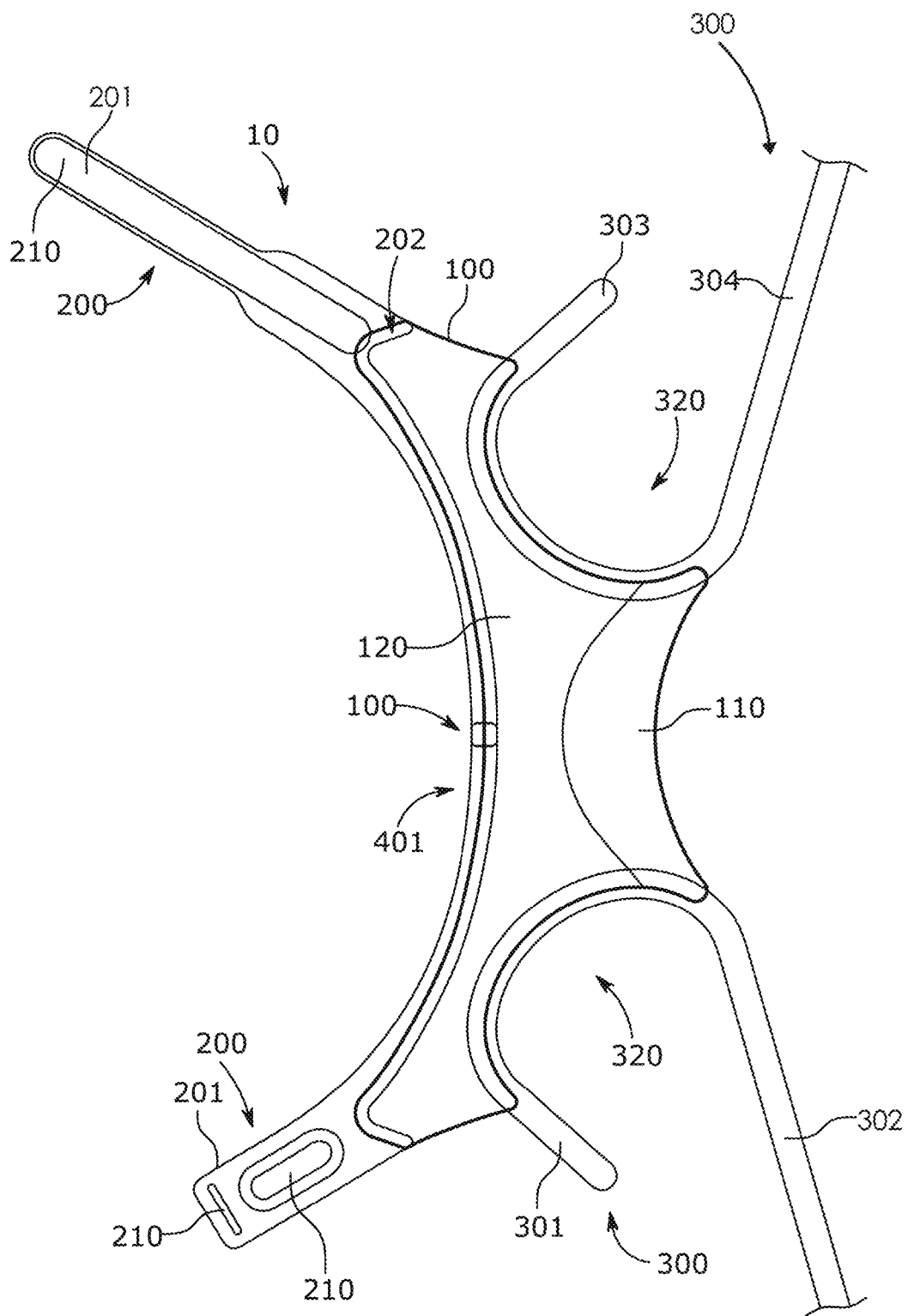
FIG. 16A is a lay-flat view of a headgear.

FIG. 16A is a lay-flat view of a headgear 10.

A headgear 10 may define an internal surface 14 and an external surface 15 of the headgear (not seen in FIG. 16A). The internal surface is, in use, for contact with the head of the patient. The external surface is conversely for facing away from the patient's head.

According to various embodiments the internal surface 14 and external surface 15 may be configured to be the same or different. In various preferred embodiments the internal surface 14 and external surface 15 may be configured differently. This different configuration may be to reflect different use functions of the headgear at its inside and outside. They may additionally or alternatively be to signal to a patient which surface is which, to assist the patient in orienting and donning the headgear.

The headgear 10 comprises a rear portion 100 for location at the rear of a patient's head in use. A purpose of the rear portion 100 may be to transfer loads from straps 300, which connect to the interface, to the patient's head and enable the interface to be retained against the patient's face.

The headgear 10 of FIG. 16A also includes a crown strap 200, for location about a crown of the patient's head in use. The crown strap 200 may be provided as two or more discrete parts which are joined together to form a loop, such as is shown in FIG. 16A. In alternative configurations the crown strap 200 may be provided as a continuous loop.

Where the crown strap 200 includes two parts which are joined together to form a loop, the crown strap may include one or more crown strap fixture parts 210. For example, as seen in FIG. 16A, one side of the crown strap comprises a slot and one half of a fastening system to couple with a corresponding half of a fastening system, such as a hook and loop fastener, on the other side of the crown strap.

The side straps 300 are for attachment to the patient interface, and for transferring loads variously to either or both of the rear portion 100 and crown strap 200.

In at least some configurations the side straps 300 may be of a non-stretch material such that they are substantially inextensible. As such they may transfer loads between the patient interface and the rear portion of the headgear without extending to any significant extent.

As seen in FIG. 16A, the side straps 300 may comprise sets of upper side straps 301 and 303 and lower side strap 302 and 304 of each side respectively. Where there are sets of side straps on each side, a region between the two side straps may define an ear loop 320. The ear loop 320 comprises a portion of the headgear which extends between each respective upper side strap and lower side strap on one side of the headgear. Each upper side strap 301, 303 passes above the ear, and each lower side strap 302, 304 passes beneath the ear. The ear loop 320 is located at least behind the ear. The edge of the ear loop between each upper strap and lower strap may be curved or may comprise a plurality of linear edges arranged about a nominal curve.

In other embodiments the headgear 10 may include only two side straps, one strap for connecting to each side of the interface.

In addition to illustrating the various parts of a headgear 10, FIG. 16A illustrates some panel layups which are utilised to form the overall headgear 10.

For example, as seen in FIG. 16A each set of upper and lower side straps, 301 and 302, and 303 and 304 respectively, are defined by a single panel of material. At each side of the headgear, this panel is lapped in at least a single-lapping configuration to one or more panels of the rear portion 100. Such a configuration may substantially or entirely eliminate peel stresses and particularly 180-degree peel stresses under tensile loading of the strap and rear portion, and instead cause the stresses at the panel bonds to be substantially or entirely shear stresses. This may accordingly improve the load carrying capability of the bonded panels.

In FIG. 16A the rear portion 100 comprises a first rear panel 110 and a second rear panel 120. These panels may be configured in the same manner as the first panel 1 and second panel 2 of FIG. 15, wherein the second rear panel 120 is fully laminated to the first rear panel 110, but for at the crescent shaped lower extent of the first rear panel 110.

In other configurations the first rear panel 110 may only be of a crescent shape such as is visible in FIG. 16A and may be bonded to the second rear panel 120 by a lap join or butt join as previously described.

As the rear portion is to be located at the rear of a patient's head, the lower extent of the rear portion is to be located around the upper part of the patient's neck. This is a region which may have considerably variable geometry between people of different anatomies, and thus may be a point of discomfort for patients using a given headgear.

Accordingly, as described in relation to FIG. 15, the first rear panel 110 may be of a stretch material, such that it can stretch and allow the headgear 10 to take on different shapes to accommodate different neck anatomies. In particular, the first rear panel 110 may have a relatively greater stretchability than that of the second rear panel 120.

The lower edge of the first rear panel 110 may be a free edge, without a seam. It may be provided either with some edge treatment, or preferably without any edge treatment. Particularly where the lower edge of the first rear panel 110 does not have a seam or any edge treatment, the first rear panel may be of a non-unravelable material.

The absence of a seam and/or any edge treatment of the lower edge may increase the comfort of the headgear for a patient by providing continuous properties, such as stretch, stiffness, and thickness, across the whole of the first rear panel 110 from the second rear panel 120 down to the lower edge of the first rear panel.

As seen in FIG. 16A the strap panel of each side is bonded to a first rear panel 110 and second rear panel 120 of the rear portion 100. The layup is such as to form a lapped region and a non-lapped region of the strap panel about each ear loop 320.

While shown as relatively short lengths, it will be appreciated that the straps 300 will be provided in sufficient length to reach and couple with an interface, given a range of different patient head sizes.

The crown strap 200 as shown in FIG. 16A comprises a single crown strap panel 201 which extends across the rear portion 100 and is lapped against the second rear panel 120 and/or first rear panel 110 where it fully laps the second rear panel 120.

In addition to being lapped along an upper edge of the rear portion 100 the crown strap panel 201 may be lapped with at least a lateral part of the rear portion 100, as illustrated at 202 in FIG. 16A. This may function to provide increased strength to the bond between the crown strap 200 and rear portion 100 and improve the ability to transfer loads between the two regions. In addition to providing potentially increased strength, bonding at the region 202 may increase resistance to peeling of the crown strap panel 201 and the rear portion 100 from each other.

Figure 16B:
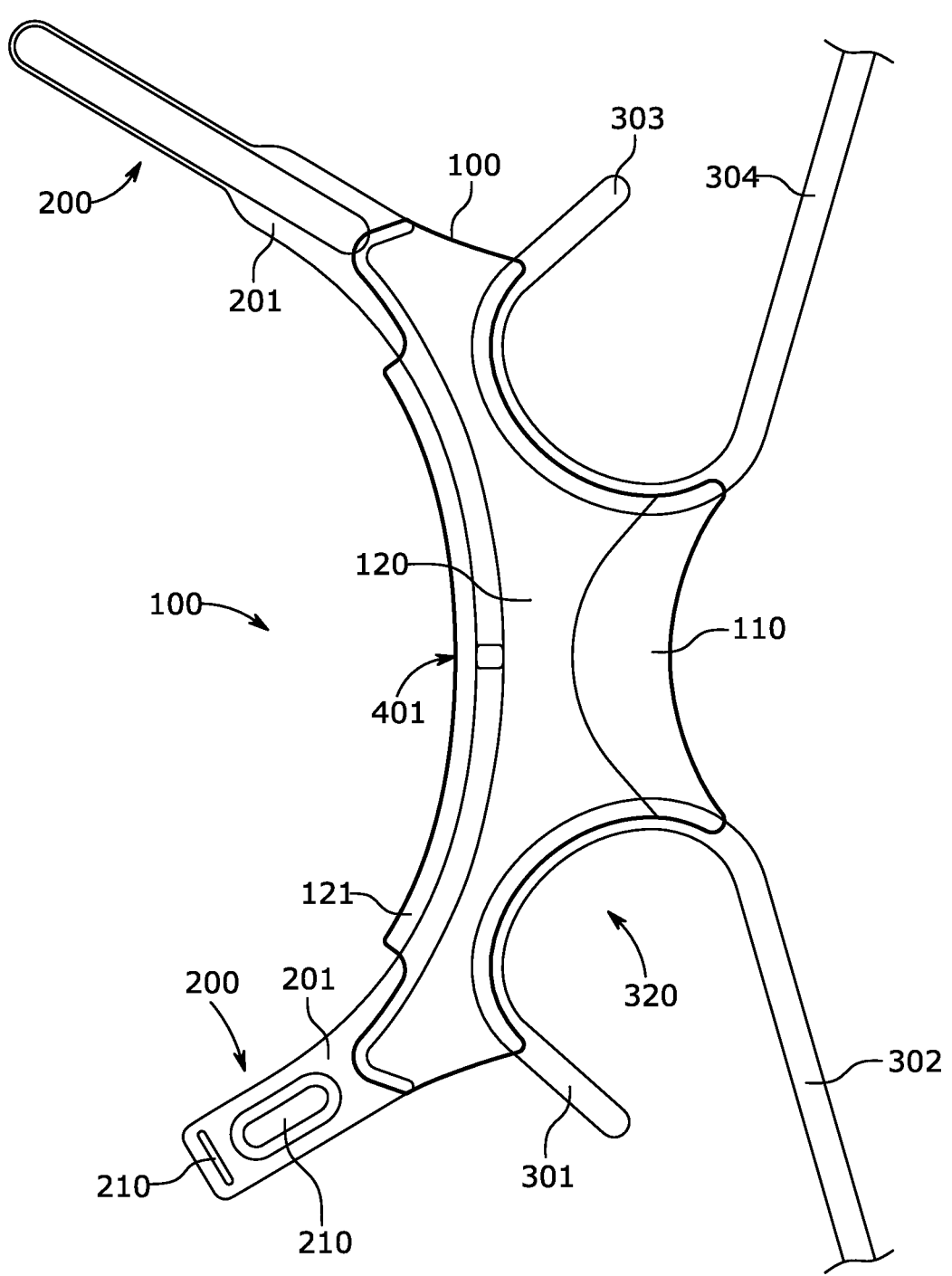
FIG. 16B is a lay-flat view of another embodiment of a headgear.

FIG. 16B shows another illustration of a headgear 10 similar to that of FIG. 16A, but with various modifications to the rear portion and crown strap.

In FIG. 16B the top of the second rear panel 120 of the rear portion 100 extends to an upper peripheral edge 401 which projects past the crown strap panel 201. By this configuration, the second rear panel 120 defines an upper edge 401 of the headgear around at least the rear of the patient's head.

The portion of the second rear panel 120 which extends from the crown strap panel 201 to the upper edge 401 comprises a non-lapped region of the headgear.

As the second rear panel 120 at the overhanging portion 121 beyond the crown strap panel 201 is unsupported and may not be substantially load bearing, when in contact with the head of a patient it may roll or curl away from the patient's head. This may create a region of reducing pressure against the patient's head from the upper edge of the crown strap panel 201 to the distal edge of the overhanging portion 121 of the second rear panel 120.

Such a zone of gradually reducing pressure may provide for increased comfort for a patient, as opposed to a sharp drop in pressure across a hard edge which may make the patient more aware of the presence of the headgear or cause pressure irritation of the tissue at the edge.

The function of such an overhanging portion 121 may be characterised as providing an edge softening, to create a region of reducing pressure towards the edge of the headgear and thus soften the feeling of the edge against a patient's head. An overhanging portion 121 to achieve this function may be provided as part of another panel of the headgear, such as part of the second rear panel 120 as seen in FIG. 16B. An overhanging portion 121 may instead be provided as part of a separate panel, for example as a panel lapped to at least the crown strap panel 201 and overhanging past it to define the upper edge of the rear portion of the headgear.

As seen in FIG. 16B, the upper panel 201 including the overhanging portion 121 is provided to be inside of the crown strap panel 20 relative to the patient's head. As such, the overhanging portion 121 will roll away from the head and preferably over the crown panel.

The panel comprising the overhanging portion 121 is at least one of thinner, softer, and less dense than the headgear panel which it overlies, in the case of FIG. 16B the crown strap panel 201.

The edge softening effect of an overhanging portion 121 may be enhanced where the overhanging portion 121 is at least partially protected from exposure to tensile loading referred from the straps 300. For example, in relation to FIG. 16B, the crown strap panel 201 may be configured to transfer minimal tensile loads from the upper side straps 301 and 303 to the overhanging portion 121. This may be achieved by limiting the stretch of the crown strap panel 201 or even providing it of an non-stretch material.

While described in relation to forming a pressure-graduating edge at the upper side of the rear portion 100 of the headgear, the described techniques may be applied to any other part of the headgear to achieve the same functionality. For example, this panel configuration may be utilised at the lower periphery of the rear portion 100, and/or at the ear loops 320.

The panels of the headgear may be configured to give a particular overall shape or structure to the headgear, which it may have when it is not being worn.

Such shapes or structures may be important for signalling to a patient or person who will apply the headgear to a patient the nature of the various parts, and their intended orientations for donning. For example, it may be desirable that the headgear at rest presents an opening between the straps of each side within which the patient's head may be received. Similarly, it may be desirable that the headgear at rest presents the side straps as distinct members, projecting away from the remainder of the headgear and potentially also individually of each other, to allow easy identification and grasping of each strap by the patient so that they may be connected to the interface.

This shape and structure may for instance be demonstrated when the headgear 10 is held by a patient, or particularly when a portion of the headgear is grasped by the patient and the remainder of the headgear drapes or hangs from the grasped portion.

Figure 17A:
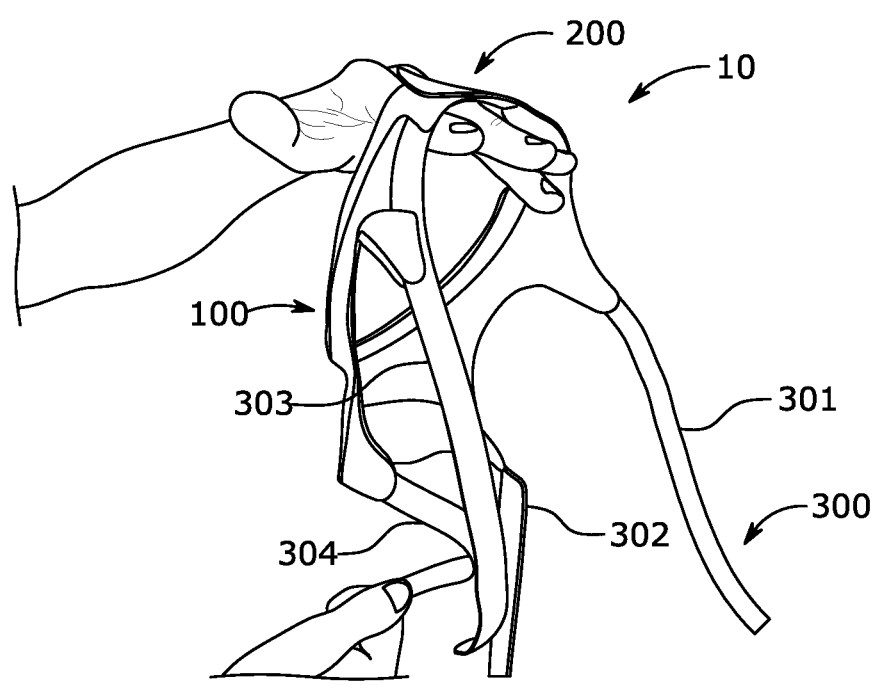
FIGS. 17A and 17B are views of the drape configuration of a headgear when held by a patient.
Figure 17B:
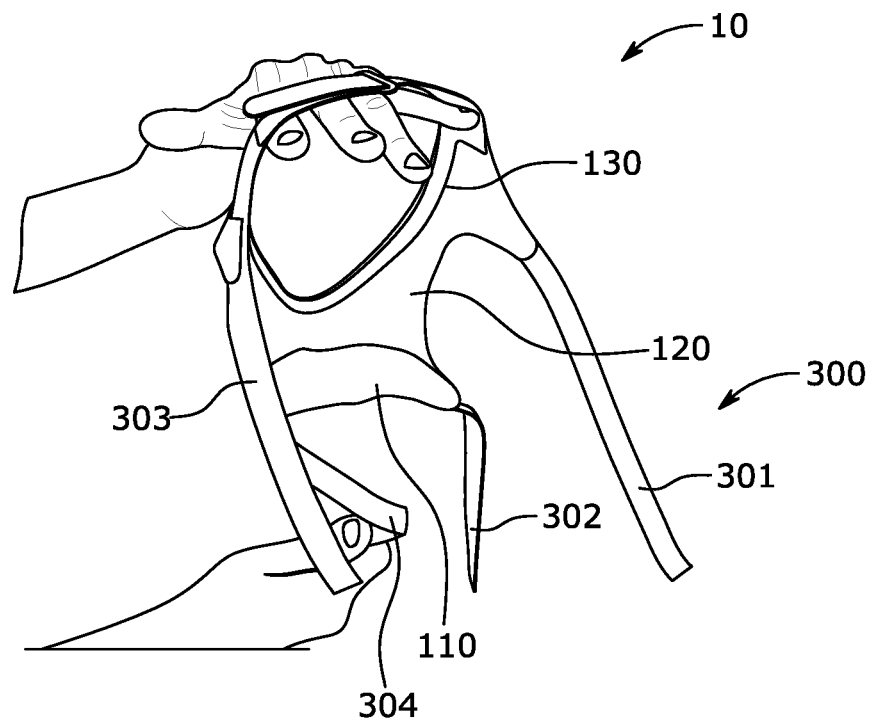

FIGS. 17A and 17B illustrate two different perspectives of a headgear 10 when draped from the patient's hand. As seen in FIGS. 17A and 17B, the headgear 10 of this embodiment is configured to display certain shape and form when not worn.

The headgear 10 may have a crown strap 200 which has sufficient stiffness that it at rest retains an at least partially circular form. This is shown in the example of FIGS. 17A and 17B, where the remainder of the crown strap 200 draping from the patient's hand demonstrates a substantially circular form.

Also seen particularly in FIG. 17B is the way in which the straps 300 may project away from the remainder of the headgear 10, and also discretely of each other. To provide such a configuration the panel or panels which comprise the straps 300 may be provided of a material of sufficient stiffness so as to drape with a sufficiently low amount of curvature over their length. In addition or alternatively, either or both of the rear portion 100 and/or crown strap 200 to which the straps 300 attach may bias the straps to fall outwardly, away from each other and away from the remainder of the headgear 10.

To achieve such a configuration the straps 300 and/or panels of the remainder of the headgear to which they lap may be provided with a natural curl or curve to them.

In some embodiments, a base panel may be laminated with a more peripheral stretch panel which is pre-stretched when laminated to the base panel. This may induce a natural curvature in the laminated panels, to provide a desired natural shape and/or divergence away from each other of the straps 300.

In addition or alternatively to any panel configurations to provide a resting shape to the headgear to signal the nature of the different portions or their use or application to a patient, the headgear may be configured to visually or by tactile cues signal these things to a patient.

For example, as seen in FIGS. 17A and 17B, the crown strap and rear portion of the headgear may be provided of one or predominantly one colour. In order to differentiate themselves from the remainder of the headgear, one or more of the straps 300 may be provided having a different colour and/or texture than that of the crown strap 200. As seen in FIGS. 17A and 17B, the upper side straps 301 and 303 may be provided having a different colour and/or texture than that of the lower side straps 302 and 304. Any such structural, visual, and/or tactile cues which may be built into the headgear may additionally or alternatively be utilised to aid a patient in differentiating between an internal surface 14 and an external surface 15 of the headgear 10.

For example, some or all of the panels which comprise the inner surface may be provided having a different colour or different colours than some or all of the panels which comprise the external surface 15 of the headgear.

In other configurations, some or all of the panels which comprise the internal surface 14 of the headgear may have a different texture than some or all of the panels defining the external surface 15. In particular, the texture of the inner surface 14 may be in part or whole softer than the external surface 15, to aid in signalling to the patient that this part should be in proximity to their head as well as to provide enhanced comfort when worn.

Figure 18A:
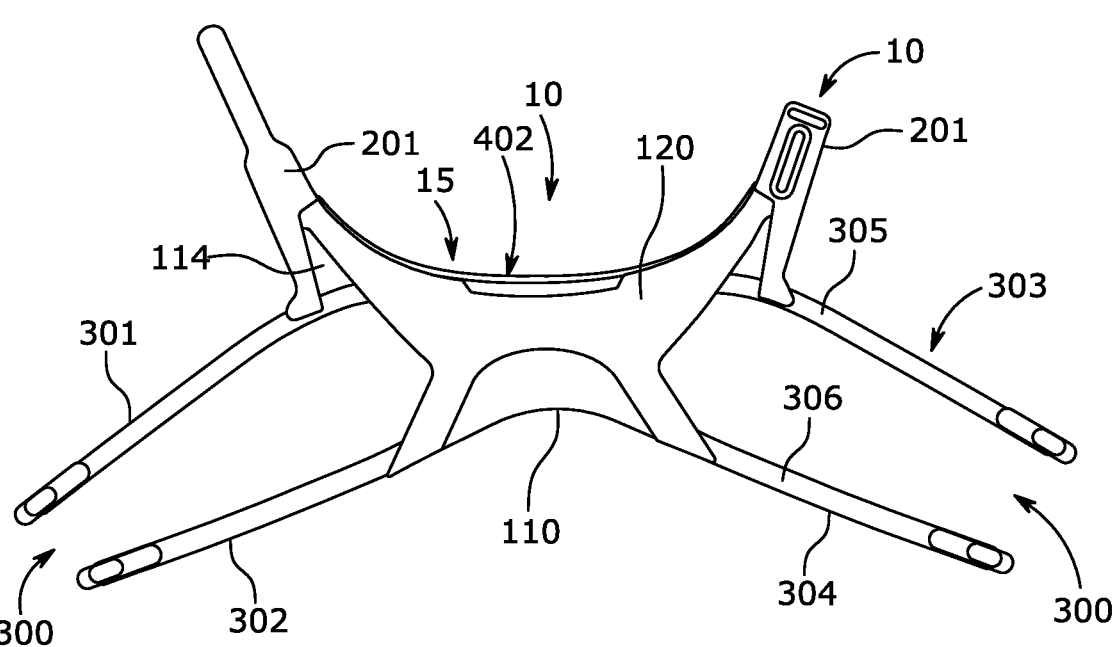
FIGS. 18A and 18B are respectively inside and outside views of a headgear.
Figure 18B:
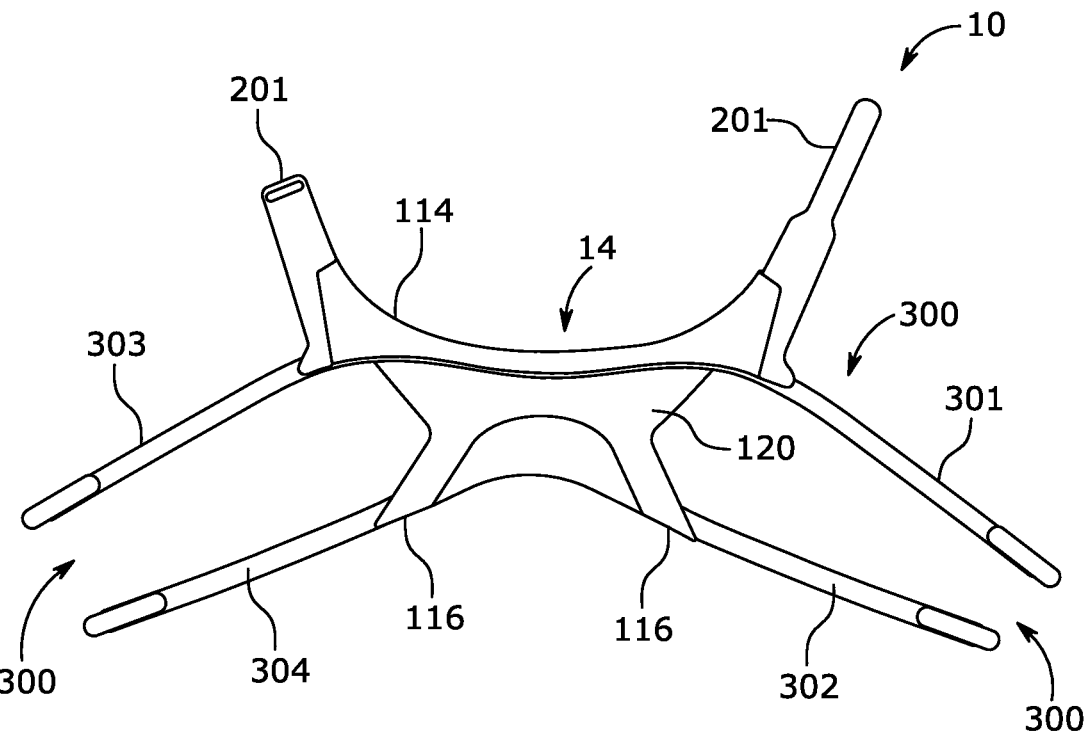

FIGS. 18A and 18B show respectively views of the external surface 15 and internal surface 14 of an embodiment of the headgear 10. Various exemplary features of this embodiment will now be described.

The headgear 10 comprises a rear portion 100, crown strap 200, and side straps 300 as previously described.

The upper side straps 301 and 303 comprise a unitary panel or laminate of panels 305 which extend across the rear portion 100 of the headgear. By such a configuration the upper side straps 301 and 303 may transfer loads to the back of the patient's head whilst minimising undesirable loads in other regions of the headgear.

In the view of the outside of the headgear in FIG. 18A the top strap panel 305 is visible at a middle part of the rear portion 100, and also extends below an upper rear portion panel 114.

In some configurations the lower side straps 302 and 304 may also comprise a unitary panel. However, in the embodiment of FIGS. 18A and 18B they are separate panels.

The lower side straps 302 and 304 each connect to panels of the rear portion. The rear portion 100 includes a first rear panel 110 which may be of a stretch material and a second rear panel 120 which may be of a relatively lesser stretch material.

More particularly, the first rear panel 110 may be of an elasticated material and the second rear panel 120 may be of a non-elasticated material.

Figure 19A:
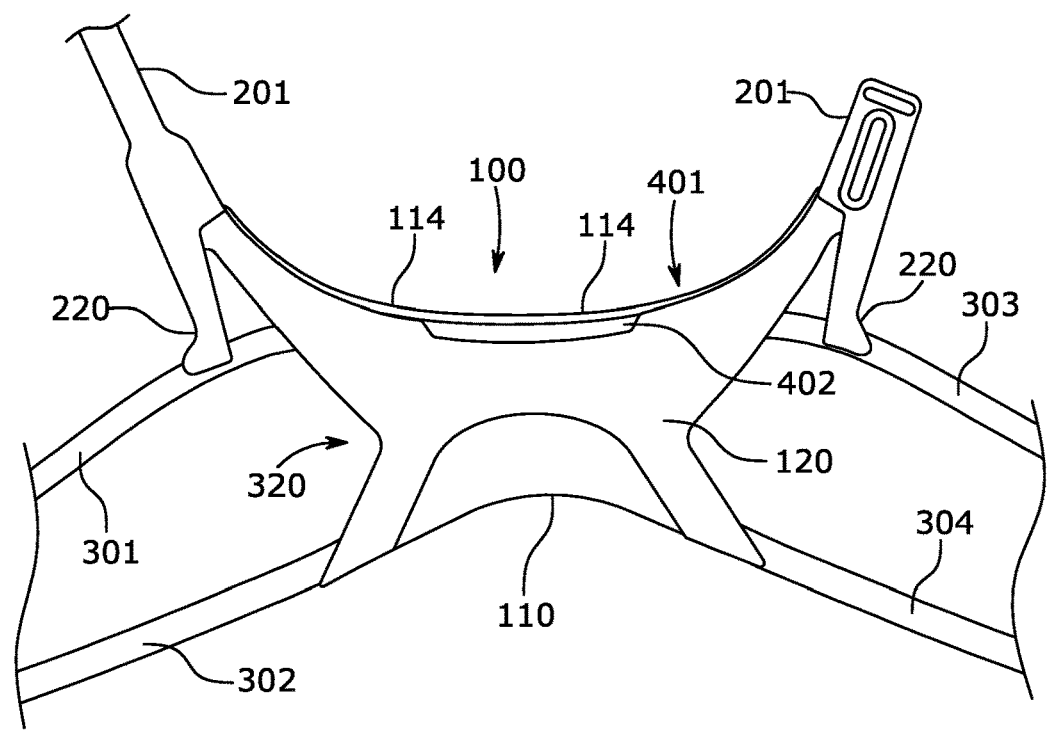
FIGS. 19A and 19B are close-up views of the configurations of FIGS. 18A and 18B.
Figure 19B:
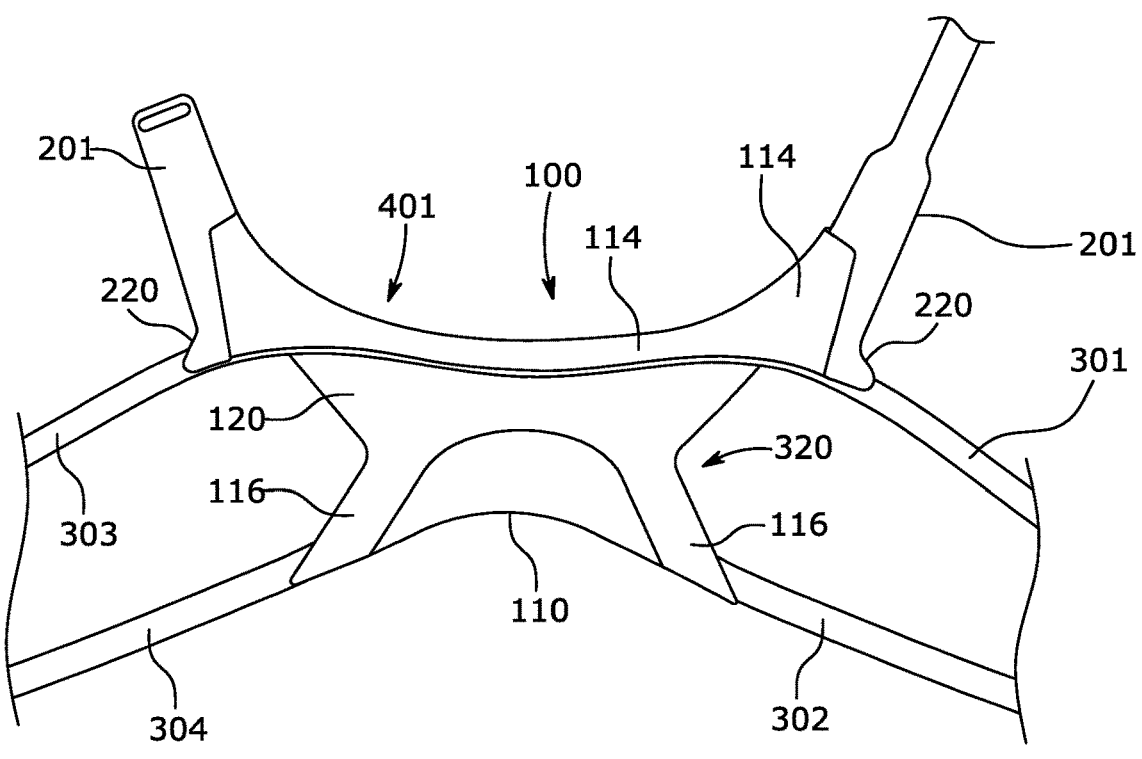

FIGS. 19A and 19B show close-up views of FIGS. 18A and 18B, respectively. In discussion of the configuration of various components of the rear portion 100 and crown strap 200 reference will now be made to FIGS. 19A and 19B.

The second rear panel 120 is preferably configured to receive loads from the upper side straps 301 and 303 and/or the lower side straps 302 and 304, and transfer and equalise loads received from the straps within the remainder of the headgear.

The lower side straps 302 and 304 may be laminated to the second rear panel 120 in a single lapping configuration such as has been described in relation to FIGS. 1A and 1B.

The lower side straps 302 and 304 may alternatively be double lapped, such as was described in relation to FIGS. 3A and 3B by the provision of supplementary rear panels 116. These supplementary rear panels may be provided to sandwich the strap panels against the second rear panel 120. Such double lapping may aid in ensuring that the lapped portion of the lower side straps 302 and 304 do not twist in-plane when they experience loads.

The supplementary rear panels 116 may be of a similar or the same relatively lesser stretch material as the second rear panel 120, so as to aid in the transfer of loads from the lower side straps 302 and 304 to the rear portion 100 and particularly the second rear panel 120.

Where the lower side straps 302 and 304 connect to the rear portion 100 across the first rear panel 110, loads on the lower side straps 302 and 304 may additionally function to stretch the first rear panel 110. The stretch and where applicable elasticity afforded by the first rear panel 110 may accordingly provide for greater tolerance for a patient to adjust the length of the straps to provide a desired retention force of the interface to their face.

However, particularly in configurations where the loads from the straps are not substantially transferred through the first rear panel 110 but instead are transferred through the second rear panel 120, such as in FIGS. 18A and 18B, the first rear panel 110 may stretch at least primarily to conform to the geometry of the patient's neck. Advantageously, by passing the side strap loads through the second rear panel 120, tension through the first rear panel 110 is reduced, in particular at its lower edge. This reduces the possibility of creating a hard edge at the lower edge of the first rear panel 110 that cuts into the patient's neck (which might especially occur if the lower edge reaches its limit of extensibility or elastic limit).

In addition to stretching to accommodate different neck geometries, a relatively greater stretch first rear panel 110 may also cause the headgear at that region to conform more continuously and snugly to the patient's head than would a relatively lesser stretch or non-stretch panel. The fit of a stretch panel to the patient's head at this neck region may aid in the comfort and stability of the headgear, or at least the kinaesthetic perception of stability to the patient.

The crown strap 200 may connect to the rear portion and/or the upper side straps 301 and 303. As seen in the view of the outside of the headgear of FIG. 18A, the crown panel 201 extends across the top of the rear portion 100. In FIG. 18B it extends behind the edge softening panel 114.

As seen in FIGS. 19A and 19B, the crown strap 200 may comprise a pair of laminated crown strap panels 201, each of which respectively laps one major face of the side strap and/or rear portion panel to which they lap. This is particularly visible at the intersection 220 of the upper side straps 301 and 303 with the crown strap 200, with a respective crown strap panel 201 overlapping the associated top strap in both the view of the outside of the headgear in FIG. 19A and the view of the inside of the headgear in FIG. 19B.

The rear portion 100 or crown strap 200 may additionally comprise one or more edge softening panels 114. The function of such an edge softening panel may be substantially as described previously in relation to the embodiment of FIG. 16B.

As seen in the view of the outside of the headgear in FIG. 19A, the edge softening panel 114 projects past the top of the crown strap panel 201, the second rear panel 120, and the upper side straps 301 and 303. As such, the edge softening panel 114 defines an upper edge 401 of the headgear at the rear portion.

A further feature of the embodiment of FIGS. 18 and 19 is the configuration of the ear loops 320. Unlike the embodiment of FIGS. 16A and 16B, the ear loops 320 are defined by both the upper and lower straps and the lateral peripheries of the rear portion 100.

With reference to FIG. 19A showing a view of the outside of the headgear, a cut-out 402 is shown in the second rear panel 120, which exposes the top strap running beneath it. Particularly where panels are of different colours or textures, configurations such as this may be utilised for creating differences in appearance between the inside and outside of the headgear, and/or to create signals to a patient as to how or where that part of the headgear is to be oriented in-use.

The ear loops 320 of FIGS. 19A and 19B define, between the respective upper and lower side straps, two substantially straight-line portions. These straight-line portions extend in a V-shape inwardly into the rear portion 100. Due to the in-use load conditions on the straps, the provision of ear loops comprising such straight-line portions may reduce a degree of crumpling or out-of-plane deformation warping of the rear portion peripheral edges at the ear loops 320.

Figure 20:
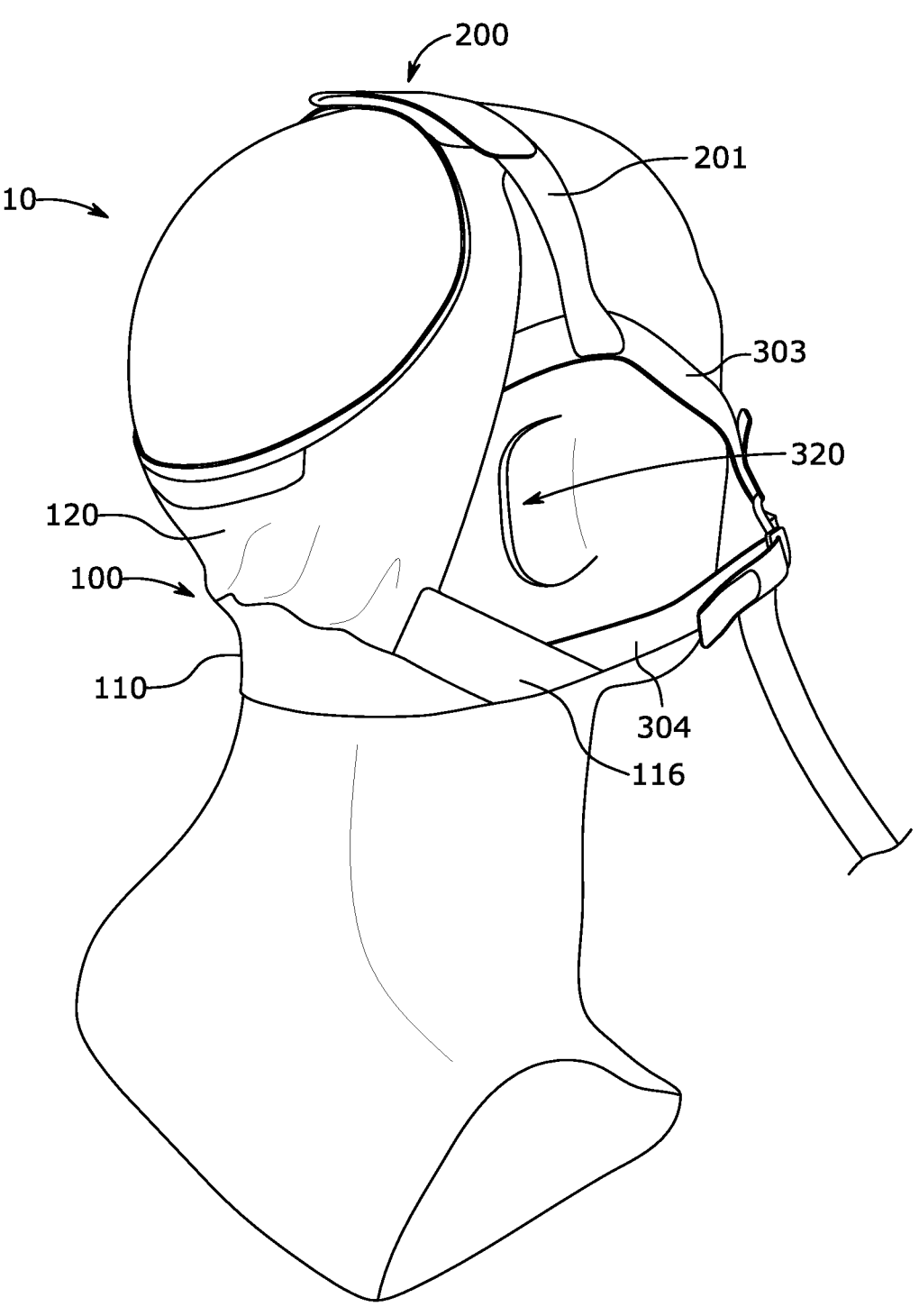
FIG. 20 is the headgear of FIGS. 18A and 18B on a patient's head.

FIG. 20 is a view of the headgear 10 of FIGS. 18A-B and 19A-B on an example patient's head.

FIG. 20 illustrates the load transfers adaptations of the crown strap panels 201 which respectively overlap and underlap the top strap 303.

Also seen is the first rear panel 110 and how it may stretch to fit the neck of the patient, and how loads from the lower side straps 302 and 304 may be transferred at least in part to the stretchable first rear panel 110.

Figure 21:
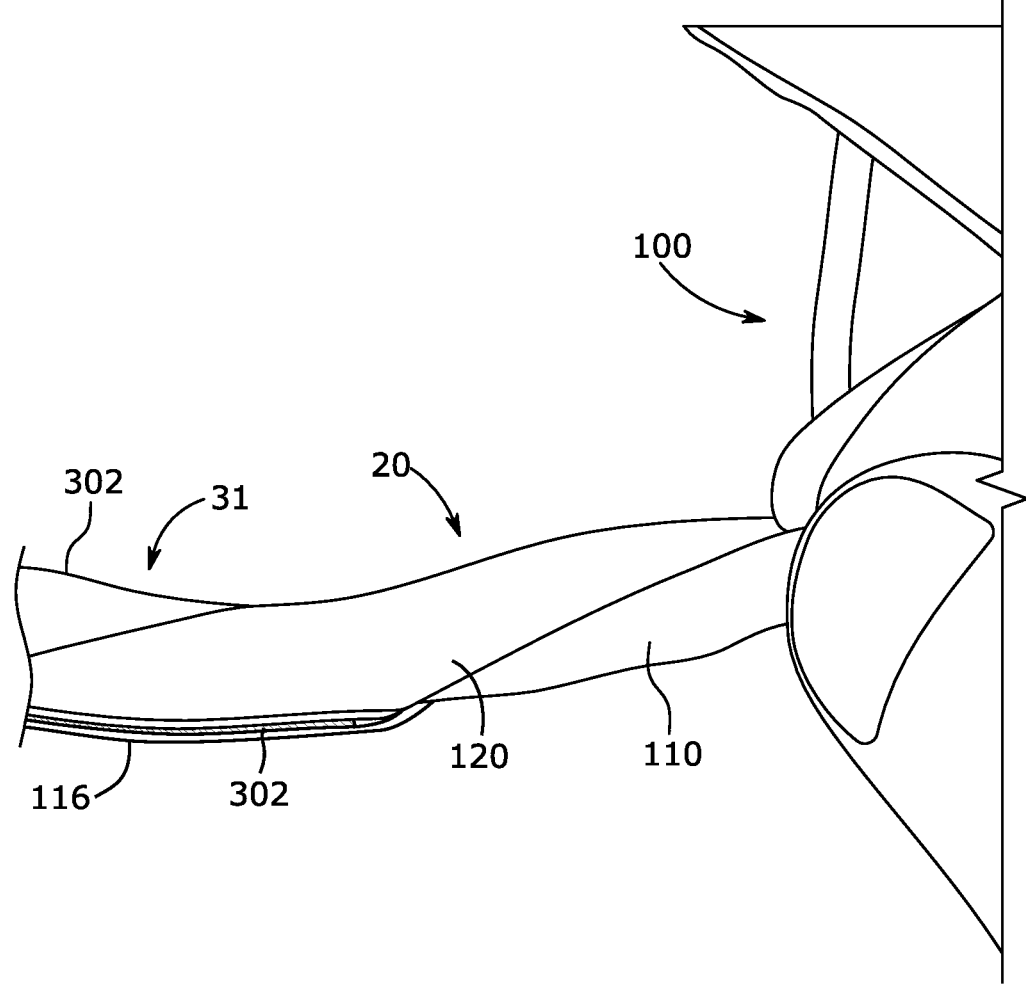
FIG. 21 is a lapped region between a side strap and the rear portion of a headgear.

FIG. 21 shows a close-up view of the region at which a lower side strap 302 is connected to the rear portion 200. The second rear panel 120 overlaps the proximate end of the lower side strap 302 and is adhesively bonded to it. The strap panel is double lapped between the second rear panel 120 and the supplementary rear panel 116. This panel layup at the intersection of the lower side strap 302, second rear panel 120, and supplementary panel 116 may be substantially as is illustrated in cross-section in FIGS. 2A and 2B.

Also shown in FIG. 21 is the first rear panel 110. This panel may be singly lapped to the second rear panel 120, and/or may be doubly lapped between the second rear panel 120 and the supplementary rear panel 116.

The various lapped panels in the close-up of FIG. 21 illustrate a lapped region 20 of the headgear 10, while the distal portion of the lower side strap 302 illustrates a non-lapped region 31.

Figures 22, 23:
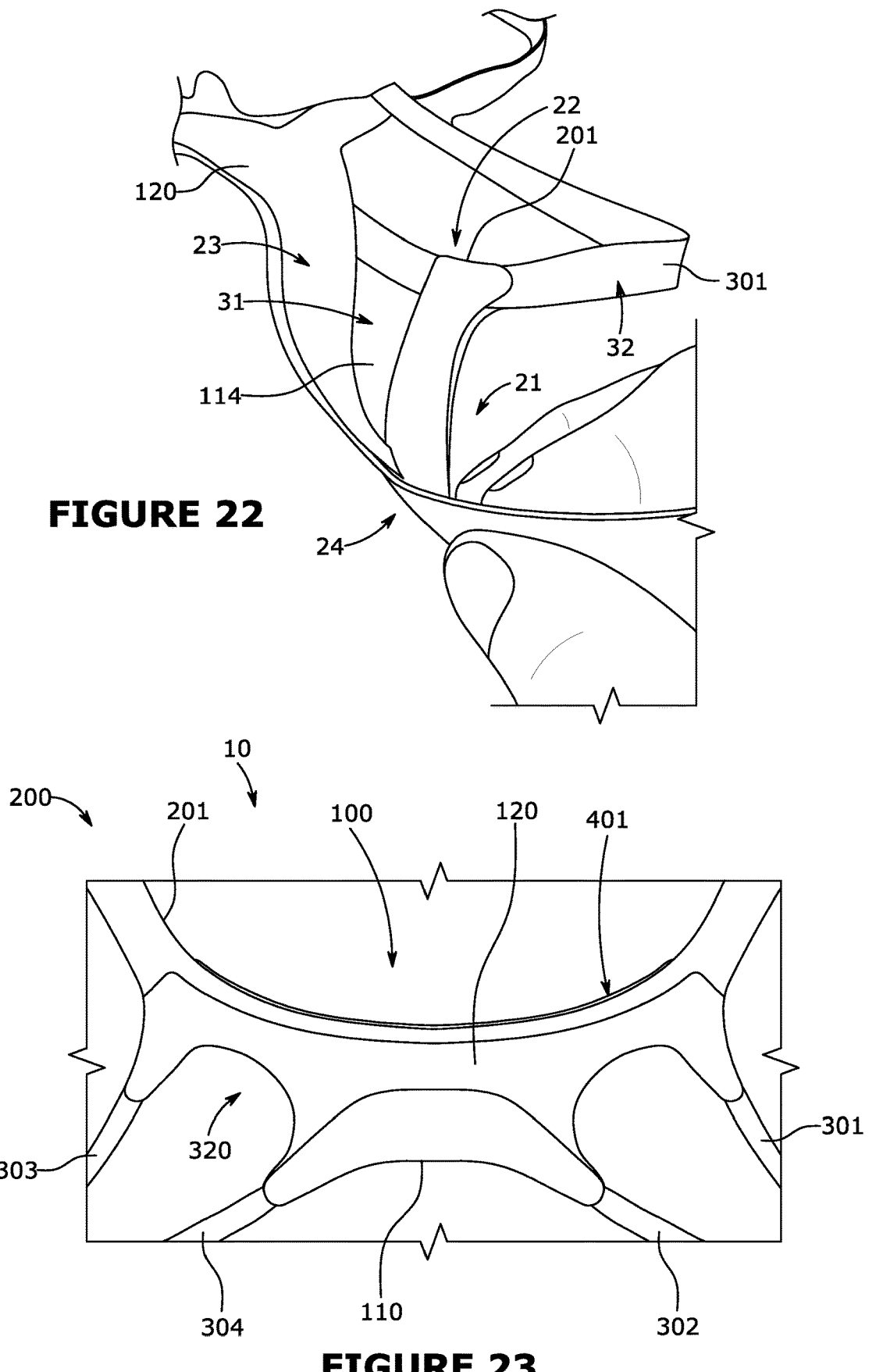
FIG. 22 is a close-up view of various lapped and non-lapped regions of part of a headgear.
FIG. 23 is a partial view of another headgear.

FIG. 22 shows another close-up of a region of the headgear of FIGS. 18-20, in particular the intersection of the crown strap panels 201 with the upper side strap 301.

Where the crown strap panels 201 singly lap each other defines a first lapped region 21 of the headgear. This first lapped region 21 may have a cross-section such as is illustrated in FIGS. 1A and 1B.

Where the crown strap panels 201 respectively overlap and underlap the upper side strap 301 defines a second lapped region 22. This second lapped region 22 may be in cross-section similar to the first lapped region 21 of the layup described in relation to FIG. 3B.

The second rear panel 120 and edge softening panel 114 may be singly lapped to each other to define a third lapped region 23.

The edge softening panel 114 between the third lapped region 23 and first lapped region 21 is not lapped by any other panel and defines a first non-lapped region 31.

The edge softening panel 114 may be lapped between the pair of crown straps panels 201 or may be lapped against the outer face of one of the crown strap panels 201.

At the fourth lapped region 24 the lapped together second rear panel 120 and edge softening panel 114 are at least partly lapped between the pair of crown strap panels 201. The cross-sectional configuration of the headgear at the fourth lapped region 24 may be similar to that described in relation to FIGS. 6A and 6, with two outer panels (the crown strap panels 201) overlapping and underlapping two other lapped panels (the second rear panel 120 and the edge softening panel 114).

FIG. 23 is a view of an inside surface of another embodiment of a headgear 10. As seen in FIG. 23, the rear portion 100 of the headgear has a first rear panel 110 of a relatively wider configuration than has been described in previous embodiments. The first rear panel 110 is singly lapped to the second rear panel 120.

The second rear panel 120 defines ear loops 320 of a substantially rounded configuration. The crown strap panel 201 is singly lapped across the top region of the second rear panel 120, with a portion of the second rear panel 120 extending past the crown strap panel 201 to define the upper peripheral edge 401 of the rear portion 100. This projecting portion of the second rear panel 120 may act as a rollaway edge as previously described.

As seen in FIG. 23, the lower side straps 302 and 304 connect directly to the first rear panel 110, at its lower portion where it is not lapped by the second rear panel 120. By this configuration loads from the lower side straps 302 and 304 will be transferred first through the relatively greater stretch first rear panel 110 before they are transferred into remaining relatively lesser stretch parts of the headgear. This may result in increased stretching of the rear panel 110 at its non-lapped region.

As seen in FIG. 23 the crown strap 200 may comprise a single crown strap panel 201 which is singly lapped to the second rear panel 120, or it may comprise a pair of crown strap panels 201 which lap either side of the second rear panel 120 (or the laminate of the first rear panel 110 and second rear panel 120, where the two panels are laminated to each other at this upper region of the rear portion 100).

Regardless of the configuration of the crown strap panel or panels 201, a portion of one or both of the first rear panel 110 and second rear panel 120 may extend past the crown strap panel or panels 201 to provide the previously described function of an edge softening panel 114.

Figure 24:
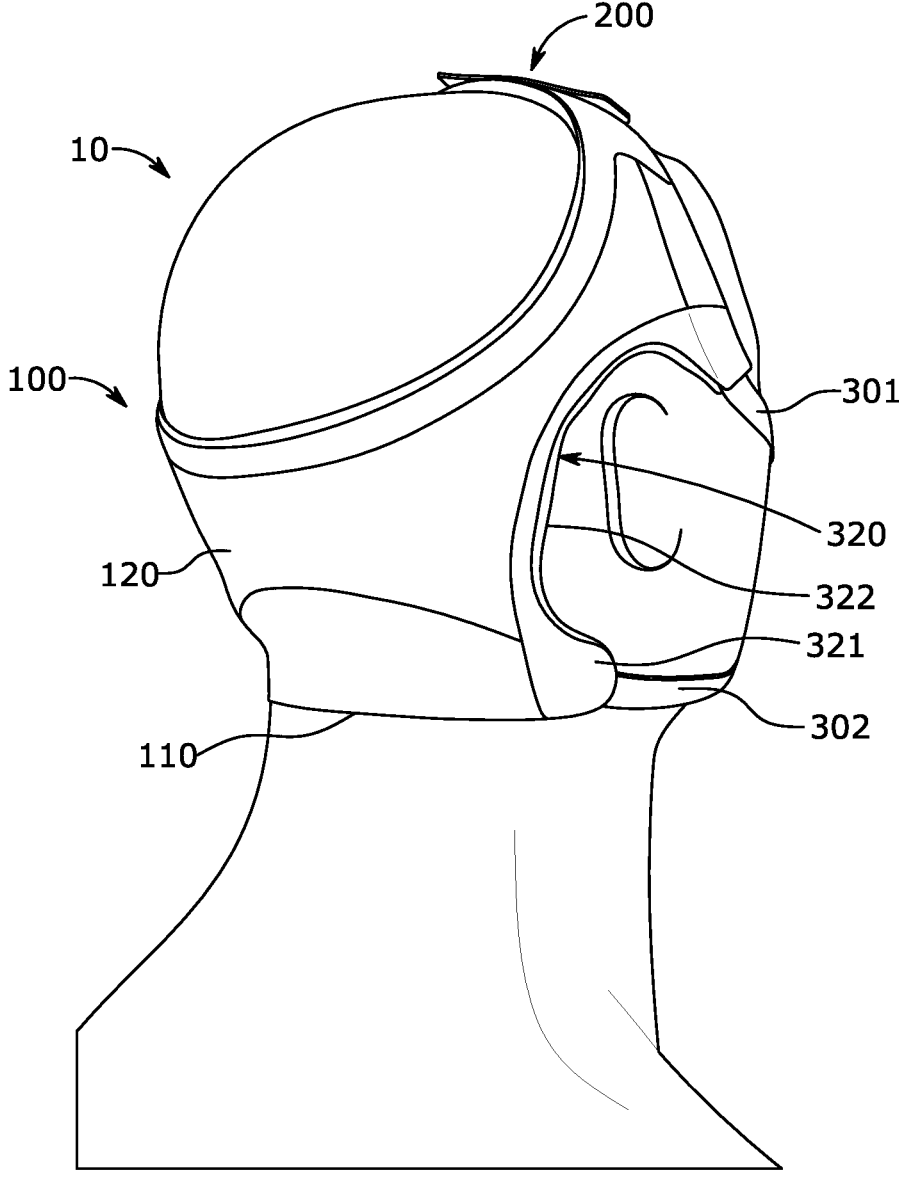
FIG. 24 is the headgear of FIGS. 23A and 23B on a patient's head.

FIG. 24 illustrates another embodiment of a headgear 10 on an example patient's head. Of particular note in the embodiment of FIG. 24 is the configuration of the headgear around the ear loops 321. At the ear loops 320 the headgear comprises an ear loop strap panel 321, which passes around the ear loop and connects between the upper side strap 301 and lower side strap 302.

This configuration of an ear loop strap panel 321 may be desirable to aid in transferring loads between the respective upper side straps 301 and 303 lower side straps 302 and 304 on each side of the headgear, such as to reduce of the load which is directly transferred to the first rear panel 110.

The ear loop strap panel 321, particularly as seen in FIG. 24 where it is a contrasting colour to the adjacent parts of the rear portion, may additionally provide a visual cue to the patient to distinguish this part of the headgear from others, and to prompt the correct orientation of the headgear for use.

In FIG. 24 the second rear panel 120 laps with the ear loop strap panel 321 and may extend beyond the ear loop strap panel 321 to a free edge 322 past the ear loop strap panel 321.

Figure 25A:
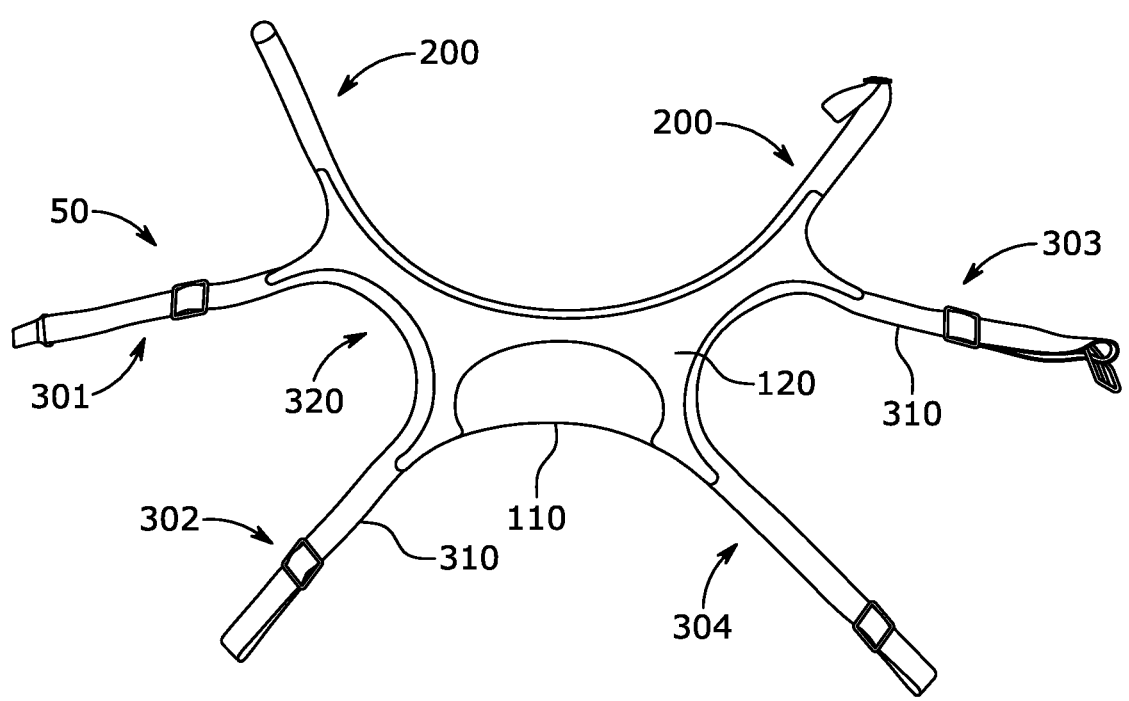
FIGS. 25A and 25B are respectively outside and inside views of another headgear.
Figure 25B:
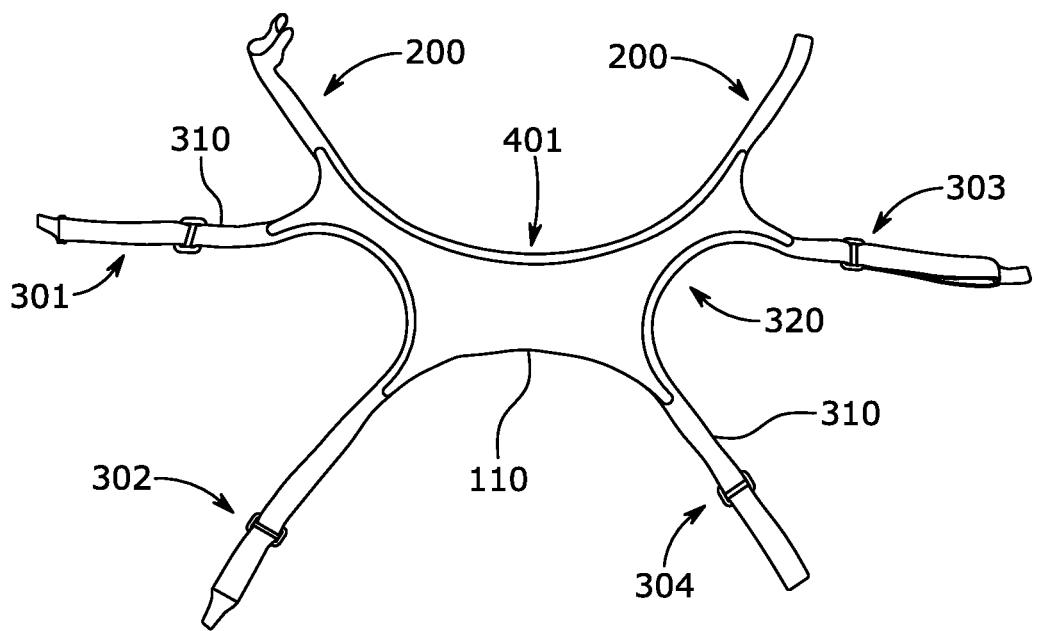

FIG. 25A is a view of an exterior surface 15 of another embodiment of the headgear, and FIG. 25B is a view of the internal surface 14 of the same embodiment.

In this embodiment, the upper side straps 301 and 303 and lower side straps 302 and 304, comprise one panel or laminate of panels which passes about and defines the ear loop 320.

The rear portion 100 comprises a first rear panel 110, which as previously described may be a panel of relatively greater stretch than other panels, or particularly other adjacent panels. The rear portion then comprises a second rear panel 120. The second rear panel 120 may be of relatively lesser stretch than the first rear panel. The second rear panel includes a cut-out to expose a portion of the first rear panel 110, which may provide a non-lapped region when the first rear panel 110 and second rear panel 120 have been bonded together.

As seen between FIG. 25A and FIG. 25B, the unitary strap panels 310 of each of the set of upper and lower side straps 301/302 and 303/304, are partially double lapped between the first rear panel 110 and second rear panel 120 about the ear loops 320. This double lapping of at least part of the unitary strap panels 310 at the ear loops 320 may be in cross-section similar to the configuration described in relation to FIG. 3B and may accordingly provide for similar advantages in strength of the panel connection and reduction of induced torques.

In the embodiment of FIG. 25 the second rear panel 120 is relatively extended, so that it forms the two sides of the crown strap 200. In this way it may replace the need for separate crown strap panels 20 as described in relation to various other embodiments herein.

As seen in FIG. 25B, the second rear panel 120 may similarly as previously described extend beyond the first rear panel 110 to which it is otherwise lapped, so that may form the upper peripheral edge 401 of the rear portion and function as a roll-away edge as elsewhere described.

Figure 26A:
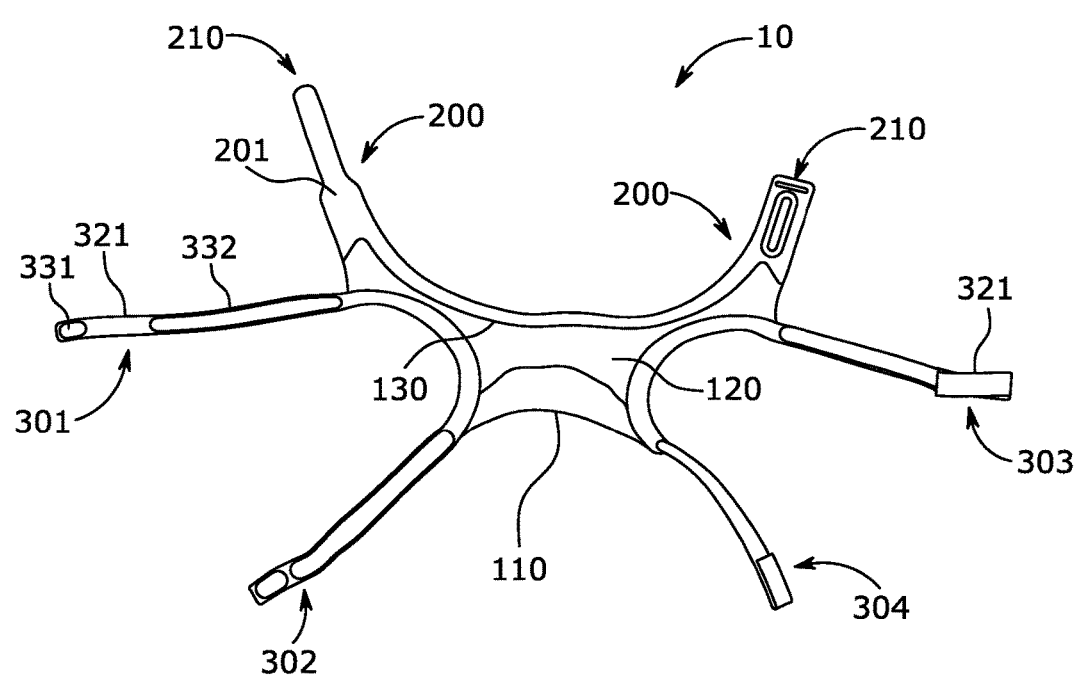
FIGS. 26A and 26B are respectively outside and inside views of another headgear.
Figure 26B:
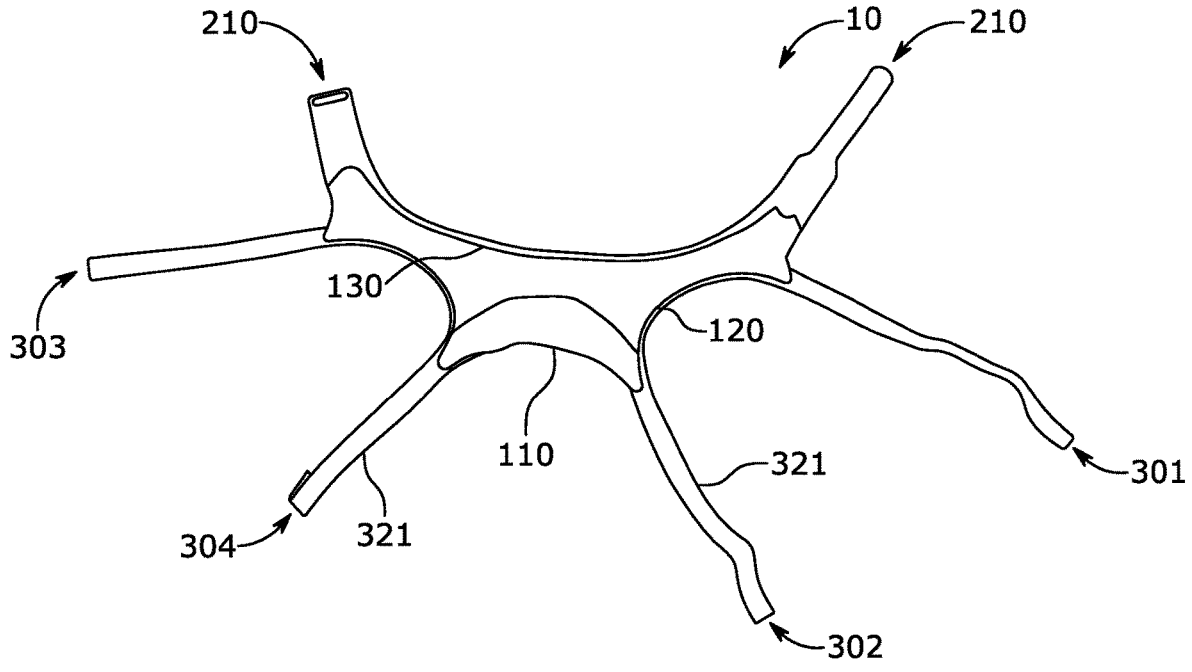

FIG. 26A is a view of an external surface 15 of a further embodiment of a headgear 10, and FIG. 26B is a view of an internal surface 14 of the same.

In this configuration the first rear panel 110 may only comprise a crescent shape and be lapped to the second rear panel 120 around the corresponding arc-shaped cut-out in it. The first rear panel 110 may be only singly lapped to the second rear panel 120, or there may be two second rear panels 120, and the first rear panel 110 may be double lapped between the two rear panels 120.

Where there are two second rear panels 120 and the first rear panel 110 is lapped between them, the first rear panel 110 may comprise only the exposed non-lapped region seen in FIGS. 26A and 26B and a lapped region sufficient to lap with and bond to the two second rear panels 120.

In other forms the first rear panel 110 may, but for the cut-out region of the second rear panel 120, substantially correspond to the size and shape of the second rear panel or panels 120. An example of this configuration is seen in first rear panel 110 and second rear panel 120 of FIG. 15.

Whether the first rear panel laps the second rear panel or panels 120 only around a small interface to form a bond or laps the substantial entirety of the second rear panel or panels 12, may be determined according to the nature of the respective panels and the structure and function which the headgear 10 is to perform.

In the embodiment of FIGS. 26A and 26B the unitary ear loop strap panels 321 are singly lapped to one face of the combined first rear panel 110 and second rear panel 120, rather than double lapped between them as described in relation to FIGS. 25A and 25B.

In the embodiment of FIGS. 26A and 26B the crown strap 200 is comprised by the crown strap panel 201, which may be lapped to the first and/or second rear panels 110 and 120.

As illustrated in FIG. 26A, one or more of the side straps 301-304 may include respective parts 331 and 332 of a fastener system by which the ends of the straps may be fastened back onto themselves. These may for example be respective halves of a hook-and-loop fastener system, such as with a hook part 331 and loop part 332.

In various configurations the loop part 332 may be provided as an additional component which is bonded to the underlying panel. In other configurations such as where the underlying panel is of an unbroken loop material having an uncut pile, the loops of the uncut pile of the panel itself may provide the loop part 332 of the hook and loop fastener system.

In various embodiments a headgear 10 may only comprise only one set of side straps 301 and 302, one strap each for connecting to a respective side of the respiratory interface.

Figure 27:
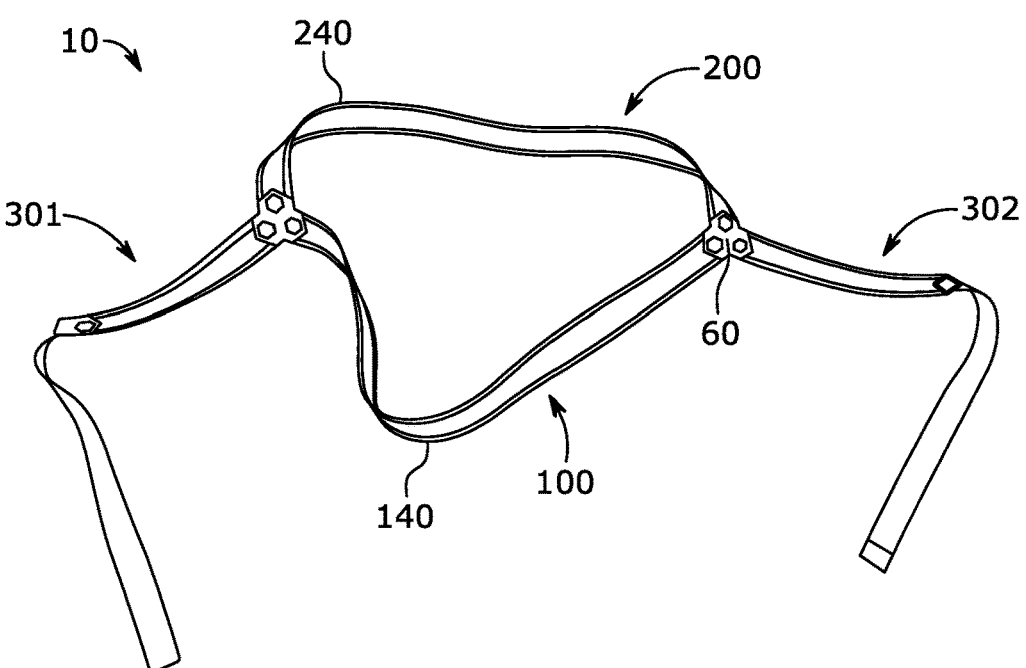
FIG. 27 is a view of another configuration of a headgear.

One such embodiment is illustrated in FIG. 27. The headgear 10 includes a rear portion 100, a crown strap 200, and a set of side straps 301 and 302. While the headgear may achieve the same functions as other embodiments described herein, particularly the crown strap 200 and rear portion 100 may be of a comparatively simplified form.

As seen in FIG. 27, the rear portion 100 comprises the rear panel 140 and the crown strap 200 comprises the crown panel 240. The rear panel 140 and crown panel 240 each meet at respective ends where they are joined with each other and with one end of a respective side strap 301 and 302.

As seen in FIG. 27, each of the rear panel 140 and crown panel 240, and at least portion of the side straps 301 and 302 proximal to the rear portion 100 and the crown strap 200, may comprise the same or substantially the same panel or panel layup configuration.

Where they are made of a similar panel layup, they may be made by the lamination together of a base panel 51 which is to define the inside surface 14 of the headgear and contact a patient's head in use, and another reinforcing panel 52. The reinforcing panel may have a relatively greater strength or stiffness than the material of the base panel.

The reinforcing panel 52 may be a continuous sheet which corresponds in dimensions to the base panel 51. In other configurations the reinforcing panel may be at least partially cut-out, such as is illustrated in FIG. 27. Providing the reinforcing panel 52 with cut-outs may reduce the weight of the combined panel layup. It may also only provide the strength or rigidity or other features of the material of the reinforcing panel 52 at regions of the base panel 51 where these characteristics are desired, for example along the edges of the panel layup.

As seen in FIG. 27, the reinforcing panel 52 may be solid along at least lateral edges and having an internal region which has one or more cut-outs.

The ends of the rear panel 140, crown strap panel 240, and a respective side strap 301 or 302 may be joined together at a join 70 by any suitable panel lapping configuration such as is described herein.

In particular, these panels may be joined together in a butt join, for example as was described in relation to FIGS. 7A-B and FIG. 8.

Figure 28:
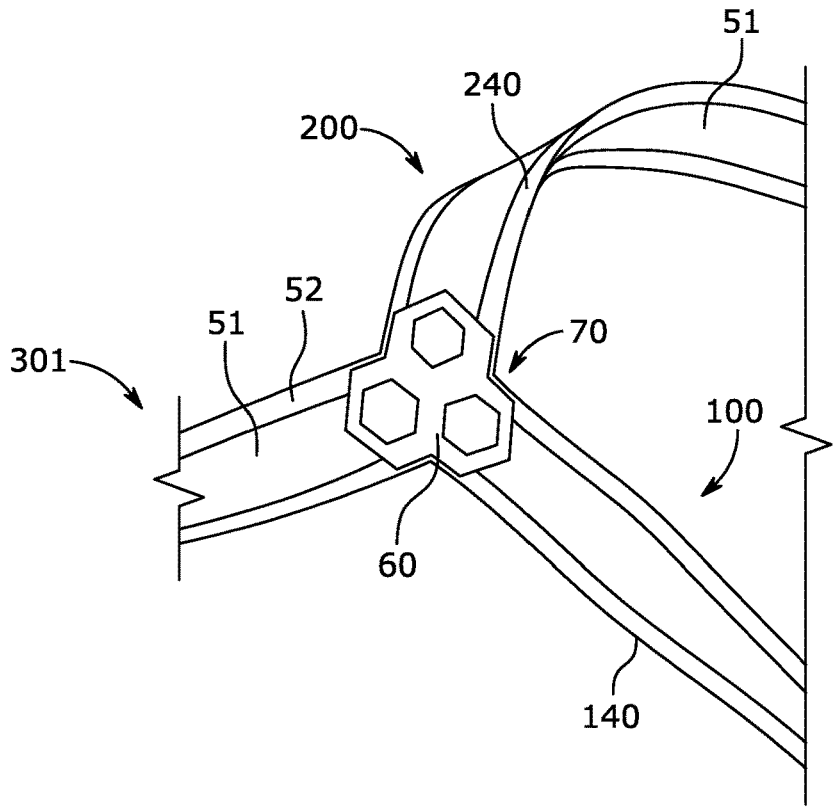
FIG. 28 is a close-up view of a joint portion of the headgear of FIG. 28.

FIG. 28 is a close-up view of the join 70 between the rear panel 140, crown strap panel 240, and a side strap 310. A respective end of the rear strap 140 and the crown panel 240 and side strap 301 may be aligned in at least the same plane if not also in end-to-end contact. A joint panel 60 may then lap each of the three other panels and be bonded to them at the join 70.

Such a joint panel 60 may be provided at only one surface, preferably an external surface, of the headgear, so as to provide an uninterrupted planar internal surface of the headgear at the join 70.

In other configurations two joint panels 60 may be provided, one to lap either major face of the three panels at the joint.

The use of a single joint panel 60 may provide for the connection of the three panels in a joint 70 having a layup thickness of only the joint panel 60 and the greatest of the thickness of the rear strap 140, the crown panel 240, and the side strap 301 or 302. This may provide for a thinner panel layup at the joint than would otherwise be possible by over and underlapping each of the different headgear panels together to form the join 70.

Figure 29A:
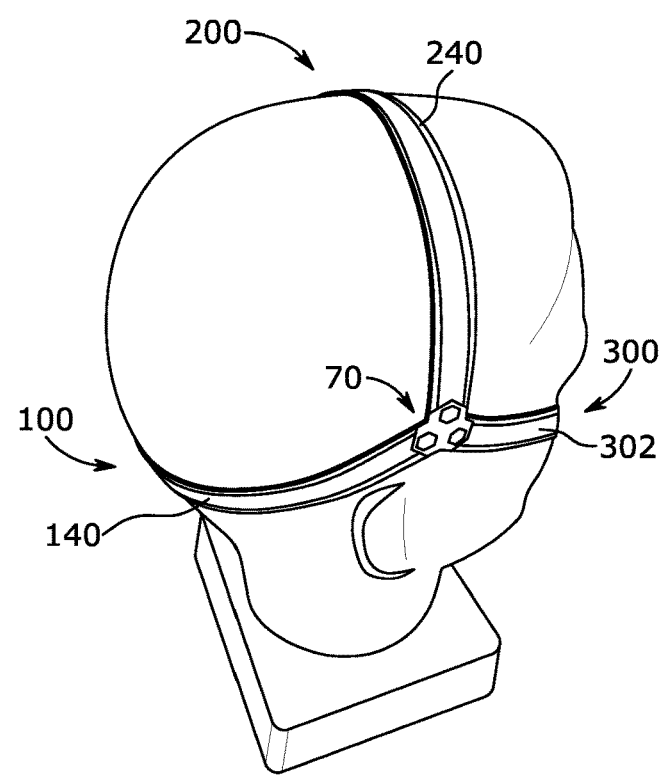
FIGS. 29A and 29B are views of the headgear of FIG. 27 on a patient's head.
Figure 29B:
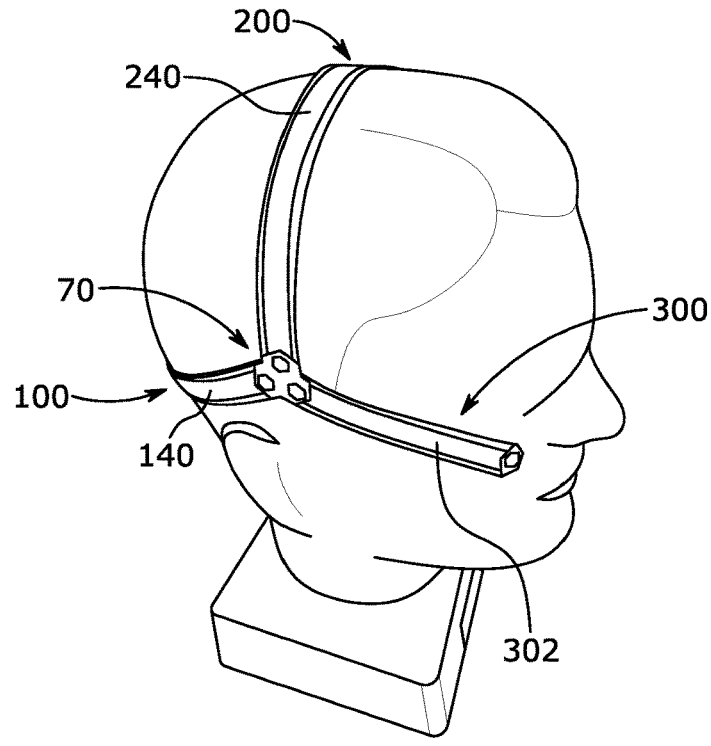

FIGS. 29A and 29B are views of a two-strap headgear such as of the embodiment of FIGS. 27 and 28 when on the head of an example patient.

As seen in FIGS. 29A and 29B, the join 70 may be configured to sit above the ear of the patient.

Figure 30:
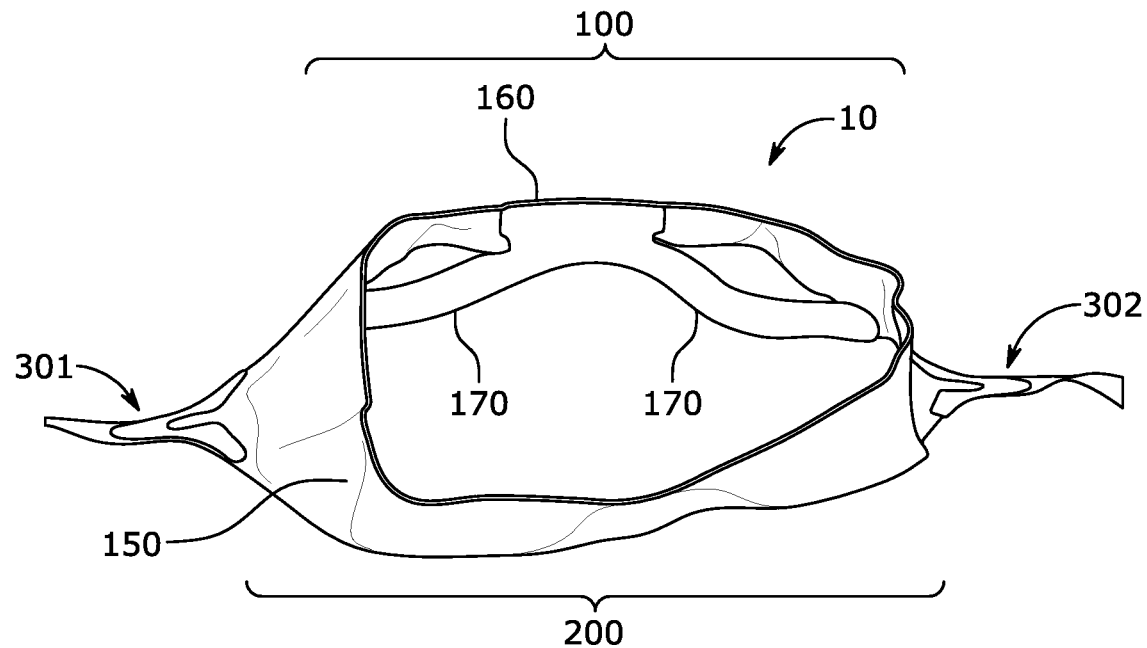
FIG. 30 is a view of another configuration of a headgear.

FIG. 30 illustrates a further embodiment of a headgear 10 having only two side straps 301 and 302.

As seen in FIG. 30, the rear portion 100 and crown strap 200 of this embodiment may comprise a continuous loop 150. The continuous loop 150 may comprise a single loop of material, a single panel which is bonded to itself, or a plurality of panels which are adhesively bonded together.

The side straps 301 and 302 depend from the respective lateral peripheries of the loop 150.

In FIG. 30 the loop 150 includes one or more panels of a first type, which may be a relatively decreased stretch material. More particularly it may be a non-stretch material and/or a non-elasticated material. It also includes an stretch panel 160 at the rear portion 100. The stretch panel 160 is of a relatively increased stretch than the one or more panels of the first type. The stretch panel 160 may act to allow the size of the loop 150 to expand and contract under load, and/or to conform to the shape of the patient's neck.

The stretch panel 160 may be an elasticated panel.

The loop 150 at the rear portion 100 may additionally comprise one or more lower stretch panels 170. These lower stretch panels 170 may connect between the stretch panel 160 and more lateral parts of the loop 150, particularly in the vicinity of where the side straps connect. These lower stretch panels 170 may in use be located lower on the rear of the patient's head than the remainder of the loop 150 and may act to provide further compensation for different patient head geometries in this area and additional stability of the headgear on the patient's head.

Figure 31A:
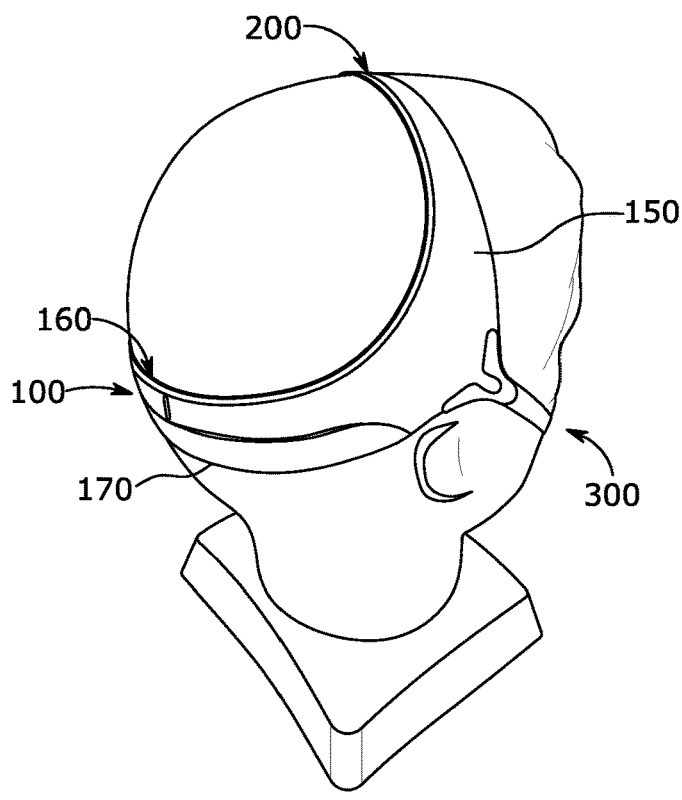
FIGS. 31A and 31B are views of the headgear of FIG. 30 on a patient's head.
Figure 31B:
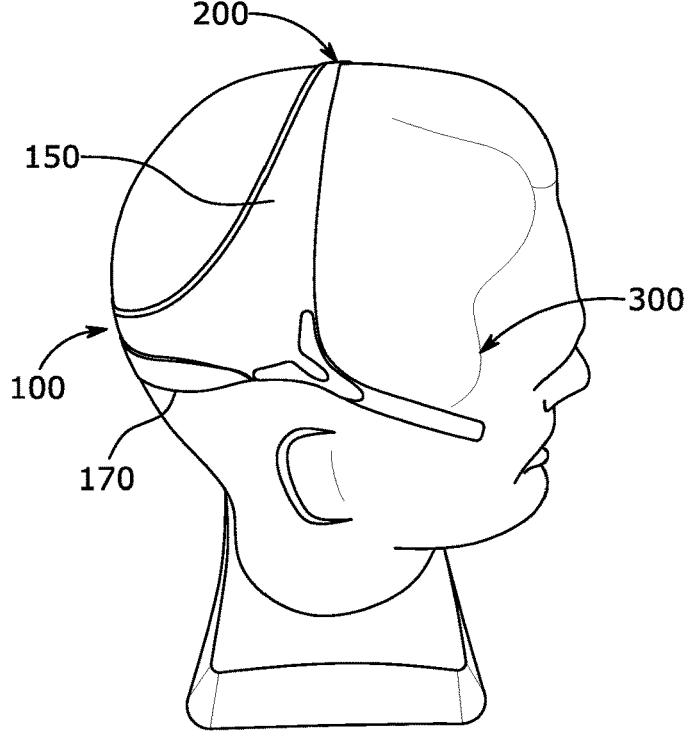

Various details of the headgear of FIG. 30 are shown in the views of FIGS. 31A and 31B, which are different perspectives of the headgear 10 of FIG. 30 on the head of an example patient.

As seen in FIGS. 31A and 31B, the loop 150 may be of a variable width. The loop may have relatively wider portions in the vicinity of the connection to the side straps and at least relatively narrower portions towards a top of the crown strap 200.

The side straps 300 of a headgear 10 may include one or more strap panels which are laminated together.

As elsewhere described, and as illustrated in for example FIG. 20, the ends of the side straps may pass through a fixture on the respiratory interface and fold back onto and fasten to themselves. To enable this there may be a two-part fastener system provided on the side strap, such as a hook-and-loop fastener.

However, when tightening a side strap back against itself it may be desirable to provide some form of feedback to the patient as to how tight the mask is and/or to provide some regular steps to which the straps may be adjusted to aid in easily equalising the amount that different straps are tightened.

Figure 32A:
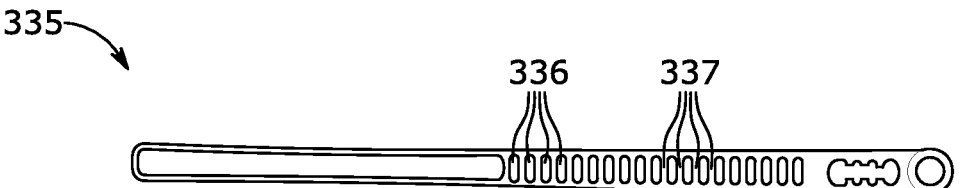
FIG. 32A is a panel for part of a strap.

FIG. 32A shows an index panel 335 which is to be laminated onto a base panel 310 to form a side strap. The index panel 335 includes at least a series of step-like formations 337 which extend at least partially between the two sides of the index panel 335.

The index panel 335 may comprise a material which is relatively stronger, stiffer, denser, and/or harder than the underlying base panel 310 to which it is to be laminated.

Figure 32B:
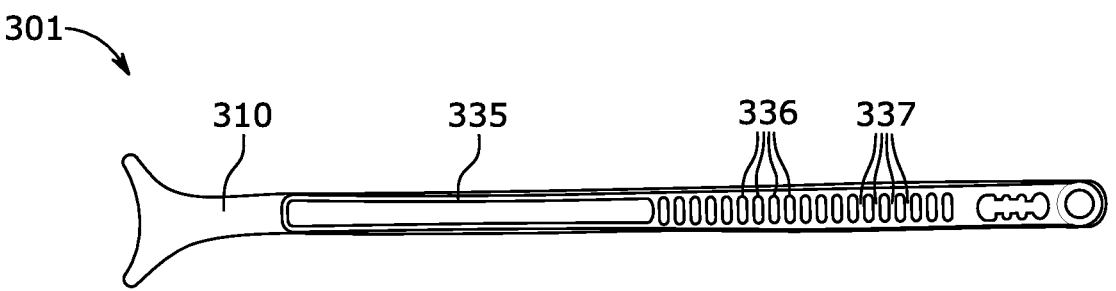
FIG. 32B shows the panel of FIG. 32A bonded to another strap panel.

FIG. 32B illustrates the index panel 335 of FIG. 32A laminated to a base panel 310.

By providing the index panel 335 on the external surface 15 of the headgear relative to the base panel 310, the index panel 335 may come in contact with a fixture of the respiratory interface as the strap end is passed through it and pulled back towards the rear portion 100 of the headgear.

When there is tension on the two sides of the strap 301 across the fixture of the respiratory mask, the step formations 337 of the index panel 335 may provide tactile feedback to the patient as the straps are tightened on the respiratory interface.

A further function of such an index panel 335 which is of a relatively stronger, stiffer, denser, and/or harder material than the base panel 310 may be to provide wear resistance to the strap 301 as it engages with and passes over the fixture of the respiratory interface. For at least this purpose, a strap may include an index panel 335 without the defined cut-outs 336 to provide tactile feedback but may instead have a substantially continuous panel 335 without cut-outs.

Figure 33:
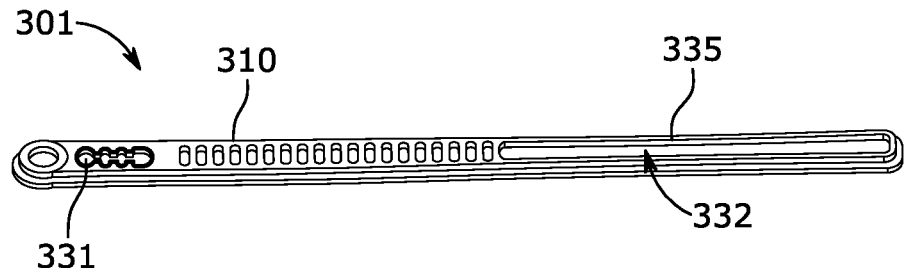
FIG. 33 shows another laminated strap panel.

FIG. 33 illustrates a further configuration of a side strap 301 which includes a base panel 310 and an index panel 335 laminated to it.

As seen in FIG. 33, a distal portion of the strap 301 has within cut-outs of the index panel 335 a first part 331 of a fastener system which corresponds with second part 332 of a fastener system. The second part 332 may be provided by the material of the base panel 310 itself, or by another material laminated thereto.

While shown in FIGS. 32A-B and 33 as comprising a unitary panel with a plurality of cut-outs 336 to define the step formations 337, according to other embodiments the index panel 335 may be provided just as the step formations 337. In other words, the index panel 335 may instead comprise a plurality of step formations 337 without any linking material to define a single unitary panel.

The step formations 337 preferably present a raised surface above the surface of an underlying strap panel, such that the step formations provide resistance to movement of the strap relative to the interface. The spacing of the step formations may provide for an indication of indexing of each strap by a patient as they adjust the tension on the headgear straps.

To provide the indexed resistance the step formations 337 may be of a different and preferably harder or denser material than that of the underlying strap panel.

As previously described particularly in relation to FIGS. 11A-13B, various panels of the plurality of panels of the headgear may be given various edge treatments to provide different properties to one or more of the edge regions. Changes to the properties of an edge or edges of one or more panels may also influence the overall properties of the headgear.

Figure 34:
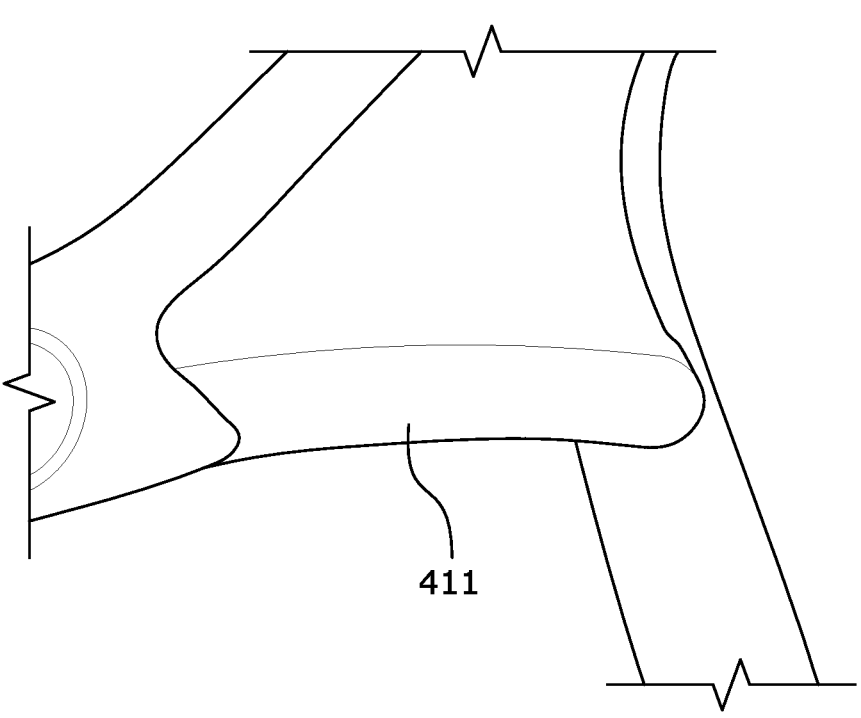
FIG. 34 shows a close-up view of a headgear.

FIG. 34 illustrates an example of a rolled-back hem 411, such as is shown in section view in FIGS. 13A and 13B.

At the rolled-back hem 411 the panel or laminate of panels have been rolled back a distance onto themselves and bonded thereto by an adhesive.

Figure 35:
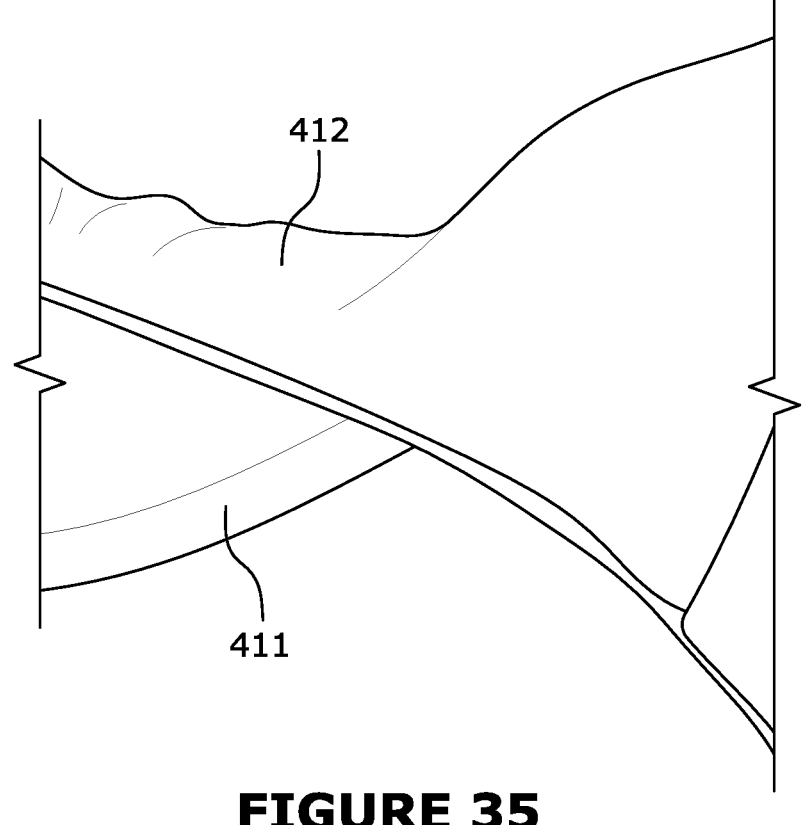
FIG. 35 shows another close-up view of a headgear.

A further example of a rolled-back hem 411 is shown in FIG. 35, showing a close-up view of another part of an embodiment of a headgear 10.

A rolled-back hem 411 may provide for an effective doubling of the thickness of the panel or laminate of panels at the edge. The thickness may be further increased by the presence of the adhesive between the panel and its rolled-back portion.

In addition to increasing the thickness at the edge region, a rolled-back hem 411 may also increase the strength of the panel or laminate of panels at the edge region. As previously described, the properties of the adhesive may be customised to contribute desired properties to at the rolled-back hem 411. For example, the adhesive may be stiffer than the panel or laminate of panels, or it may be of substantially the same stiffness as the panel or laminate of panels at the rolled-back hem 411.

As loads may be concentrated at edge regions of panels the use of a rolled-back hem 411 may allow for the whole panel or laminate of panels to have reduced thickness or reduced strength requirements, but to still be able to service the same loads due to the strengthened edge region.

While generally described and shown as being at a peripheral edge of the headgear, a rolled-back hem 411 or any other edge conditioning may be provided at other non-peripheral portions of the headgear.

FIG. 35 also illustrates the application of an edge conditioning method previously described in relation to FIGS. 11A to 12B. The panel or laminate of panels at the treated edge 412 may be treated on one or both major faces with an adhesive. Particularly where this adhesive when set has greater stiffness than the panel or laminate of panels to which it is applied, the result may be to provide the panel or laminate of panels at the stiffened edge 412 with an increased stiffness. In other configurations the treatment may perform other functions in addition to or instead of increased stiffness, for example it may aid in preventing an unravelling of the panel material at the edge.

The ends of the side straps 300 are in use to be grasped by a patient, passed through a fixture of the respiratory interface, and then attached back onto themselves or otherwise secured to provide tension to retain the respiratory interface to the patient's face.

As a patient is to grasp the ends the side straps, it may be desirable to provide for strap ends which are able to be easily differentiated from the remainder of the strap by either or both of visual and tactile differentiation.

To this end, in some embodiments the ends of one or more of the side straps 300 may be lapped by one or more additional panels to form a strap-end feature 350.

By being lapped by one or more additional panels the strap-end feature 350 may have a different thickness to that of a strap panel 310, and thus be identifiable by touch by a patient.

In addition to or alternatively to a physically identifiable difference in thickness, the strap-tab feature may have a different colour, texture, softness, or other surface characteristic.

Figure 36A:
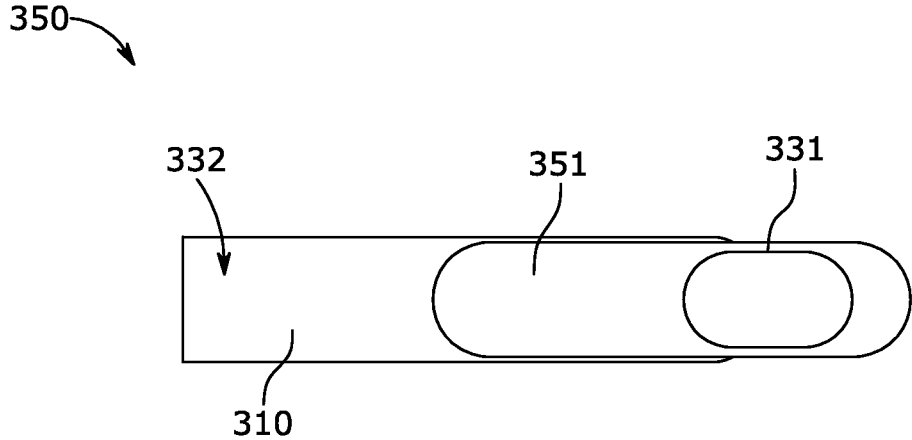
FIGS. 36A and 36B are top and side views respectively of a strap end feature.
Figure 36B:
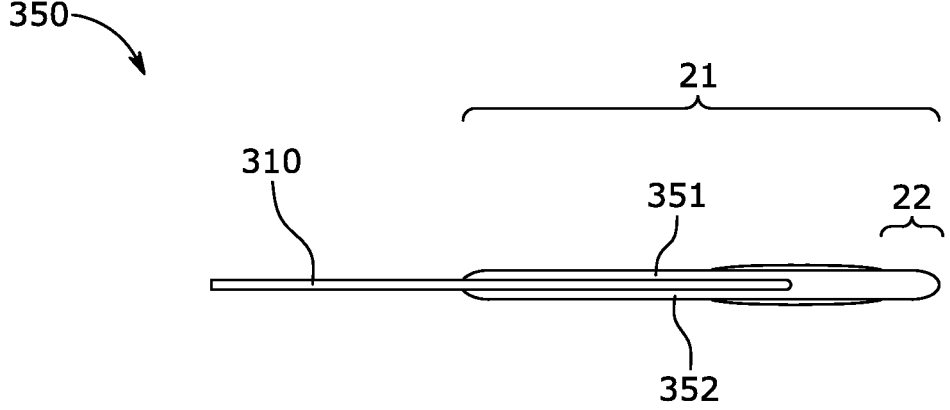

An example of such a strap-end feature 350 is illustrated in FIGS. 36A and 36B. As seen in FIG. 36A, the strap-end feature 350 may include a first tab panel 351 which is at least partially lapped to the strap panel 310. As seen in FIG. 36A, the first tab panel 351 has a greater surface smoothness than that of the strap panel 310, and thus may be able to be distinguished from it by touch.

On top of the first tab panel 351 is a first half 331 of a hook and loop fastener. In some embodiments the outer surface of the strap panel 310 may form the second half 332 of the hook and loop fastener, to engage the strap end with the strap when the strap end is folded back onto itself.

As seen in the configuration of FIG. 36A the strap panel 310 may integrally comprise the second half 332 of the hook and loop fastener. For example, the strap panel 310 may be of an unbroken loop material, and loops presented at the surface of the strap panel 310 may be utilised as the loops of the hook and loop fastener.

The strap panel 310 may be singly lapped by the first tab panel 351, or it may be lapped on its other major face by a corresponding second tab panel 352, as is illustrated in the side view of FIG. 36B.

While the presence of a first and/or second tab panel 351 and 352 may provide a desired degree of ability to differentiate between the strap end and the remainder of the strap, adhesive may be utilised to enhance this differentiation.

For example, the adhesive may provide the strap end feature 350 with an increased stiffness relative to the strap panel 310. This difference in stiffness may act the or an additional physical cue to the patient as to the presence of the strap end.

The first and second tab panels 351 and 352 may be fully lapped against the strap panel 310 to provide a three-panel laminate, such as is shown at the first lapped region 21 of FIG. 36B.

In other configurations the tab panels 351 and 352 may extend distally of the end of the strap panel 310, as is seen in FIG. 36B, to form a second lapped region 22.

The difference in thickness between the first lapped region 21 and second lapped region 22 may provide a further tactile cue for patient as to the location of the end of a strap.

Where the tab panels 351 and 352 comprise a second lapped region 22 at which they only singly lap each other, rather than lap either sides of the strap panel 310, an additional amount, or different type, of adhesive may be utilised at the second lapped region 22. This may provide the second lapped region 22 with an increased stiffness relative to that of either the first lapped region 21 or the strap panel 310 by itself and may be another potential form of cue to a patient that they are grasping the tab ends.

While various embodiments of the headgear may have a 2D shape and be able to lay flat or substantially flat on a flat surface, some embodiments of the headgear may have a 3D shape such that it does not lay flat on a flat surface.

Such 3D shapes may be provided by a shape of one or more of the panels before they are lapped and joined together.

A 3D shape may additionally or alternatively be provided to part or all of the headgear once some or all of the panels have been lapped with each other.

For example, the panel or panels, either before or after they are joined together, may be placed inside a 3D mould to provide a 3D shape to the panels, such as by a stretching and/or a melting of the panels.

Figure 37:
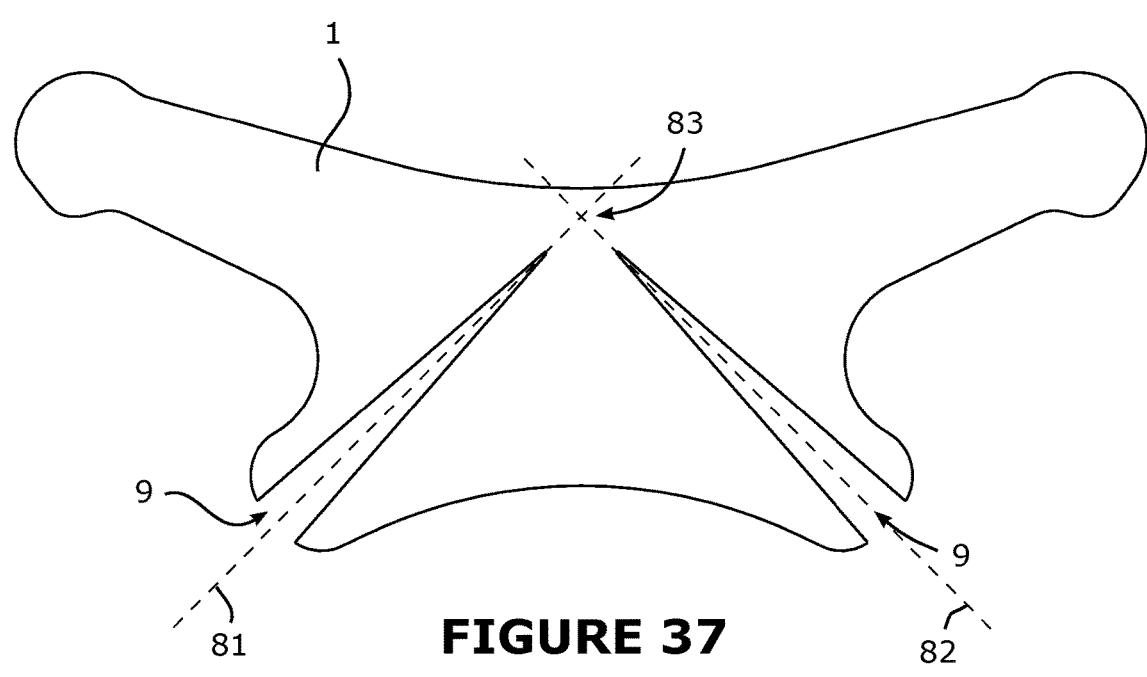
FIG. 37 shows a panel for a headgear.

FIG. 37 shows a view of a first panel 1 which includes two darts 9. As seen in FIG. 37 the darts 9 are tapered slots that have been formed in the first panel 1. The tapered slots are widest at an edge of the panel and decrease in width as they extend into the panel.

When the parts of a panel such as the panel 1 of FIG. 37 are gathered together across a dart the panel will be drawn into a 3D shape.

The sides of a dart may each define single straight lines, so the width of dart tapers linearly along its length.

In other forms one or both of the sides of a dart may define more than one straight line segment, so the width of the dart tapers linearly along each straight-line segment but not along the entire length of the dart.

In still other forms one or both of the sides of a dart may have one or more non-straight-line segments, so the width of the dart tapers non-linearly along its length.

One or more combinations of such configurations in one dart or a plurality of darts may be utilised in order to provide a panel or the headgear with a desired 3D shape.

While the darts 9 of FIG. 37 are tapered slots formed into the first panel 1, in other forms one or more darts may be formed by a folding of the panel along the sides of the dart. No slots are formed in the panel in such embodiments.

Figure 38A:
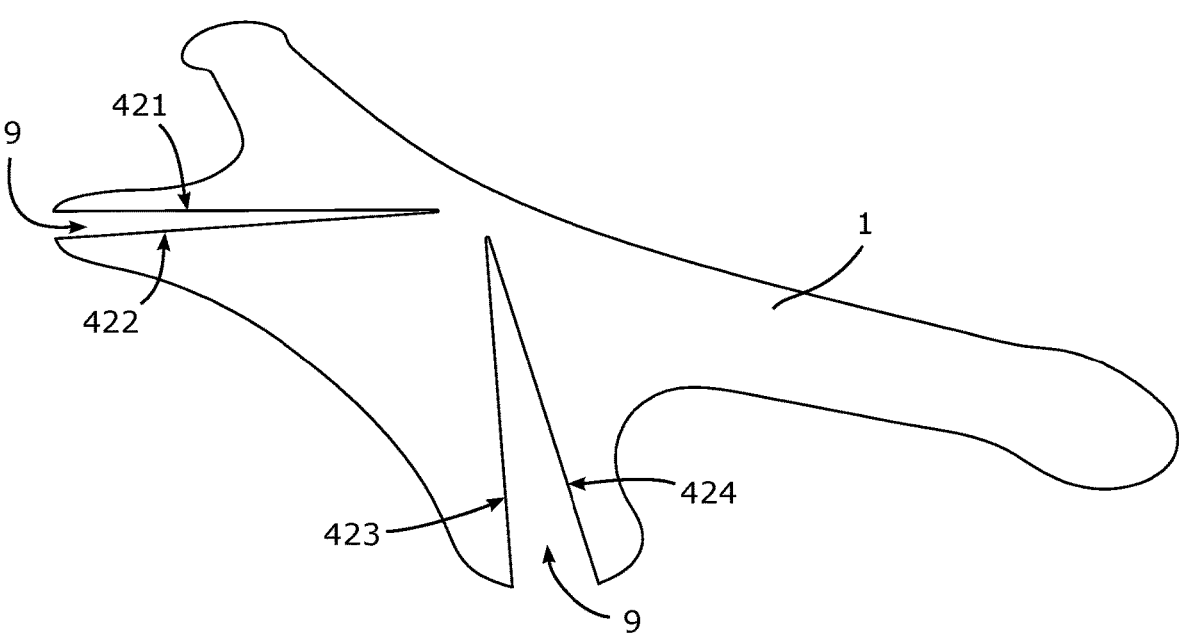
FIG. 38A shows another view of the panel of FIG. 37.
Figure 38B:
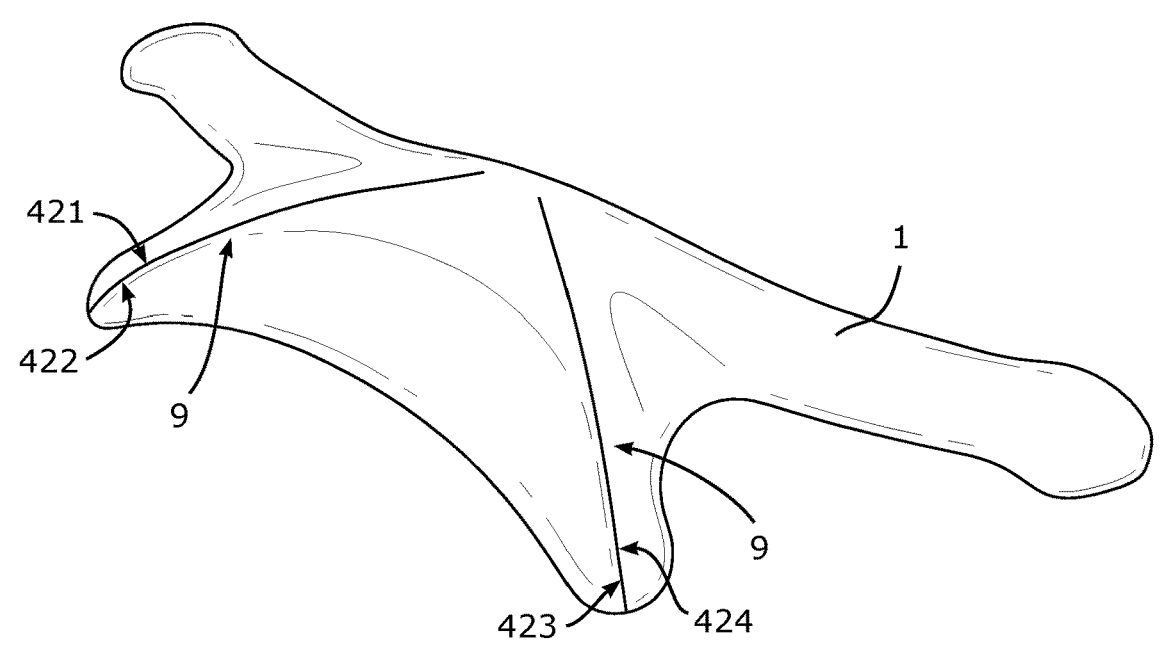
FIG. 38B shows the panel of FIG. 38A in a 3D configuration.

FIG. 38A shows a perspective view of the panel 1 of FIG. 37, and FIG. 38B shows the same panel 1 where the respective sides 421 and 422, and 423 and 424, of the darts have been drawn together.

The drawing together of the sides of darts where the darts are formed as a slot of the panel may close the slot and redefine a panel surface without gaps in it.

The drawing together of the sides of darts may involve the respective sides, such as the sides 421 and 422, and 423 and 424 of FIGS. 38A and 38B, being brought to or at least towards edge-to-edge contact.

In other forms, the sides of one or more darts may partially or wholly respectively overlap and underlap each other when they are drawn together. Where drawn together such that the dart sides overlap and underlap each other, a relatively greater 3D deformation of the panel may be affected than where the sides are just brought to or towards edge-to-edge contact.

As seen in FIG. 38B the gathering of the panel at the respective sides 421 and 422, and 423 and 424 of the darts 9 causes the panel to assume a 3D shape.

When the darts 9 are closed, the parts of the panel either side of the dart sides are rotated around a focal point of the dart at a point of the tapered slot. As the darts 9 are widest at the lower edge of the panel away from the upper side of the panel with its two lateral extensions, when the darts 9 are closed the bottom part of the panel 1 decreases in lateral size the most. The decrease in lateral size progressively reduces along the length of the dart 9.

As a result, the panel 1 which may previously have been of a 2D shape is drawn into a 3D shape as the darting induces out-of-plane curvature of the panel.

As seen in FIGS. 38A and 38B, the panel 1 has two darts 9. The darts each extend from their widest part at a relatively more lateral part of the panel and towards a relatively more central part of the panel. The darts 9 each both extend from a lower part of the panel 1 towards an upper part of the panel.

The centrelines 81 and 82 of the two darts 9 are shown in FIG. 38A.

As seen in FIG. 37 the two darts are located so that the extension of their centrelines 81 and 82 beyond their narrowed ends intersect with each other at the notional intersection point 83.

In other forms the centrelines of two or more darts may extend parallel to each other or diverge from each other. Where the centrelines of two darts meet at a notional point of convergence, this point may be located on the panel, as in the configuration shown in FIG. 37 or may be located outside the extents of the panel. As seen in FIG. 37 the notional point of convergence is located on a central vertical axis of the panel.

As seen in FIGS. 37 and 38A and 38B, the darts 9 are arranged to cause the panel 1 to assume a convex shape at one side, the side visible in FIG. 38B for example, and a concave shape at the other side of the panel.

The gathering of the panel 1 at the two darts 9 which taper towards each other causes the panel 1 to assume a 3D curved shape in at least the part of the first panel 1 between the two darts 9 and laterally adjacent regions of the panel either side of the darts. Particularly, it may define a 3D curved surface which decreases in radius from a lower extent of the panel towards an upper extent of the panel.

By the incorporation of one or more darts one or more panels of the headgear may be formed into a 3D shape. The 3D shape may be any desired shape, but particularly a shape or shapes which may correspond to the shape of the head of a patient where the headgear is intended to be located in use.

A headgear having a 3D shape may provide increased comfort for a user, and particularly potentially a reduction in locations of pressure concentration as may occur where a 2D headgear stretches to conform to the 3D shape of a patient's head.

A headgear having a 3D shape may provide increased stability and reduced deformation of the headgear from a non-worn shape. The reduced degree of deformation of the headgear in use may decrease the likelihood of any slipping of the headgear relative to the patient's head, or of curling or folding of the headgear during use. As a more stable headgear may be provided, it may be possible to reduce an amount of material needed to form the headgear and accordingly decrease the bulk and/or weight of the headgear.

A headgear having a 3D shape may also better signal a desired orientation and/or positioning of the headgear to the patient.

A darted panel may be joined together at the darts to make a 3D shape by for example the application of a tape or particularly adhesive tape at the darts, by welding of the dart sides together, or by stitching.

In other forms the darted panel may be placed in a 3D mould corresponding to the darted 3D shape of the panel. One or more other panels may then be lapped with the darted panel to at least partially cover the darts and joined to it by any of the methods described herein, including particularly by the use of an adhesive or adhesive tape.

Figure 39A:
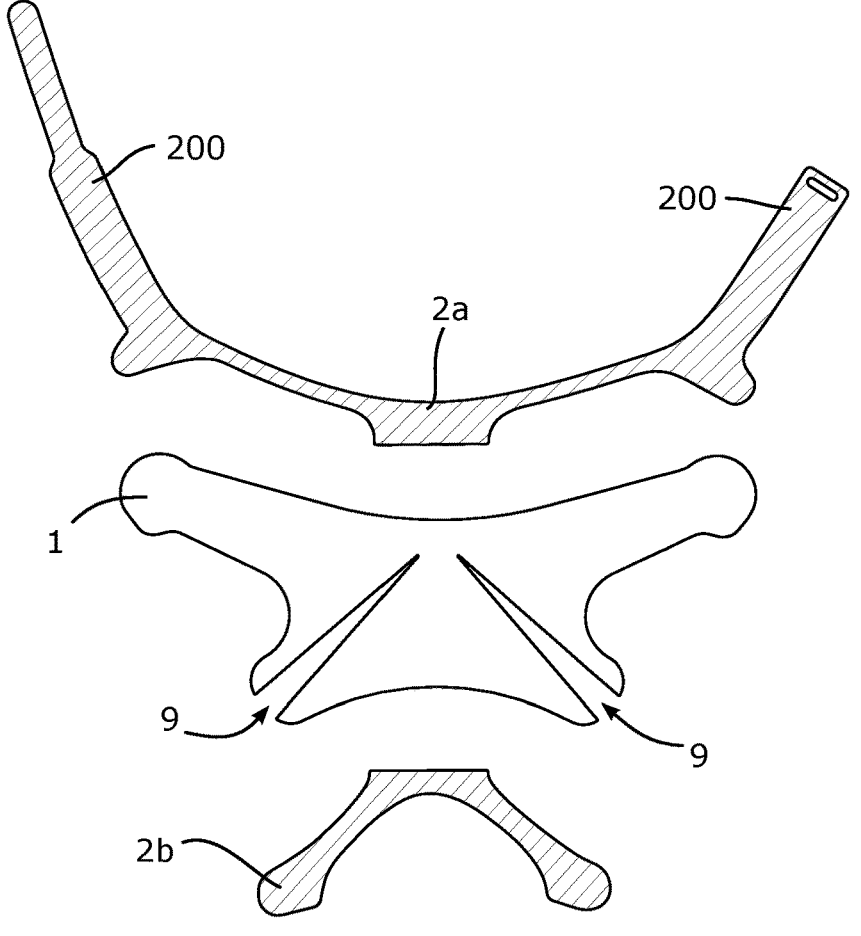
FIG. 39A shows various panels for forming a headgear.

FIG. 39A shows a first panel 1 with two darts 9, and a second panel 2 provided in two parts 2*a* and 2*b*. The second panel parts 2*a* and 2*b* are to be overlaid on the first panel in order to form the headgear.

As seen in FIG. 39A the second panel 2 includes the two parts of the top strap 200.

In various forms one or the other of the panels may include parts to fully or partially define one or more of the straps 301-304 or 200.

While shown in FIG. 39A as being provided in two parts 2*a* and 2*b*, the second panel 2 may be provided as a single piece, or as more than two pieces.

FIG. 39B shows a view of the first panel 1 with its darts 9 closed to form a 3D shape, and the first panel is lapped by the two parts 2*a* and 2*b* of the second panel 2. As seen in FIG. 39B the second part 2*b* of the second panel is sized and shaped to overlap the darts.

The second part 2*b* may cover the darts 9 to visually obscure them and present a seamless surface at that side of the headgear.

The second part 2*b* may at least in part aid in retaining the darts 9 in a closed position by bonding of the second part 2*b* to the first panel 1.

While shown in FIG. 39B as overlapping the closed darts, a panel which laps the first panel 2 may not overlap part or all of one or more of the darts.

Where the darts are not lapped by another panel, they may be secured closed such as by one of the previously described dart closure methods.

As seen in FIG. 39B the second panel parts 2*a* and 2*b* assume a 3D shape on the first panel 1, to define a headgear 10 having a 3D shape. To ensure any non-darted panel smoothly assumes a 3D shape the panel may be selected to be at least relatively extensible.

In some forms a panel which laps a darted panel, such as the second panel 2 in FIG. 39B, may be of a stretchable material such that it conforms to the shape of the darted panel with minimal or no wrinkling.

FIG. 39C illustrates another view of a 3D headgear 10. In the configuration of FIG. 39C the location of the two top strap parts 200 are switched from that of the headgear 10 of FIG. 39B.

As seen in FIG. 39C the darts 9 of the first panel 1 are such as to cause the headgear to have an internally concave surface at its rear portion 100, such as may correspond to the shape of the rear of a patient's head.

While shown in FIGS. 37-39A-C as having the second panel 2 lapped to the first panel 1 at an external side of the headgear, where the first panel 1 has a convex shape, it will be appreciated that the second panel may instead be lapped to the inside surface of the headgear. Similarly, both sides of the first panel 1 may be fully or partially lapped by other panels.

A panel which is darted may be overlaid with a non-darted panel or panels, such as is illustrated in FIGS. 39A-C.

In other forms, multiple darted panels may be overlaid on each other.

Where multiple darted panels are overlaid on each other they may be darted so that one or more of their darts align with each other when the panels are in their desired lapped placement.

In some forms where multiple darted panels are overlaid on each other at least some or even all of their darts may not align with each other. This may provide for relatively increased strength of the headgear. Where the joining of the panels at their darts results in a seam or region of increased thickness, this may also provide for a reduction in the thickness of the headgear.

A panel which is darted will be caused to deform when its darts are closed. If the panel is extensible, at least part or even all of the deformation of the panel as a result of its darting may be experienced in-plane rather than out-of-plane to form a 3D shape.

Accordingly, at least one darted panel in a headgear may be of a limited extensibility to ensure a desired amount of out-of-plane deformation occurs due to its darting.

While shown in FIGS. 37-39A-C as including a first panel 1 having two darts 9, it will be appreciated that one or more panels may include one or more darts, such allow for the desired 3D shape of the headgear. The darts may extend either further into or less far into a panel than is illustrated of the panel 1 of for example FIG. 37. The darts may also have a relatively lesser or relatively greater angle between their adjacent sides. These parameters may be configured such as to provide the desired shape to a headgear, including particularly a shape corresponding to the shape of a patient's head.

In other forms the panel or panels to form a 3D shape may be provided in multiple pieces which when their adjacent edges are brought together define a 3D shape.

As illustrated in FIGS. 37-39 a dart may be a tapered slot formed in a panel. As previously described, a dart may also be a tapered fold made in a panel, where the material within the tapered region is not removed to define a slot.

More generally a dart may be provided by any in-plane rotation of part of a panel relative to another part of a panel, about an axis normal or substantially normal to the surface of the panel.

Such rotation is provided by the darts 9 of FIGS. 37-39 when they are closed, as the lateral parts of the panel 1 are rotated relative each other towards the central part of the panel.

While an in-plane rotation of part of a panel relative to another part of the same panel may be affected by closing one or more slot-like darts formed in a panel, it may also be provided by the joining together of edges of different panels or panel parts.

Figure 40:
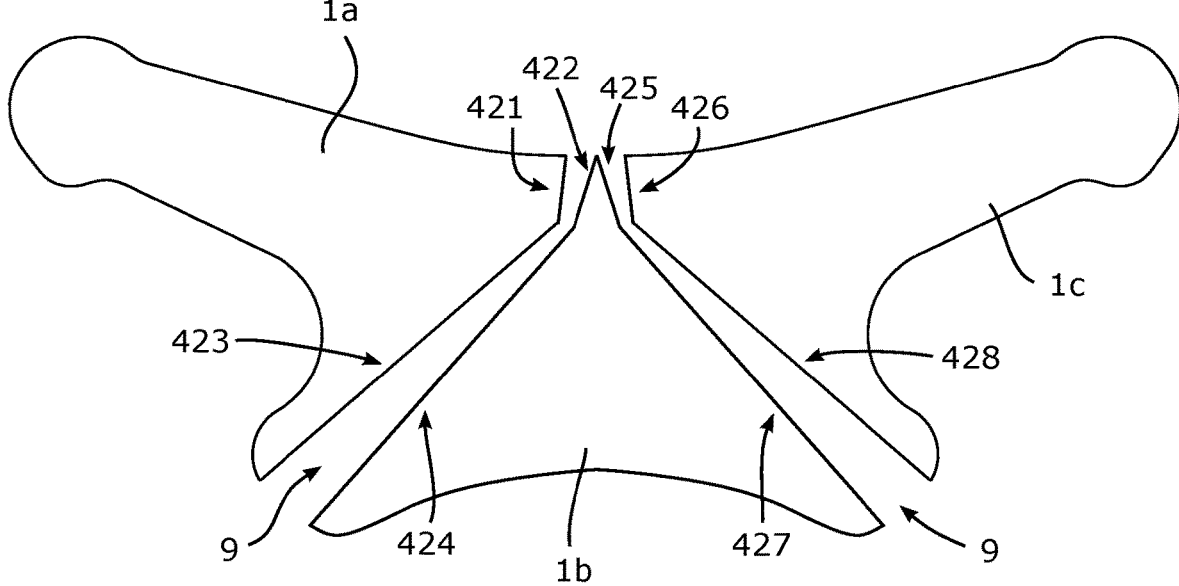
FIG. 40 shows another embodiment of a panel for a headgear.

An example of this is seen in FIG. 40 where a first panel 1 is provided in three parts 1*a*-1*c*. The shape of each of the parts 1*a*-1*c* is such that their edges 421-428 cannot all be brought together without causing a deformation of one or more parts of the panel.

When their adjacent edges 421-428 are aligned with each other one or more of the panel parts will be caused to deform to a 3D shape.

The 3D shape of the panel parts 1*a*-1*c* of FIG. 40 when the adjacent edges 421-428 are brought together may be configured by control of the length of each edge and their angles relative to each other to provide the same 3D panel shape as may be provided by a panel with darts defined by tapered slots, such as that of FIGS. 38A and 38B.

While the foregoing description has made reference to various general concepts of lapping panels together and various features of particular embodiments of headgear formed by such lapped panels, it will be appreciated that any of the general concepts or features of particular embodiments may be combined in a multiplicity of different ways to provide a headgear.

According to various aspects of the disclosure a headgear comprising a plurality of panels each of which is at least partially lapped with another of the panels and which are bonded together at their laps by an adhesive may have a reduced weight relative to a headgear formed by other methods.

A headgear according to the disclosure may have a weight of less than about 30 g, of less than about 20 g, or of less than about 10 g.

In particular, various embodiments of a headgear 10 according to the disclosure may have a weight of about 17.5 g to about 27.5 g, and more particularly of about 25 g.

As an example, a headgear 10 of an embodiment shown and described in relation to FIGS. 18A-19B may have a weight of about 10 g to about 30 g. More specifically, a headgear 10 of the embodiment of FIG. 18A-19B may have a weight of about 20 g.

The invention claimed is:

1. A headgear for a patient interface, the headgear comprising:
    a rear portion configured for location at a rear position of a user's head in use;
    a pair of upper side strap portions, each of the pair of upper side strap portions comprising a first end portion configured to connect to the patient interface and a second end portion connected to the rear portion;
    a pair of lower side strap portions, each of the pair of lower side strap portions comprising a first end portion configured to connect to the patient interface and a second end portion connected to the rear portion;
    a pair of crown strap portions connected to a respective one of the upper side strap portions, wherein the pair of crown strap portions and the rear portion form a closed rear loop in use;
    the rear portion comprising an upper peripheral edge extending between the pair of crown strap portions; a lower peripheral edge extending between the pair of lower side strap portions; and a pair of lateral peripheral edges extending between respective upper and lower strap portions and defining ear loops configured to be positioned behind the ear of the user in use and,
    wherein the rear portion is formed from individual fabric panels comprising a first extensible fabric panel and a second fabric panel, wherein the second fabric panel is bonded to the first extensible fabric panel forming a laminated panel layup having at least one lapped region and at least one unlapped region, the at least one unlapped region having an area defined by a convex upper edge and a concave lower edge, and
    wherein the at least one lapped region of the laminated panel layup is less extensible than the at least one unlapped region.

2. The headgear of claim 1, wherein the rear portion comprises an internal surface oriented towards the head of the user in use and an external surface oriented away from the head of the user in use, wherein the internal surface is formed by the first extensible fabric panel.

3. The headgear of claim 2, wherein the external surface is formed by the second fabric panel and the at least one unlapped region.

4. The headgear of claim 1, wherein first extensible fabric panel comprises the at least one unlapped region.

5. The headgear of claim 1, wherein the pair of crown strap portions comprise a slot and one half of a fastening system to couple with a corresponding half of the fastening system on another side of the crown strap portion.

6. A headgear for a patient interface, the headgear comprising:
    a rear portion configured for location at a rear position of a user's head in use;
    a pair of upper side strap portions, each of the pair of upper side strap portions comprising a first end portion configured to connect to the patient interface and a second end portion connected to the rear portion;
    a pair of lower side strap portions, each of the pair of lower side strap portions comprising a first end portion configured to connect to the patient interface and a second end portion connected to the rear portion;
    the rear portion comprising a first fabric panel and a second fabric panel bonded to the first fabric panel forming a laminated panel layup having a lapped region formed by the first and second fabric panels, and at least one unlapped region formed by the first fabric panel, the at least one unlapped region having an area defined by a convex upper edge and a concave lower edge.

7. The headgear of claim 6, wherein the at least one lapped region of the laminated panel layup is less extensible than the at least one unlapped region.

8. The headgear of claim 6, wherein the lapped region includes bonded regions where adjacent panel surfaces have been bonded together and non-bonded regions where adjacent panel surfaces are not bonded together.

9. The headgear of claim 6, wherein the rear portion comprises an internal surface oriented towards the head of the user in use and an external surface oriented away from the head of the user in use, wherein the internal surface is formed by the first fabric panel, and wherein the external surface is formed by the second fabric panel and the at least one unlapped region.

10. A rear portion of a headgear for use with a patient interface, the rear portion comprising:
    a laminate of individual fabric panels, the laminate of individual fabric panels comprising:
        a first fabric panel comprising a first upper peripheral edge, a first lower peripheral edge, and a pair of first lateral peripheral edges; and
        a second fabric panel comprising a second upper peripheral edge, a second lower peripheral edge, and a pair of second lateral peripheral edges,
    where the second fabric panel is bonded to the first fabric panel forming a laminated panel layup having at least one lapped region and at least one unlapped region, the at least one unlapped region being located between the first lower peripheral edge and the second lower peripheral edge and defining an area having a convex upper edge and a concave lower edge, wherein the concave lower edge is coextensive with at least a portion the first lower peripheral edge.

11. The rear portion of claim 10, wherein the rear portion comprises a first surface and a second surface, wherein the first surface is defined by the first fabric panel, and wherein the second surface defined is by the second fabric panel and the at least one unlapped region.

12. The rear portion of claim 10, wherein the first fabric panel comprises the at least one unlapped region.

13. The rear portion of claim 10, wherein the first fabric panel and the second fabric panel are different materials.

14. The rear portion of claim 10, wherein the at least one lapped region comprises bonded regions where adjacent panel surfaces have been bonded together, and non-bonded regions where adjacent panel surfaces are not bonded together.

15. The rear portion of claim 10, wherein the first upper peripheral edge of the first fabric panel is longer than the first lower peripheral edge.

16. The rear portion of claim 10, wherein the second upper peripheral edge of the second fabric panel is longer that the second lower peripheral edge.

17. The rear portion of claim 10, wherein each of the pair of first lateral peripheral edges comprise first and second curved edge portions.

18. The rear portion of claim 17, wherein the first curved edge portions are longer that the second curved edge portions.

19. The rear portion of claim 17, wherein the second curved edge portions are adjacent the first upper peripheral edge.

20. A rear portion of a headgear for use with a patient interface comprising a laminate of individual fabric panels, the laminate of individual fabric panels consisting essentially of:

a first fabric panel comprising a first upper peripheral edge, a first lower peripheral edge, and a pair of first lateral peripheral edges; and a second fabric panel comprising a second peripheral upper edge, a second peripheral lower edge, and a pair of second lateral peripheral edges, wherein the second fabric panel is bonded to the first fabric panel forming a laminated panel layup having at least one lapped region and at least one unlapped region, the at least one unlapped region being located between the first lower peripheral edge and the second lower peripheral edge and defining an area having a convex upper edge and a concave lower edge.

\* \* \* \* \*